US012174192B2

(12) United States Patent
Willingham et al.

(10) Patent No.: US 12,174,192 B2
(45) Date of Patent: *Dec. 24, 2024

(54) METHODS FOR DETECTING AND TREATING CANCERS HAVING ADENOSINE PATHWAY ACTIVATION

(71) Applicant: Corvus Pharmaceuticals, Inc., Burlingame, CA (US)

(72) Inventors: Stephen Willingham, Sunnyvale, CA (US); Andrew Hotson, Burlingame, CA (US); Richard A. Miller, Portola Valley, CA (US)

(73) Assignee: Corvus Pharmaceuticals, Inc., Burlingame, CA (US)

( * ) Notice: Subject to any disclaimer, the term of this patent is extended or adjusted under 35 U.S.C. 154(b) by 959 days.

This patent is subject to a terminal disclaimer.

(21) Appl. No.: 17/259,298

(22) PCT Filed: Jul. 12, 2019

(86) PCT No.: PCT/US2019/041682
§ 371 (c)(1),
(2) Date: Jan. 11, 2021

(87) PCT Pub. No.: WO2020/014657
PCT Pub. Date: Jan. 16, 2020

(65) Prior Publication Data
US 2021/0255190 A1 Aug. 19, 2021

Related U.S. Application Data

(60) Provisional application No. 62/846,524, filed on May 10, 2019, provisional application No. 62/757,623, filed on Nov. 8, 2018, provisional application No. 62/742,912, filed on Oct. 8, 2018, provisional application No. 62/697,303, filed on Jul. 12, 2018.

(51) Int. Cl.
*C12Q 1/6886* (2018.01)
*G01N 33/574* (2006.01)

(52) U.S. Cl.
CPC ..... *G01N 33/57484* (2013.01); *C12Q 1/6886* (2013.01); *G01N 2333/70596* (2013.01); *G01N 2800/52* (2013.01)

(58) Field of Classification Search
CPC ............... C07K 14/705; C12Q 1/6886; C12Q 2600/158; G01N 2800/7028; G01N 33/57484
See application file for complete search history.

(56) References Cited

U.S. PATENT DOCUMENTS

2014/0045715 A1 2/2014 Lin et al.
2017/0184602 A1 6/2017 Martini et al.
2019/0046448 A1* 2/2019 Wu ........................ A61K 9/1647
2019/0231783 A1 8/2019 Xu et al.
2021/0254178 A1* 8/2021 Willingham ........... C07K 14/47

FOREIGN PATENT DOCUMENTS

| JP | 2009515148 A | 4/2009 |
| JP | 2015516369 A | 6/2015 |
| WO | WO-02/055083 A1 | 7/2002 |
| WO | WO-2009/156737 A1 | 12/2009 |
| WO | WO-2014/153424 A1 | 9/2014 |
| WO | WO-2015116868 A2 | 8/2015 |

(Continued)

OTHER PUBLICATIONS

Monti et al., "The CC Chemokine MCP-1/CCL2 in Pancreatic Cancer Progression: Regulation of Expression and Potential Mechanism of Antimalignant Activity," Cancer Research, Nov. 1, vol. 63, pp. 7451-7461. (Year: 2003).*
Gui et al., "Overexpression of CXCL3 can enhance the oncogenic potential of prostate cancer," Int. Urol. Nephrol., vol. 48, pp. 701-709. (Year: 2016).*
Slettenaar et al., "The chemokine network: A target in cancer biology", Advanced Drug Delivery Reviews, vol. 58, pp. 962-974. (Year: 2006).*
Ager, C. et al. (2016) "31st Annual Meeting and Associated Programs of the Society for Immunotherapy of Cancer (SITC 2016): part two," *Journal for ImmunoTherapy of Cancer*, Biomed Central Ltd, London, UK, UK, vol. 4, No. 1, Nov. 16, 2016 (Nov. 16, 2016), pp. 107-221, XP021241441, DOI: 10.1186/S40425-016-0173-6.

(Continued)

*Primary Examiner* — Young J Kim
(74) *Attorney, Agent, or Firm* — Mintz, Levin, Cohn, Ferris, Glovsky and Popeo, P.C.

(57) ABSTRACT

This disclosure relates to methods for detecting a level of expression of one or more genes (or proteins) in a subject having or suspected of having cancer, and optionally treating the subject with an adenosine pathway antagonist, for example an adenosine A2A receptor (ADORA2A) antagonist, to treat the cancer. The genes (or proteins) include, without limitation, CD68, CD163, LBP, CCL2, CCL3, CCL7, CCL24, CCNE1, CD 14, CD300E, CD86, CD93, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, IL1A, IE-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, C1R, C1S, C4BPA, CCL11, CCL20, CXCL16, CXCL2, HAMP, HSD11B1, ITGAM, LIF, SAA1, TFRC, TLR5, TNFSF14, TREM2, APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD 164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, VEGFA, S100A8, and/or WDR830S.

11 Claims, 18 Drawing Sheets

(56) References Cited

FOREIGN PATENT DOCUMENTS

| WO | WO-2017/017623 | A1 | | 2/2017 | | |
|---|---|---|---|---|---|---|
| WO | WO-2017/019897 | A1 | | 2/2017 | | |
| WO | WO-2017112917 | A1 | * | 6/2017 | ........... | A61K 31/519 |
| WO | WO-2017/181111 | A2 | | 10/2017 | | |
| WO | WO-2018/067991 | A1 | | 4/2018 | | |
| WO | WO-2018/111890 | A1 | | 6/2018 | | |
| WO | WO-2018/145023 | A1 | | 8/2018 | | |
| WO | WO-2018/183965 | A1 | | 10/2018 | | |
| WO | WO-2018/187484 | A1 | | 10/2018 | | |
| WO | WO-2019/090347 | A1 | | 5/2019 | | |
| WO | WO-2019/090348 | A1 | | 5/2019 | | |
| WO | WO-2019/090347 | A8 | | 6/2019 | | |
| WO | WO-2019/152798 | A1 | | 8/2019 | | |
| WO | WO-2020/068583 | A1 | | 4/2020 | | |

OTHER PUBLICATIONS

Cesano, A. (2015). "nCounter PanCancer Immune Profiling Panel (NanoString Technologies, Inc., Seattle, WA)." *Journal for ImmunoTherapy of Cancer*, 3:42, vol. 3, No. 1, Dec. 1, 2015 (Dec. 1, 2015), 3 pages. XP55908072, DOI: 10.1186/s40425-015-0088-7 Retrieved from the Internet: URL:https://jitc.biomedcentral.com/track/pdf/10.1186/s40425-015-0088-7.pdf.

Danaher, P. et al. (2017). "Gene expression markers of Tumor Infiltrating Leukocytes." *Journal for ImmunoTherapy of Cancer*, Biomed Central LTD, London, UK, vol. 5, No. 18, Feb. 21, 2017 (Feb. 21, 2017), pp. 1-15, XP021242443, DOI: 10.1186/S40425-017-0215-8.

Serra, S. et al. (2015). "Adenosine Signaling Mediates Hypoxic Responses in the Chronic Lymphocytic Leukemia Microenvironment." *Blood*. Dec. 3, 2015 (Dec. 3, 2015), pp. 4145-4145. XP055676358, DOI: 10.1182/blood.V126.23.4145.4145, Retrieved from the Internet: URL:https://watermark.silverchair.com/advances000984.pdf?token=AQECAHi208BE49Ooan9kkhW_Ercy7Dm3ZL9Cf3qfKAc485ysgAAA58wggObBgkqhkiG9w0BBwaggOMMIIDiAIBADCCA4EGCSqGSIb3DOEHATAeBglghkgBZOMEAS4wEQQMpTvgX7kTmCbWR5EtAgEOgIIDUvO2aPw30K0MCrYJWjVeA7jYxYxKChZMW_TglyiQCQjICg5lh5X8a-7vOJAIWxBKfrCG1HNvNRM 78imQI9AWd.

Veldman-Jones, M.H. et al. (2015). "Evaluating Robustness and Sensitivity of the NanoString Technologies nCounter Platform to Enable Multiplexed Gene Expression Analysis of Clinical Samples." *Cancer Research*, vol. 75, No. 13, Jul. 1, 2015 (Jul. 1, 2015), pp. 2587-2593, XP55907999, US, ISSN: 0008-5472, DOI: 10.1158/0008-5472.CAN-15-0262, Retrieved from the Internet: URL:https://aacrjournals.org/cancerres/article-pdf/75/13/2587/2717915/2587.pdf.

Walters, M. (2017). "32nd Annual Meeting and Pre-Conference Programs of the Society for Immunotherapy of Cancer (SITC 2017): Part Two." National Harbor, MD, USA. Nov. 8-12, 2017— Abs p. 498, *Journal for ImmunoTherapy of Cancer*, vol. 5, No. S2, Nov. 1, 2017 (Nov. 1, 2017), 128 pages. XP055846682, DOI: 10.1186/s40425-017-0288-4, Retrieved from the Internet: URL:https://jitc.bmj.com/content/jitc/5/Suppl_2/87.full.pdf.

Willingham S. et al. (2018). "Identification of adenosine pathway genes associated with response to therapy with the adenosine receptor antagonist CPI-444." *Annals of Oncology*, vol. 29, Oct. 1, 2018 (Oct. 1, 2018), pp. viii403-viii404, XP055908398, NL, ISSN: 0923-7534, DOI: 10.1093/annonc/mdy288.010.

Denardo, D. G. et al. (2011, e-published Apr. 3, 2011), "Leukocyte Complexity Predicts Breast Cancer Survival and Functionally Regulates Response to Chemotherapy." Cancer Discovery, 1(1), 54-67. https://doi.org/10.1158/2159-8274.CD-10-0028.

International Preliminary Report on Patentability issued in International Application No. PCT/US2019/041682, mailed Jan. 12, 2021 (Jan. 12, 2021). 16 pages.

International Preliminary Report on Patentability issued in International Application No. PCT/US2019/041695, mailed Jan. 12, 2021 (Jan. 12, 2021). 15 pages.

International Search Report and Written Opinion issued in International Application No. PCT/US2019/041682, mailed Nov. 18, 2019. 22 pages.

International Search Report and Written Opinion issued in International Application No. PCT/US2019/041695, mailed Nov. 18, 2019. 21 pages.

Leone, R.D. et al. (2018). "Targeting adenosine for cancer immunotherapy." *j. immunotherapy cancer* 6, 57; pp. 1-9 https://doi.org/10.1186/s40425-018-0360-8.

Mcdermott, D.F. et al. (2018), "Clinical activity and molecular correlates of response to atezolizumab alone or in combination with bevacizumab versus sunitinib in renal cell carcinoma." *Nat Med* 24, 749-757. https://doi.org/10.1038/s41591-018-0053-3.

Serra, S. et al. (2016), "Adenosine signaling mediates hypoxic responses in the chronic lymphocytic leukemia microenvironment." *Blood Adv.*, 1(1):47-61. doi: 10.1182/bloodadvances.2016000984. PMID: 29296695; PMCID: PMC5744057.

Sun, S. et al. (2016, e-published Jun. 25, 2016), "The Expression and Relationship of CD68-Tumor-Associated Macrophages and Microvascular Density With the Prognosis of Patients With Laryngeal Squamous Cell Carcinoma." Clinical and Experimental Otorhinolaryngology, 9(3), 270-277. https://doi.org/10.21053/ceo.2015.01305.

Alsaab, H.O. et al. (Aug. 23, 2017). "PD-1 and PD-L1 Checkpoint Signaling Inhibition for Cancer Immunotherapy: Mechanism, Combinations, and Clinical Outcome." Front. Pharmacol. 8(561), pp. 1-15.

Anti-CD73 [1 E9] in Absolute Antibodies from Absolute Biotech Company retrieved on Oct. 24, 2023 online from <U RL: https://absoluteantibody.com/product/anti-cd73-1e9/> (Year: 2023). 3 pages.

Burkholder, B. et al. (2014)."Tumor-induced perturbations of cytokines and immune cell networks." Biochimica et Biophysica Acta., 1845, 182-201.

CAS 1202402-40-1 in American Elements retrieved Oct. 24, 2023 online at <URL: https://www.americanelements.com/1202402 -40-1-s-7-5-methylfuran-2-yl-3-6-tetrahydrofuran-3-yl-oxy-methyl-pyridin-2-yl-methyl-3h-1-2-3-triazolo-4-5> (Year: 2023). 1 page.

Chittezhath, M. et al. (2014). " Molecular Profiling Reveals a Tumor-Promoting Phenotype of Monocytes and Macrophages in Human Cancer Progression." Immunity. 41: 815-829. Nov. 20, 2014.

Corvus Pharmaceuticals. Press Release on Jun. 5, 2017 retrieved online on Oct. 20, 2023 from <URL: http:// investor.corvuspharma.com/news-releases/news-release-details/corvus-pharmaceuticals-announces-interim-results-demonstrating > (Year: 2017). 8 pages.

Emens et al. [Slideshow] (Apr. 4, 2017) CPI-444, an oral adenosine A2A receptor (A2AR) antagonist, demonstrates clinical activity in patients with advanced solid tumors. AACR Annual Meeting 2017. Washington, DC. (Year: 2017). 21pages.

Feoktistov, I. et al. (e-pub Jan. 31, 2002). "Differential Expression of Adenosine Receptors in Human Endothelial Cells Role of A2B Receptors in Angiogenic Factor Regulation—Role of A2B Receptors in Angiogenic Factor Regulation." Circulation Research, 90(5); 531-538.

Fong, L. et al. (2020). "Adenosine A2A Receptor Blockade as an Immunotherapy for Treatment-Refractory Renal Cell Cancer." Cancer Discovery, 10(1), 40-53. https://doi.org/10.1158/2159-8290.CD-19-0980.

Garcia-Gomez, A. et al. (Jun. 4, 2014). "Transcriptomic profile induced in bone marrow mesenchymal stromal cells after interaction with multiple myeloma cells: implications in myeloma progression and myeloma bone disease." Oncotarget, 5(18), 8284-8305.

Journal of Thoracic Oncology, Oct. 2018, vol. 13, No. 10S, pp. S533-S534.

Liang et al. Fucosyltransferase VII promotes proliferation via the EGFR/AKT/mTOR pathway in A549 cells. Onco Targets Ther. Aug. 7, 2017;10:3971-3978. doi: 10.2147/OTT.S140940. PMID: 28860805; PMCID: PMC5558582. (Year: 2017).

(56) References Cited

OTHER PUBLICATIONS

Najjar et al. (2017). "Myeloid-Derived Suppressor Cell Subset Accumulation in Renal Cell Carcinoma Parenchyma Is Associated with Intratumoral Expression of IL1β, IL8, CXCL5, and Mip-1α." Clin Cancer Res, 23(9), 2346-2355.
Ortega-Martinez, S. (2015). "A new perspective on the role of the CREB family of transcription factors in memory consolidation via adult hippocampal neurogenesis." Front. Mol. Neurosci. 8:46. doi: 10.3389/fnmol.2015.00046 (Year: 2015). 12 pages.
Patnaik et al. (2016). "Phase 1/1b multicenter trial of the adenosine A2a receptor antagonist (A2aR) CPI-444 as single agent and in combination with atezolizumab (ATZ) in patients(Pts) with advanced cancers." Annals of Oncology. Oct. 1, 2016; 27(6 Supplement): vi378 (Year: 2017). 1 page.
Shi et al. (2016). "Increased expression of EHF via gene amplification contributes to the activation of HER family signaling and associates with poor survival in gastric cancer." Cell Death Dis. Oct. 27, 2016;7(10):e2442. doi: 10.1038/cddis.2016.346. PMID: 27787520; PMCID: PMC5134001. (Year: 2016). 14 pages.
Sorrentino et al. (2017). "Role of adenosine in tumor progression: focus on A2B receptor as potential therapeutic target." J Cancer Metastasis Treat 2017;3:127-38. DOI: 10.20517/2394-4722.2017.29 (Year: 2017).
Willingham et al. (Jul. 1, 2017). Abstract 5593: Inhibition of A2AR induces anti-tumor immunity alone and in combination with anti-PD-L1 in preclinical and clinical studies. Cancer Research. Jul. 1, 2017. 77(13 Supplement): 5593. (Year: 2017). 2 pages.

\* cited by examiner

FIGURE 2A
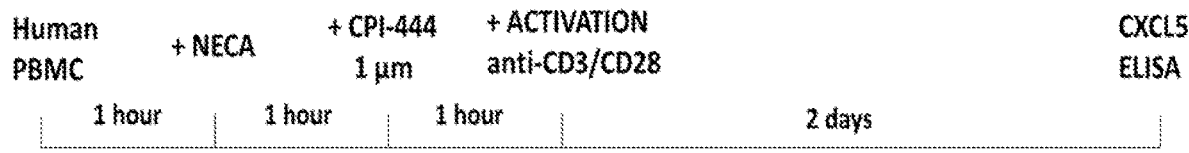
FIGURE 2B
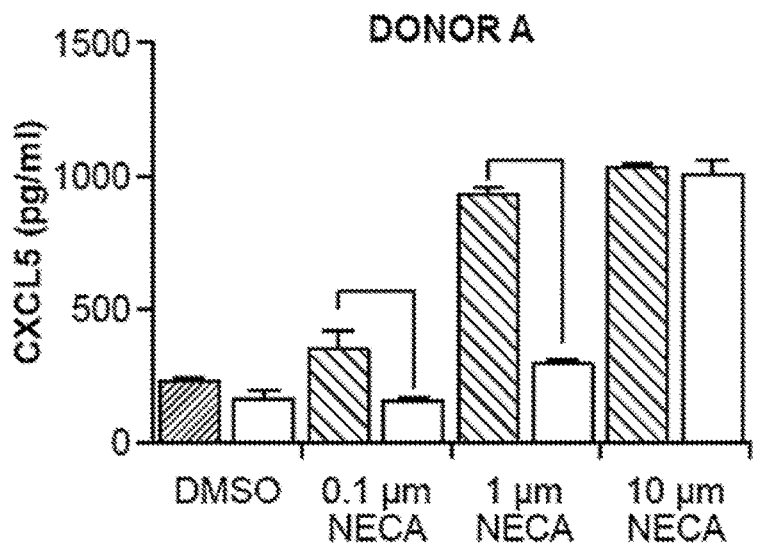
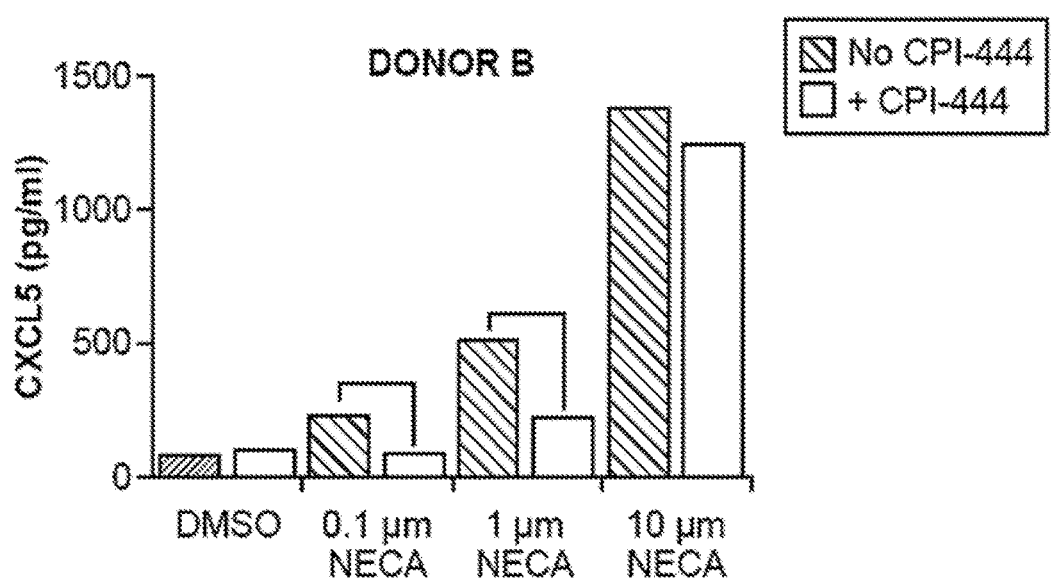

FIGURE 3A

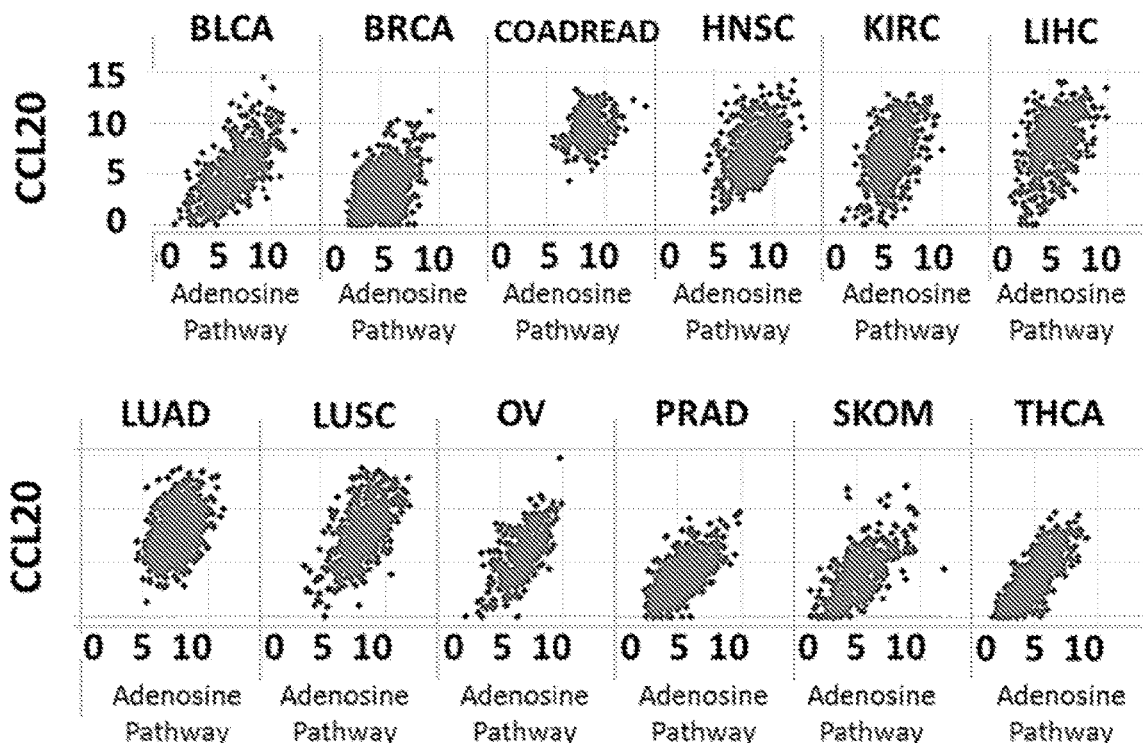

FIGURE 3B

| Indication | data_set | Spearman's correlation | percentile |
|---|---|---|---|
| Lung adenocarcinoma | LUAD | 0.40547654 | 0.67842605 |
| Lung squamous cell carcinoma | LUSC | 0.57534957 | 0.54274084 |
| Breast invasive carcinoma | BRCA | 0.41535422 | 4.34192673 |
| Prostate adenocarcinoma | PRAD | 0.68349934 | 0.27137042 |
| Kidney renal clear cell carcinoma | KIRC | 0.4559302 | 2.17096336 |
| Skin Cutaneous Melanoma | SKCM | 0.61775839 | 0.40705563 |
| Thyroid carcinoma | THCA | 0.81603301 | 0.27137042 |
| Colorectal adenocarcinoma | COADREAD | 0.37693378 | 1.62822252 |
| Head and Neck squamous cell carcinoma | HNSC | 0.43295443 | 1.08548168 |
| Ovarian serous cystadenocarcinoma | OV | 0.61356175 | 0.54274084 |
| Bladder urothelial carcinoma | BLCA | 0.66975671 | 0.40705563 |
| Liver hepatocellular carcinoma | LIHC | 0.48098469 | 1.08548168 |

Adenosine Composite Gene Expression - LOW

Adenosine Composite Gene Expression - HIGH

METHODS FOR DETECTING AND
TREATING CANCERS HAVING ADENOSINE
PATHWAY ACTIVATION

CROSS-REFERENCE TO RELATED
APPLICATIONS

This application is a Section 371 US national phase of International Application No. PCT/US2019/041682 filed Jul. 12, 2019, which claims priority to U.S. Provisional Patent Application No. 62/697,303, filed on Jul. 12, 2018; U.S. Provisional Patent Application No. 62/742,912, filed on Oct. 8, 2018; U.S. Provisional Patent Application No. 62/757,623, filed on Nov. 8, 2018; and U.S. Provisional Patent Application No. 62/846,524, filed on May 10, 2019; each of which is incorporated herein by reference in its entirety.

BACKGROUND

Adenosine is a signaling molecule used by the body to limit inflammation and immune responses. Many different types of tumors produce and actively sustain high levels of adenosine within the tumor microenvironment. One of the ways that tumor cells produce adenosine is by expressing high levels of an enzyme on their surface called CD73. CD73 generates adenosine, and this contributes to the maintenance of high levels of adenosine in the tumor microenvironment.

Adenosine hinders the ability of the immune system to attack the tumor, mainly in two ways: (1) by blocking the activation and effectiveness of immune cells that are capable of destroying tumor cells, and (2) by increasing the number of regulatory T-cells (T-regs) that act to suppress immune cells from responding to the tumor. As tumor cells evolve and form cancerous growths, they utilize these processes to evade immune attack and promote their own survival.

The adenosine that tumors produce interacts with adenosine receptors on the surface of invading immune cells. A type of adenosine receptor known as A2A is expressed on several cells of the immune system, including T-cells, NK cells, macrophages and dendritic cells. Binding of adenosine to the A2A receptor has the effect of dampening the ability of the immune cells to attack tumors. A significant body of scientific data indicates that targeting the adenosine-cancer axis through the A2A receptor can promote anti-tumor immune responses to occur, leading to tumor regression.

Measurement of adenosine levels in tumors is technically challenging, since the half-life of the molecule is less than ten seconds. Thus, it would be beneficial to find a method for determining whether adenosine is up-regulated in a tumor that does not require direct measurement of adenosine levels in the tumor.

BRIEF SUMMARY

The present disclosure relates to a method for detecting a level of expression of one or more genes or proteins in a subject having or suspected of having cancer, comprising detecting the level of expression of the one or more genes in a biological sample from the subject. In one aspect, the level of expression (e.g., compared to a control) of the one or more genes indicates that the cancer can be treated by administration of an adenosine pathway inhibitor.

In embodiments, the genes or proteins are selected from CD68, CD163, LBP, BIRC5, BST1, CARD11, CCL2, CCL3, CCL7, CCL24, CCNE1, CD14, CD300E, CD86, CD93, CDK1, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, IL1A, IL-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, C1R, C1S, C4BPA, CCL11, CCL20, CXCL16, CXCL2, HAMP, HSD11B1, ITGAM, LIF, SAA1, TFRC, TLR5, TNFRSF11A, TNFSF14, TREM1, TREM2, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, TNFSF18, APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CD36, CDH1, CDH5, CREB1, DOCK9, ENG, HMGB1, ITGA1, JAM3, MAF, MAPK3, MAPK8, MCAM, MFGE8, MIF, NOTCH1, NRP1, PRKCE, RORA, TLR3, SMAD2, TAL1, THY1, TNFSF12, TRAF6, TXNIP, VEGFA, S100A8, and/or WDR83OS. In embodiments, genes are selected from CXCL1, CXCL2, CXCL3, CXCL5, SERPINB2, IL8, and/or IL-1β. In embodiments, the genes or proteins are selected from BIRC5, BST1, CARD11, CCL2, CCL3, CCL7, CCL24, CCNE1, CD14, CD300E, CD86, CD93, CDK1, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, IL1A, IL-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, C1R, C1S, C4BPA, CCL11, CCL20, CXCL16, CXCL2, HAMP, HSD11B1, ITGAM, LIF, SAA1, TFRC, TLR5, TNFRSF11A, TNFSF14, TREM1, TREM2, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, TNFSF18, APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CD36, CDH1, CDH5, CREB1, DOCK9, ENG, HMGB1, ITGA1, JAM3, MAF, MAPK3, MAPK8, MCAM, MFGE8, MIF, NOTCH1, NRP1, PRKCE, RORA, TLR3, SMAD2, TAL1, THY1, TNFSF12, TRAF6, TXNIP, VEGFA, S100A8, and/or WDR83OS. In embodiments, expression of other genes is not detected. In embodiments, the method further comprises: (c) comparing the level of expression of the one or more genes in the sample to a level of expression of the one or more genes in a suitable control.

Without being bound by theory, it is believed that the expression level of one or more of the genes or proteins indicates a level of activation of the adenosine pathway in the subject (or in the cancer); activation may indicate the susceptibility of the cancer to an adenosine pathway inhibitor, e.g., an adenosine 2A receptor (ADORA2A) antagonist, adenosine 2B receptor antagonist, or adenosine deaminase. In embodiments, the method further comprises comparing the level of expression of the one or more genes or proteins in the sample to a level of expression of the one or more genes or proteins in a suitable control. In embodiments, the level of expression of the one or more genes or proteins is calculated as the mean of Log2 of the expression of each gene (or level of each protein).

The present disclosure further relates to a method of treating a subject having cancer, the method comprising: (a) obtaining a biological sample from the subject; (b) detecting a level of expression of one or more genes or proteins in the biological sample, wherein the genes are selected from CD68, CD163, LBP, BIRC5, BST1, CARD11, CCL2, CCL3, CCL7, CCL24, CCNE1, CD14, CD300E, CD86, CD93, CDK1, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, IL1A, IL-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, C1R, C1S, C4BPA, CCL11, CCL20, CXCL16, CXCL2, HAMP, HSD11B1, ITGAM, LIF, SAA1, TFRC, TLR5, TNFRSF11A, TNFSF14, TREM1, TREM2, TTK, ADA, BCL6, C2, CCL8, CEBPB, CFD, CSF1, CSF2RB, CXCR4, FCGR2A, IFI16, IRAK4, LY96, CXCR1, CXCR2, DMBT1, FOXJ1, ITCH, MAP2K2, PRAME, PSMD7, TNFSF18, APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CD36, CDH1, CDH5, CREB1, DOCK9, ENG, HMGB1, ITGA1, JAM3, MAF, MAPK3, MAPK8, MCAM, MFGE8, MIF, NOTCH1, NRP1, PRKCE, RORA, TLR3, SMAD2, TAL1, THY1, TNFSF12, TRAF6, TXNIP, VEGFA, S100A8, and/or WDR83OS; and (c) administering to the subject an effective amount of an adenosine pathway inhibitor (e.g., ADORA2A antagonist), thereby treating the cancer.

The present disclosure further relates to a method of treating a subject having cancer, the method comprising: (a) obtaining a biological sample from the subject; (b) detecting a level of expression of one or more genes or proteins in the biological sample, wherein the genes are selected from BIRC5, BST1, CARD11, CCL2, CCL3, CCL7, CCL24, CCNE1, CD14, CD300E, CD86, CD93, CDK1, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, IL1A, IL-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, C1R, C1S, C4BPA, CCL11, CCL20, CXCL16, CXCL2, HAMP, HSD11B1, ITGAM, LIF, SAA1, TFRC, TLR5, TNFRSF11A, TNFSF14, TREM1, TREM2, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, TNFSF18, APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CD36, CDH1, CDH5, CREB1, DOCK9, ENG, HMGB1, ITGA1, JAM3, MAF, MAPK3, MAPK8, MCAM, MFGE8, MIF, NOTCH1, NRP1, PRKCE, RORA, TLR3, SMAD2, TAL1, THY1, TNFSF12, TRAF6, TXNIP, VEGFA, S100A8, and/or WDR83OS; and (c) administering to the subject an effective amount of an adenosine pathway inhibitor (e.g., ADORA2A antagonist), thereby treating the cancer.

The present disclosure further relates to a method of identifying a subject for treatment with an adenosine pathway inhibitor (e.g., ADORA2A antagonist), said subject having or suspected of having cancer, the method comprising: (a) obtaining a biological sample from the subject; and (b) detecting a level of expression of one or more genes or proteins in the biological sample, wherein the genes or proteins are selected from CD68, CD163, LBP, CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18; wherein a level of expression of the one or more genes or proteins that is higher than a control indicates that the subject is a candidate for treatment with the adenosine pathway inhibitor.

The present disclosure further relates to a method of identifying a subject for treatment with an adenosine pathway inhibitor (e.g., ADORA2A antagonist), said subject having or suspected of having cancer, the method comprising: (a) obtaining a biological sample from the subject; and (b) detecting a level of expression of one or more genes or proteins in the biological sample, wherein the genes or proteins are selected from CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18; wherein a level of expression of the one or more genes or proteins that is higher than a control indicates that the subject is a candidate for treatment with the adenosine pathway inhibitor.

The present disclosure further relates to a method for selecting a subject for treatment with an adenosine pathway inhibitor, the subject having or suspected of having cancer, the method comprising: (a) obtaining a biological sample from the subject; (b) detecting a high level of expression of one or more genes or proteins in the biological sample, wherein the genes or proteins are selected from CD68, CD163, LBP, CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18; and (c) selecting the subject for treatment with an adenosine pathway inhibitor.

The present disclosure further relates to a method of identifying a subject for treatment with an adenosine pathway inhibitor (e.g., ADORA2A antagonist), said subject having or suspected of having cancer, the method comprising: (a) obtaining a biological sample from the subject; and (b) detecting a level of expression of one or more genes or proteins in the biological sample, wherein the genes or proteins are selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA; wherein a level of expression of the one or more genes or proteins that is lower than a control indicates that the subject is a candidate for treatment with an adenosine pathway inhibitor (e.g., ADORA2A antagonist).

The present disclosure further relates to a method for selecting a subject for treatment with an adenosine pathway inhibitor, the subject having or suspected of having cancer, the method comprising: (a) obtaining a biological sample from the subject; (b) detecting a low level of expression of one or more genes or proteins in the biological sample, wherein the genes or proteins are selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA; and (c) selecting the subject for treatment with an adenosine pathway inhibitor.

In embodiments is provided a method for detecting a level of expression of one or more genes in a subject having or suspected of having cancer, the method comprising: (a) obtaining a biological sample from the subject; and (b) detecting the level of expression of the one or more genes in the biological sample, wherein the genes are selected from CD68, CD163, LBP, CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18; wherein a level of expression of the one or more genes that is higher than a control indicates that the subject is a candidate for treatment with an adenosine pathway inhibitor (e.g., ADORA2A antagonist).

In embodiments is provided a method for detecting a level of expression of one or more genes in a subject having or suspected of having cancer, the method comprising: (a) obtaining a biological sample from the subject; and (b) detecting the level of expression of the one or more genes in the biological sample, wherein the genes are selected from CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18; wherein a level of expression of the one or more genes that is higher than a control indicates that the subject is a candidate for treatment with an adenosine pathway inhibitor (e.g., ADORA2A antagonist).

In embodiments, the genes are selected from CCL2, CCL3, CCL7, CD300E, CD93, CSF3, CXCL1, CXCL2, CXCL3, CXCL5, CXCL8, ECEL1, HAS1, IL-1β, IL8, IL23, INHBA, PADI2, PID1, PTGS2, SCL747, SERPINB2, ST6GALNAC2, and/or THBS1. In embodiments, genes are selected from CXCL1, CXCL2, CXCL3, CXCL5, SERPINB2, IL8, and/or IL-1β. In embodiments, the genes are selected from BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18. In embodiments, expression of other genes is not detected.

In embodiments is provided a method for detecting a level of expression of one or more genes in a subject having or suspected of having cancer, the method comprising: (a) obtaining a biological sample from the subject; and (b) detecting the level of expression of the one or more genes in the biological sample, wherein the genes are selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA; wherein a level of expression of the one or more genes that is lower than a control indicates that the subject is a candidate for treatment with an adenosine pathway inhibitor (e.g., ADORA2A antagonist). In embodiments, the genes are selected from CCL24, CCNE1, EHF, FUT7, GALM, GBP6, IL5, LAP3, MRPL11, OST4, WDR83OS, and/or TBX21. In embodiments, the genes are selected from EHF, FUT7, and/or OST4. In embodiments, the genes are selected from AKT3, BMI1, CD164, CD34, CD36, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, VEGFA, APP, ATG10, BCL2, CCL15, CD24, CD46, CD59, CDH1, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, MIF, PPARG, RORA, RORC, SPA17, STAT5B, TLR3, and/or TOLLIP.

In embodiments is provided a method of treating a subject having cancer, the method comprising: (a) obtaining a biological sample from the subject; (b) detecting a level of expression of one or more genes in the biological sample, wherein the genes are selected from CD68, CD163, LBP, BIRC5, BST1, CARD11, CCL2, CCL3, CCL7, CCL24, CCNE1, CD14, CD300E, CD86, CD93, CDK1, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, ILIA, IL-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, C1R, C1S, C4BPA, CCL11, CCL20, CXCL16, CXCL2, HAMP, HSD11B1, ITGAM, LIF, SAA1, TFRC, TLR5, TNFRSF11A, TNFSF14, TREM1, TREM2, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, TNFSF18, APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CD36, CDH1, CDH5, CREB1, DOCK9, ENG, HMGB1, ITGA1, JAM3, MAF, MAPK3, MAPK8, MCAM, MFGE8, MIF, NOTCH1, NRP1, PRKCE, RORA, TLR3, SMAD2, TAL1, THY1, TNFSF12, TRAF6, TXNIP, VEGFA, S100A8, and/or WDR83OS; and (c) administering to the subject an effective amount of an adenosine pathway inhibitor (e.g., ADORA2A antagonist), thereby treating the cancer.

In embodiments is provided a method of treating a subject having cancer, the method comprising: (a) obtaining a biological sample from the subject; (b) detecting a level of expression of one or more genes in the biological sample, wherein the genes are selected from BIRC5, BST1, CARD11, CCL2, CCL3, CCL7, CCL24, CCNE1, CD14, CD300E, CD86, CD93, CDK1, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, IL1A, IL-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, C1R, C1S, C4BPA, CCL11, CCL20, CXCL16, CXCL2, HAMP, HSD11B1, ITGAM, LIF, SAA1, TFRC, TLR5, TNFRSF11A, TNFSF14, TREM1, TREM2, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18. In embodiments, the genes are selected from CCL2, CCL3, CCL7, CD300E, CD93, CSF3, CXCL1, CXCL2, CXCL3, CXCL5, CXCL8, ECEL1, HAS1, IL-1β, IL8, IL23, INHBA, PADI2, PID1, PTGS2, SCL747, SERPINB2, ST6GALNAC2, and/or THBS1. In embodiments, genes are selected from CXCL1, CXCL2, CXCL3, CXCL5, SERPINB2, IL8, and/or IL-1β. In embodiments, genes are selected from IL1β, PTGS2, CXCL1, CXCL2, CXCL3, CXCL5, CXCL6, and CXCL8. In embodiments, genes are selected from BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18. In embodiments, genes are selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA. In embodiments, genes are selected from AKT3, BMI1, CD164, CD34, CD36, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, VEGFA, APP, ATG10, BCL2, CCL15, CD24, CD46, CD59, CDH1, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, MIF, PPARG, RORA, RORC, SPA17, STAT5B, TLR3, and/or TOLLIP. In embodiments, genes are selected from EHF, FUT7, and/or OST4. In embodiments, expression of other genes is not detected.

In embodiments is provided a method of identifying a subject for treatment with an adenosine pathway inhibitor (e.g., ADORA2A antagonist), said subject having or suspected of having cancer, the method comprising: (a) obtaining a biological sample from the subject; and (b) detecting a level of expression of one or more genes in the biological sample, wherein the genes are selected from CD68, CD163, LBP, CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18; wherein a level of expression of the one or more genes that is higher than a control indicates that the subject is a candidate for treatment with an adenosine pathway inhibitor (e.g., ADORA2A antagonist).

In embodiments is provided a method of identifying a subject for treatment with an adenosine pathway inhibitor (e.g., ADORA2A antagonist), said subject having or suspected of having cancer, the method comprising: (a) obtaining a biological sample from the subject; and (b) detecting a level of expression of one or more genes in the biological sample, wherein the genes are selected from CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18; wherein a level of expression of the one or more genes that is higher than a control indicates that the subject is a candidate for treatment with an adenosine pathway inhibitor (e.g., ADORA2A antagonist).

In embodiments is provided a method of identifying a subject for treatment with an adenosine pathway inhibitor (e.g., ADORA2A antagonist), said subject having or suspected of having cancer, the method comprising: (a) obtaining a biological sample from the subject; and (b) detecting a level of expression of one or more genes in the biological sample, wherein the genes are selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA; wherein a level of expression of the one or more genes that is lower than a control indicates that the subject is a candidate for treatment with an adenosine pathway inhibitor (e.g., ADORA2A antagonist). In embodiments, the genes are selected from EHF, FUT7, and/or OST4.

In embodiments is provided a method of treating a subject having cancer, the method comprising: (a) obtaining a biological sample from the subject; (b) detecting a level of expression of one or more genes in the biological sample, wherein the genes are selected from CD68, CD163, LBP, CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18; wherein a level of expression of the one or more genes that is higher than a control indicates that the subject is a candidate for treatment with an adenosine pathway inhibitor (e.g., ADORA2A antagonist); and (c) administering to the subject an effective amount of the adenosine pathway inhibitor (e.g., ADORA2A antagonist), thereby treating the cancer.

In embodiments is provided a method of treating a subject having cancer, the method comprising: (a) obtaining a biological sample from the subject; (b) detecting a level of expression of one or more genes in the biological sample, wherein the genes are selected from CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, ILIA, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18; wherein a level of expression of the one or more genes that is higher than a control indicates that the subject is a candidate for treatment with an adenosine pathway inhibitor (e.g., ADORA2A antagonist); and (c) administering to the subject an effective amount of the adenosine pathway inhibitor (e.g., ADORA2A antagonist), thereby treating the cancer.

In embodiments, the genes are selected from CCL2, CCL3, CCL7, CD300E, CD93, CSF3, CXCL1, CXCL2, CXCL3, CXCL5, CXCL8, ECEL1, HAS1, IL-1β, IL8, IL23, INHBA, PADI2, PID1, PTGS2, SCL747, SERPINB2, ST6GALNAC2. In embodiments, expression of other genes is not detected.

In embodiments is provided a method of treating a subject having cancer, the method comprising: (a) obtaining a biological sample from the subject; (b) detecting a level of expression of one or more genes in the biological sample, wherein the genes are selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA, wherein a level of expression of the one or more genes that is lower than a control indicates that the subject is a candidate for treatment with an adenosine pathway inhibitor (e.g., ADORA2A antagonist); and (c) administering to the subject an effective amount of the adenosine pathway inhibitor (e.g., ADORA2A antagonist), thereby treating the cancer. In embodiments, the genes are selected from EHF, FUT7, and/or OST4. In embodiments, expression of other genes is not detected.

In embodiments is provided a method of treating a subject having cancer, the method comprising: (a) obtaining a biological sample from the subject; (b) receiving an identification of a patient as having a reduced level of expression (e.g., relative to a control) of one or more genes selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA, and/or an increased level of expression (e.g., relative to a control) of one or more genes selected from CD68, CD163, LBP, CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18 in a biological sample; and (c) administering to the subject an effective amount of an adenosine pathway inhibitor (e.g., ADORA2A antagonist), thereby treating the cancer.

In embodiments is provided a method of treating a subject having cancer, the method comprising: (a) obtaining a biological sample from the subject; (b) receiving an identification of a patient as having a reduced level of expression (e.g., relative to a control) of one or more genes selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA, and/or an increased level of expression (e.g., relative to a control) of one or more genes selected from CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18 in a biological sample; and (c) administering to the subject an effective amount of an adenosine pathway inhibitor (e.g., ADORA2A antagonist), thereby treating the cancer.

In embodiments is provided a method of treating a subject having cancer, the method comprising: (a) obtaining a biological sample from the subject; (b) detecting a level of expression of one or more proteins in the biological sample, wherein the proteins are selected from CD68, CD163, LBP, BIRC5, BST1, CARD11, CCL2, CCL3, CCL7, CCL24, CCNE1, CD14, CD300E, CD86, CD93, CDK1, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, IL1A, IL-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, C1R, C1S, C4BPA, CCL11, CCL20, CXCL16, CXCL2, HAMP, HSD11B1, ITGAM, LIF, SAA1, TFRC, TLR5, TNFRSF11A, TNFSF14, TREM1, TREM2, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, TNFSF18, APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CD36, CDH1, CDH5, CREB1, DOCK9, ENG, HMGB1, ITGA1, JAM3, MAF, MAPK3, MAPK8, MCAM, MFGE8, MIF, NOTCH1, NRP1, PRKCE, RORA, TLR3, SMAD2, TAL1, THY1, TNFSF12, TRAF6, TXNIP, VEGFA, S100A8, and/or WDR83OS; and (c) administering to the subject an effective amount of an adenosine pathway inhibitor (e.g., ADORA2A antagonist), thereby treating the cancer.

In embodiments is provided a method of treating a subject having cancer, the method comprising: (a) obtaining a biological sample from the subject; (b) detecting a level of expression of one or more proteins in the biological sample, wherein the proteins are selected from BIRC5, BST1, CARD11, CCL2, CCL3, CCL7, CCL24, CCNE1, CD14, CD300E, CD86, CD93, CDK1, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, ILIA, IL-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, C1R, C1S, C4BPA, CCL11, CCL20, CXCL16, CXCL2, HAMP, HSD11B1, ITGAM, LIF, SAA1, TFRC, TLR5, TNFRSF11A, TNFSF14, TREM1, TREM2, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, TNFSF18, APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CD36, CDH1, CDH5, CREB1, DOCK9, ENG, HMGB1, ITGA1, JAM3, MAF, MAPK3, MAPK8, MCAM, MFGE8, MIF, NOTCH1, NRP1, PRKCE, RORA, TLR3, SMAD2, TAL1, THY1, TNFSF12, TRAF6, TXNIP, VEGFA, S100A8, and/or WDR83OS; and (c) administering to the subject an effective amount of an adenosine pathway inhibitor (e.g., ADORA2A antagonist), thereby treating the cancer.

In embodiments, the proteins are selected from CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18. In embodiments, the proteins are selected from CCL2, CCL3, CCL7, CD300E, CD93, CSF3, CXCL1, CXCL2, CXCL3, CXCL5, CXCL8, ECEL1, HAS1, IL-1β, IL8, IL23, INHBA, PADI2, PID1, PTGS2, SCL747, SERPINB2, ST6GALNAC2, and/or THBS1. In embodiments, proteins are selected from CXCL1, CXCL2, CXCL3, CXCL5, SERPINB2, IL8, and/or IL-1β. In embodiments, genes are selected from IL1B, PTGS2, CXCL1, CXCL2, CXCL3, CXCL5, CXCL6, and CXCL8. In embodiments, the proteins are selected from BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18. In embodiments, the proteins are selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA. In embodiments, the proteins are selected from AKT3, BMI1, CD164, CD34, CD36, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, VEGFA, APP, ATG10, BCL2, CCL15, CD24, CD46, CD59, CDH1, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, MIF, PPARG, RORA, RORC, SPA17, STAT5B, TLR3, and/or TOLLIP. In embodiments, the proteins are selected from EHF, FUT7, and/or OST4. In embodiments, expression of other proteins is not detected.

In embodiments is provided a method for detecting a level of expression of one or more proteins in a subject having or suspected of having cancer, the method comprising: (a) obtaining a biological sample from the subject; and (b) detecting the level of expression of the one or more proteins in the biological sample, wherein the proteins are selected from CD68, CD163, LBP, BIRC5, BST1, CARD11, CCL2, CCL3, CCL7, CCL24, CCNE1, CD14, CD300E, CD86, CD93, CDK1, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, ILIA, IL-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, C1R, C1S, C4BPA, CCL11, CCL20, CXCL16, CXCL2, HAMP, HSD11B1, ITGAM, LIF, SAA1, TFRC, TLR5, TNFRSF11A, TNFSF14, TREM1, TREM2, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, TNFSF18, APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CD36, CDH1, CDH5, CREB1, DOCK9, ENG, HMGB1, ITGA1, JAM3, MAF, MAPK3, MAPK8, MCAM, MFGE8, MIF, NOTCH1, NRP1, PRKCE, RORA, TLR3, SMAD2, TAL1, THY1, TNFSF12, TRAF6, TXNIP, VEGFA, S100A8, and/or WDR83OS.

In embodiments is provided a method for detecting a level of expression of one or more proteins in a subject having or suspected of having cancer, the method comprising: (a) obtaining a biological sample from the subject; and (b) detecting the level of expression of the one or more proteins in the biological sample, wherein the proteins are selected from BIRC5, BST1, CARD11, CCL2, CCL3, CCL7, CCL24, CCNE1, CD14, CD300E, CD86, CD93, CDK1, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, IL1A, IL-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, C1R, C1S, C4BPA, CCL11, CCL20, CXCL16, CXCL2, HAMP, HSD11B1, ITGAM, LIF, SAA1, TFRC, TLR5, TNFRSF11A, TNFSF14, TREM1, TREM2, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, TNFSF18, APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CD36, CDH1, CDH5, CREB1, DOCK9, ENG, HMGB1, ITGA1, JAM3, MAF, MAPK3, MAPK8, MCAM, MFGE8, MIF, NOTCH1, NRP1, PRKCE, RORA, TLR3, SMAD2, TAL1, THY1, TNFSF12, TRAF6, TXNIP, VEGFA, S100A8, and/or WDR83OS.

In embodiments, the proteins are selected from CCL2, CCL3, CCL7, CD300E, CD93, CSF3, CXCL1, CXCL2, CXCL3, CXCL5, CXCL8, ECEL1, HAS1, IL-1β, IL8, IL23, INHBA, PADI2, PID1, PTGS2, SCL747, SERPINB2, ST6GALNAC2, and/or THBS1. In embodiments, proteins are selected from CXCL1, CXCL2, CXCL3, CXCL5, SERPINB2, IL8, and/or IL-1β. In embodiments, genes are selected from IL1β, PTGS2, CXCL1, CXCL2, CXCL3, CXCL5, CXCL6, and CXCL8. In embodiments, the proteins are selected from EHF, FUT7, and/or OST4. In embodiments, expression of other proteins is not detected. In embodiments, the method further comprises: (c) comparing the level of expression of the one or more proteins in the sample to a level of expression of the one or more proteins in a suitable control.

In embodiments is provided a method for detecting a level of expression of one or more proteins in a subject having or suspected of having cancer, the method comprising: (a) obtaining a biological sample from the subject; and (b) detecting the level of expression of the one or more proteins in the biological sample, wherein the proteins are selected from CD68, CD163, LBP, CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18; wherein a level of expression of the one or more proteins that is higher than a control indicates that the subject is a candidate for treatment with an adenosine pathway inhibitor (e.g., ADORA2A antagonist).

In embodiments is provided a method for detecting a level of expression of one or more proteins in a subject having or suspected of having cancer, the method comprising: (a) obtaining a biological sample from the subject; and (b) detecting the level of expression of the one or more proteins in the biological sample, wherein the proteins are selected from CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1B, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18; wherein a level of expression of the one or more proteins that is higher than a control indicates that the subject is a candidate for treatment with an adenosine pathway inhibitor (e.g., ADORA2A antagonist).

In embodiments, the proteins are selected from CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, and/or THBS1. In embodiments, the proteins are selected from BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18. In embodiments, the proteins are selected from CCL2, CCL3, CCL7, CD300E, CD93, CSF3, CXCL1, CXCL2, CXCL3, CXCL5, CXCL8, ECEL1, HAS1, IL-1β, IL8, IL23, INHBA, PADI2, PID1, PTGS2, SCL747, SERPINB2, ST6GALNAC2, and/or THBS1. In embodiments, proteins are selected from CXCL1, CXCL2, CXCL3, CXCL5, SERPINB2, IL8, and/or IL-1β. In embodiments, genes are selected from IL1β, PTGS2, CXCL1, CXCL2, CXCL3, CXCL5, CXCL6, and CXCL8. In embodiments, expression of other proteins is not detected.

In embodiments is provided a method for detecting a level of expression of one or more proteins in a subject having or suspected of having cancer, the method comprising: (a) obtaining a biological sample from the subject; and (b) detecting the level of expression of the one or more proteins in the biological sample, wherein the proteins are selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA; wherein a level of expression of the one or more proteins that is lower than a control indicates that the subject is a candidate for treatment with an adenosine pathway inhibitor (e.g., ADORA2A antagonist). In embodiments, the proteins are selected from AKT3, BMI1, CD164, CD34, CD36, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, VEGFA, APP, ATG10, BCL2, CCL15, CD24, CD46, CD59, CDH1, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, MIF, PPARG, RORA, RORC, SPA17, STAT5B, TLR3, and/or TOLLIP. In embodiments, the proteins are selected from CCL24, CCNE1, EHF, FUT7, GALM, GBP6, IL5, LAP3, MRPL11, OST4, WDR83OS, and/or TBX21. In embodiments, the proteins are selected from EHF, FUT7, and/or OST4. In embodiments, expression of other proteins is not detected.

In embodiments is provided a method of identifying a subject for treatment with an adenosine pathway inhibitor (e.g., ADORA2A antagonist), said subject having or suspected of having cancer, the method comprising: (a) obtaining a biological sample from the subject; and (b) detecting a level of expression of one or more proteins in the biological sample, wherein the proteins are selected from CD68, CD163, LBP, CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, CXCR1, CXCR2, DMBT1, FOXJ1, ITCH, MAP2K2, PRAME, PSMD7, and/or TNFSF18; wherein a level of expression of the one or more proteins that is higher than a control indicates that the subject is a candidate for treatment with the adenosine pathway inhibitor (e.g., ADORA2A antagonist).

In embodiments is provided a method of identifying a subject for treatment with an adenosine pathway inhibitor (e.g., ADORA2A antagonist), said subject having or suspected of having cancer, the method comprising: (a) obtaining a biological sample from the subject; and (b) detecting a level of expression of one or more proteins in the biological sample, wherein the proteins are selected from CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18; wherein a level of expression of the one or more proteins that is higher than a control indicates that the subject is a candidate for treatment with the adenosine pathway inhibitor (e.g., ADORA2A antagonist).

In embodiments is provided a method of identifying a subject for treatment with an adenosine pathway inhibitor (e.g., ADORA2A antagonist), said subject having or suspected of having cancer, the method comprising: (a) obtaining a biological sample from the subject; and (b) detecting a level of expression of one or more proteins in the biological sample, wherein the proteins are selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA; wherein a level of expression of the one or more proteins that is lower than a control indicates that the subject is a candidate for treatment with the adenosine pathway inhibitor (e.g., ADORA2A antagonist).

In embodiments is provided a method of treating a subject having cancer, the method comprising: (a) obtaining a biological sample from the subject; (b) detecting a level of expression of one or more proteins in the biological sample, wherein the proteins are selected from CD68, CD163, LBP, CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18, wherein a level of expression of the one or more proteins that is higher than a control indicates that the subject is a candidate for treatment with an adenosine pathway inhibitor (e.g., ADORA2A antagonist); and (c) administering to the subject an effective amount of the adenosine pathway inhibitor (e.g., ADORA2A antagonist), thereby treating the cancer.

In embodiments is provided a method of treating a subject having cancer, the method comprising: (a) obtaining a biological sample from the subject; (b) detecting a level of expression of one or more proteins in the biological sample, wherein the proteins are selected from CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18, wherein a level of expression of the one or more proteins that is higher than a control indicates that the subject is a candidate for treatment with an adenosine pathway inhibitor (e.g., ADORA2A antagonist); and (c) administering to the subject an effective amount of the adenosine pathway inhibitor (e.g., ADORA2A antagonist), thereby treating the cancer.

In embodiments, the proteins are selected from CCL2, CCL3, CCL7, CD300E, CD93, CSF3, CXCL1, CXCL2, CXCL3, CXCL5, CXCL8, ECEL1, HAS1, IL-1β, IL8, IL23, INHBA, PADI2, PID1, PTGS2, SCL747, SERPINB2, ST6GALNAC2, and/or THBS1. In embodiments, expression of other proteins is not detected.

In embodiments is provided a method of treating a subject having cancer, the method comprising: (a) obtaining a biological sample from the subject; (b) detecting a level of expression of one or more proteins in the biological sample, wherein the proteins are selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA, wherein a level of expression of the one or more proteins that is lower than a control indicates that the subject is a candidate for treatment with an adenosine pathway inhibitor (e.g., ADORA2A antagonist); and (c) administering to the subject an effective amount of the adenosine pathway inhibitor (e.g., ADORA2A antagonist), thereby treating the cancer. In embodiments, the proteins are selected from EHF, FUT7, and/or OST4. In embodiments, expression of other proteins is not detected.

In embodiments is provided a method of treating a subject having cancer, the method comprising: (a) obtaining a biological sample from the subject; (b) receiving an identification of a patient as having an increased level of expression of one or more proteins selected from CD68, CD163, LBP, CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18 and/or a reduced level of expression of one or more proteins selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA in a biological sample; and (c) administering to the subject an effective amount of an adenosine pathway inhibitor (e.g., ADORA2A antagonist), thereby treating the cancer.

In embodiments is provided a method of treating a subject having cancer, the method comprising: (a) obtaining a biological sample from the subject; (b) receiving an identification of a patient as having an increased level of expression of one or more proteins selected from CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18 and/or a reduced level of expression of one or more proteins selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA in a biological sample; and (c) administering to the subject an effective amount of an adenosine pathway inhibitor (e.g., ADORA2A antagonist), thereby treating the cancer.

In an aspect is provided a method of treating a subject having cancer, the method comprising: (a) obtaining a biological sample from the subject; (b) detecting a level of expression of CD163 and/or CD68 in the sample; and (c) administering to the subject an effective amount of an adenosine pathway inhibitor (e.g., ADORA2A antagonist), thereby treating the cancer. In embodiments, a level of CD163 and/or CD68 gene expression is detected. In embodiments, a level of CD163 and/or CD68 protein expression is detected. In embodiments, a level of expression of at least one additional gene and/or protein is detected. In embodiments, the at least one additional gene and/or protein is selected from LBP, BIRC5, BST1, CARD11, CCL2, CCL3, CCL7, CCL24, CCNE1, CD14, CD300E, CD86, CD93, CDK1, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, IL1A, IL-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, C1R, C1S, C4BPA, CCL11, CCL20, CXCL16, CXCL2, HAMP, HSD11B1, ITGAM, LIF, SAA1, TFRC, TLR5, TNFRSF11A, TNFSF14, TREM1, TREM2, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, TNFSF18, APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CD36, CDH1, CDH5, CREB1, DOCK9, ENG, HMGB1, ITGA1, JAM3, MAF, MAPK3, MAPK8, MCAM, MFGE8, MIF, NOTCH1, NRP1, PRKCE, RORA, TLR3, SMAD2, TAL1, THY1, TNFSF12, TRAF6, TXNIP, VEGFA, S100A8, and/or WDR83OS.

In an aspect is provided a method for detecting a level of expression of CD68 and/or CD163 in a subject having or suspected of having cancer, the method comprising: (a) obtaining a biological sample from the subject; and (b) detecting the level of expression of CD68 and/or CD163 in the biological sample. In embodiments, the method further comprises detecting a level of expression of one or more additional genes and/or proteins in the sample. In embodiments, the one or more additional genes and/or proteins are selected from CD68, CD163, BIRC5, BST1, CARD11, CCL2, CCL3, CCL7, CCL24, CCNE1, CD14, CD300E, CD86, CD93, CDK1, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, IL1A, IL-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, C1R, C1S, C4BPA, CCL11, CCL20, CXCL16, CXCL2, HAMP, HSD11B1, ITGAM, LIF, SAA1, TFRC, TLR5, TNFRSF11A, TNFSF14, TREM1, TREM2, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, LBP, MAP2K2, PRAME, PSMD7, TNFSF18, APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CD36, CDH1, CDH5, CREB1, DOCK9, ENG, HMGB1, ITGA1, JAM3, MAF, MAPK3, MAPK8, MCAM, MFGE8, MIF, NOTCH1, NRP1, PRKCE, RORA, TLR3, SMAD2, TAL1, THY1, TNFSF12, TRAF6, TXNIP, VEGFA, S100A8, and/or WDR83OS.

In an aspect is provided a method of identifying a subject for treatment with an adenosine pathway inhibitor, said subject having or suspected of having cancer, the method comprising: (a) obtaining a biological sample from the subject; and (b) detecting a level of expression of CD68 and/or CD163; wherein a level of expression of CD68 and/or CD163 that is higher than a suitable control indicates that the subject is a candidate for treatment with the adenosine pathway inhibitor.

In an aspect is provided a method of selecting a subject for treatment with an adenosine pathway inhibitor, said subject having or suspected of having cancer, the method comprising: (a) obtaining a biological sample from the subject; (b) detecting a high level of expression of CD68 and/or CD163; and (c) selecting the subject for treatment with the adenosine pathway inhibitor.

In embodiments, the adenosine pathway inhibitor is an ADORA2A antagonist. In embodiments, the ADORA2A antagonist is CPI-444. (chemical name: (S)-7-(5-methylfuran-2-yl)-3-((6-(((tetrahydrofuran-3-yl)oxy)methyl)pyridin-2-yl)methyl)-3H-[1,2,3]triazolo[4,5-d]pyrimidin-5-amine). See, e.g., WO/2017/112917, which is incorporated herein by reference in its entirety. In embodiments, the chemical structure of CPI-444 is:

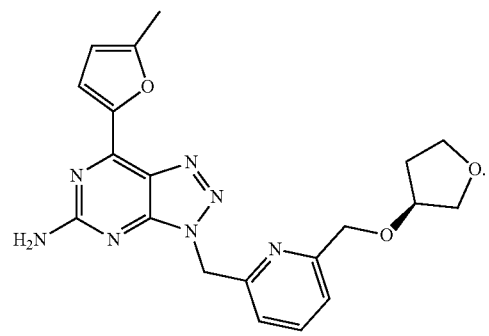 [SMILES: Cc1ccc(-c2nc(N)nc3c2nnn3Cc2cccc(CO[C@H]3CCOC3)n2)o1]

In embodiments, the ADORA2A antagonist is:

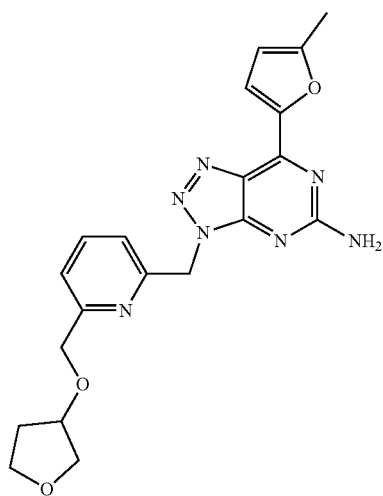 [SMILES: Cc1ccc(-c2nc(N)nc3c2nnn3Cc2cccc(COC3CCOC3)n2)o1]

In embodiments, a method as described herein further comprises administering a CXCR2 inhibitor to the subject. In embodiments, the CXCR2 inhibitor is selected from AZD5069 (AstraZeneca), Reparixin (Dompé Farmaceutici), Danirixin (GSK), Ladarixin (Dompé Farmaceutici), QBM076 (Novartis), SX-682 (Syntrix Biosystems), anti-CXCR2 antibody, Navarixin (MK-7123; Ligand Pharmaceuticals/Merck & Co.).

BRIEF DESCRIPTION OF THE DRAWINGS

FIG. 2A shows the treatment regimen for healthy human PBMCs treated with NECA, with or without CPI-444, and activated by anti-CD3/CD28 antibody. Expression of CXCL5 was determined by ELISA 2 days after activation.

FIGS. 2B and 2C show the response of PBMCs from two different donors to NECA+/−CPI-444 treatment. DMSO was used as vehicle control. The blue bars depict a dose-dependent increase in CXCL5 (measured by ELISA) in the culture supernatants of human PBMCs stimulated with NECA. The red bars show that this increase in CXCL5 can be blocked by the addition of CPI-444, a A2AR receptor antagonist that neutralizes the immunosuppressive effects of NECA (adenosine). This control helps establish that the induction of CXCL5 is specific to signaling through adenosine receptors.

FIGS. 3A and 3B show the correlation of mean log 2 expression of genes in the adenosine composite gene expression module (CXCL1, CXCL2, CXCL3, CXCL5, SERPINB2, IL8, and IL1B) (X axis) with CCL20 gene expression (Y axis) in a variety of cancer types, as determined using the TCGA database. For all tumor types tested, p<0.0001.

DETAILED DESCRIPTION

I. Definitions

Figure 1:
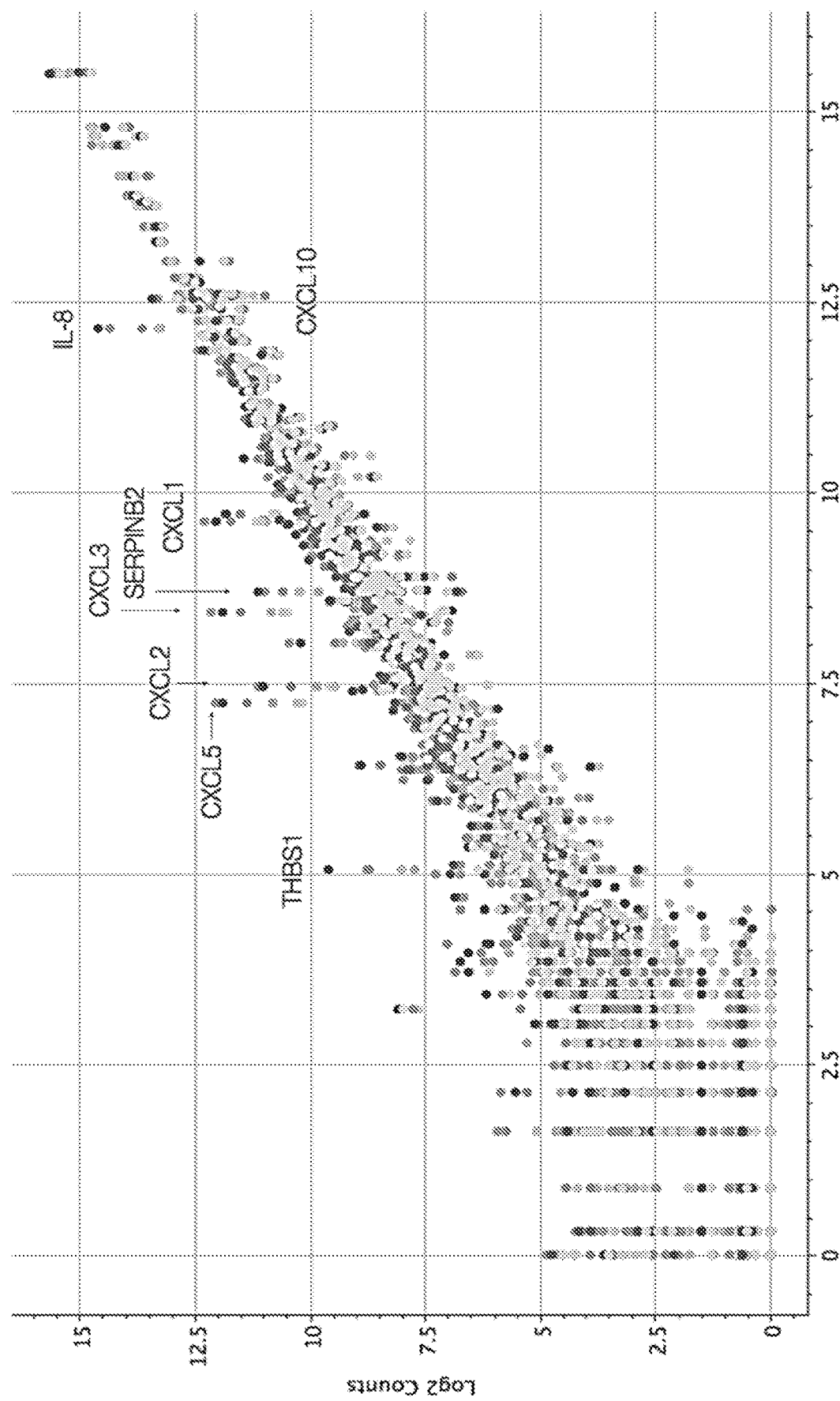
FIG. 1 is a representation of genes whose expression is modulated by NECA treatment in healthy human PBMCs. Each dot represents the expression level of a specific gene. Dot shade represents the concentration of NECA used and/or different PBMC donors. Genes above the diagonal axis are upregulated relative to the DMSO control. Genes below the diagonal axis are downregulated relative to the DMSO control. Labeled genes represent a subset of genes that are consistently regulated by NECA treatment.

The terms "a" or "an," as used in herein means one or more.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

As used herein, the term "cancer" refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer. In embodiments, the cancer or tumor type is adrenalcortical cancer, bladder/urothelial cancer, breast cancer, cervical cancer, cholangiocarcinoma, colorectal adenocarcinoma, diffuse large B-cell lymphoma, glioma, head and neck squamous cell carcinoma, renal cancer, renal clear cell cancer, papillary cell cancer, hepatocellular cancer, lung cancer, mesothelioma, ovarian cancer, pancreatic cancer, pheochromocytoma, paraganglioma, prostate cancer, rectal cancer, sarcoma, melanoma, stomach or esophageal cancer, testicular cancer, thyroid cancer, thymoma, uterine cancer, and/or uveal melanoma.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cutaneous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma *villosum*.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is not prophylactic treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount", as used herein, is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). In these methods, the effective amount of the adenosine pathway inhibitor is an amount effective to accomplish the stated purpose of the method. An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Control," "suitable control," or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples). For example, a test sample can be taken from a patient suspected of having a given disease (cancer) and compared to samples from a known cancer patient, or a known normal (non-disease) individual. A control can also represent an average value gathered from a population of similar individuals, e.g., cancer patients or healthy individuals with a similar medical background, same age, weight, etc. A control value can also be obtained from the same individual, e.g., from an earlier-obtained sample, prior to disease, or prior to treatment. One of skill will recognize that controls can be designed for assessment of any number of parameters. In embodiments, a control is a negative control. In embodiments, such as some embodiments relating to detecting the level of expression of a gene/protein or a subset of genes/proteins, a control comprises the average amount of expression (e.g., protein or mRNA) in a population of subjects (e.g., with cancer) or in a healthy or general population. In embodiments, the control comprises an average amount (e.g. amount of expression) in a population in which the number of subjects (n) is 5 or more, 6 or more, 7 or more, 8 or more, 9 or more, 10 or more, 25 of more, 50 or more, 100 or more, 1000 or more, 5000 or more, or 10000 or more. In embodiments, the control is a standard control. In embodiments, the control is a population of cancer subjects. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

As defined herein, the term "inhibition", "inhibit", "inhibiting" and the like in reference to a protein-inhibitor interaction (e.g. pathway inhibition) means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation). An "ADORA2A antagonist" is a compound that negatively affects (e.g. decreases) the activity or function of ADORA2A relative to the activity or function of ADORA2A in the absence of the inhibitor.

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

"Adenosine pathway inhibitor" refers to a molecule that inhibits the activity of the adenosine pathway. An adenosine pathway inhibitor may be, without limitation, an adenosine receptor (e.g., adenosine 2A receptor or adenosine 2B receptor) antagonist, a CD73 antagonist, a CD38 antagonist, a CD39 antagonist, or adenosine deaminase. Examples of CD73 antagonists can be found in PCT Pub. Nos. WO 2017/100670 and WO 2018/013611; and PCT Application No. PCT/US18/26142; each of which is incorporated herein by reference in its entirety.

"Adenosine receptor antagonist" refers to a molecule that inhibits activity of adenosine receptors (e.g. A2A or A2B receptors), typically through direct action. Adenosine receptors antagonists can be small or large molecule antagonists. In embodiments, CPI-444 is an example A2A receptor antagonist. CPI-444 is a selective A2AR antagonist that has demonstrated anti-tumor activity as a monotherapy in an ongoing phase 1/1b trial in patients with advanced cancers. CPI-444 is described, for example, in PCT Patent Publication No. WO 2017/112917; each of which is incorporated herein by reference in its entirety.

The term "A2A adenosine receptor" as provided herein includes any of the recombinant or naturally-occurring forms of the A2A adenosine receptor (ADORA2A) or variants or homologs thereof that maintain ADORA2A protein activity (e.g. within at least 50%, 80%, 90%, 95%, 96%, 97%, 98%, 99% or 100% activity compared to ADORA2A). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ADORA2A polypeptide. In embodiments, ADORA2A is the protein as identified by the NCBI sequence reference GI: 5921992, homolog or functional fragment thereof.

The term "expression" or "expresses" includes any step involved in the production of the polypeptide including, but not limited to, transcription, post-transcriptional modification, translation, post-translational modification, and secretion. Expression ("level of expression") can be detected using conventional techniques for detecting protein (e.g., ELISA, Western blotting, flow cytometry, immunofluorescence, immunohistochemistry, etc.).

II. Biomarkers

Extracellular adenosine in the tumor microenvironment generates an immunosuppressive niche that promotes tumor growth and metastasis by signaling through adenosine receptors, e.g., the A2A receptor (A2AR), on immune cells. Without being bound by theory, it is believed that patients with tumors having high levels of adenosine in the tumor microenvironment are good candidates for treatment with an adenosine pathway inhibitor (e.g., ADORA2A antagonist). In embodiments, this disclosure relates to methods of determining whether the cancer is expected to be susceptible to treatment with an adenosine pathway inhibitor by determining the level of expression of a gene or protein, or a subset of genes or proteins, in a tumor or a subject having a cancer by measuring the expression of the gene/protein or subset of genes/proteins in the tumor or subject.

In an embodiment, determining the level of expression of the one or more genes includes calculating the mean of Log2 of the expression of the one or more genes in a biological sample. In one embodiment, gene expression is determined by Nanostring counts. In one embodiment, gene expression is determined by number of transcripts detected in the sample. One skilled in the art could use other methods for quantifying gene expression (e.g., mRNA levels), such as RNAseq or quantitative PCR.

In one embodiment, determining the level of expression of the one or more proteins includes calculating the mean of Log2 of the amount of the one or more proteins in a biological sample. The resulting value can then be compared to other values obtained in the same manner (e.g., based on level of the same proteins in a control). In one embodiment, protein level is determined by high-performance liquid chromatography (HPLC); mass spectrometry (MS), e.g., Liquid chromatography-mass spectrometry; Enzyme-linked immunosorbent assay (ELISA); Protein immunoprecipitation; immunoelectrophoresis; Western blot; protein immunostaining; immunofluorescence; or mass cytometry.

In embodiments, the genes or proteins measured include CXCL1, CXCL2, CXCL3, CXCL5, SERPINB2, IL8, and IL1B.

Table 1 includes a list of genes (or proteins) that are down-regulated by adenosine (adenosine pathway) and may be detected using the methods described herein. In embodiments, expression of any combination of genes listed in Table 1 is negatively correlated with high adenosine levels in a tumor or tumor microenvironment. In embodiments, the gene(s) or protein(s) of Table 1 are down-regulated in a cell in the presence of adenosine. In embodiments, a level of expression in a subject or tumor of any combination of the genes/proteins of Table 1 that is lower than a control indicates that the tumor can be treated with an adenosine pathway inhibitor. The level of expression of any combination of one or more, two or more, three or more, and so on, of the genes (or proteins) in Table 1 may be determined. In embodiments, any one or more of the genes (or proteins) in Table 1 may be excluded.

In embodiments, the level of expression of at least one gene from Table 1 is determined. In embodiments, the expression of at least two genes from Table 1 is determined. In embodiments, the expression of at least 3 genes from Table 1 is determined. In embodiments, the expression of at least 4 genes from Table 1 is determined. In embodiments, the expression of at least 5 genes from Table 1 is determined. In embodiments, the expression of at least 6 genes from Table 1 is determined. In embodiments, the expression of at least 7 genes from Table 1 is determined. In embodiments, the expression of at least 8 genes from Table 1 is determined. In embodiments, the expression of at least 9 genes from Table 1 is determined. In embodiments, the expression of at least 10 genes from Table 1 is determined. In embodiments, the expression of at least 11 genes from Table 1 is determined. In embodiments, the expression of at least 12 genes from Table 1 is determined. In embodiments, the expression of at least 13 genes from Table 1 is determined. In embodiments, the expression of at least 14 genes from Table 1 is determined. In embodiments, the expression of at least 15 genes from Table 1 is determined. In embodiments, the expression of at least 16 genes from Table 1 is determined. In embodiments, the expression of at least 17 genes from Table 1 is determined. In embodiments, the expression of at least 18 genes from Table 1 is determined. In embodiments, the expression of at least 19 genes from Table 1 is determined. In embodiments, the expression of at least 20 genes from Table 1 is determined. In embodiments, the expression of at least 21 genes from Table 1 is determined. In embodiments, the expression of at least 22 genes from Table 1 is determined. In embodiments, the expression of at least 23 genes from Table 1 is determined. In embodiments, the expression of at least 24 genes from Table 1 is determined. In embodiments, the expression of at least 25 genes from Table 1 is determined. In embodiments, the expression of at least 26 genes from Table 1 is determined. In embodiments, the expression of at least 27 genes from Table 1 is determined. In embodiments, the expression of at least 28 genes from Table 1 is determined. In embodiments, the expression of at least 29 genes from Table 1 is determined. In embodiments, the expression of at least 30 genes from Table 1 is determined. In embodiments, the expression of at least 35 genes from Table 1 is determined. In embodiments, the expression of at least 40 genes from Table 1 is determined. In embodiments, the expression of at least 45 genes from Table 1 is determined. In embodiments, the expression of at least 50 genes from Table 1 is determined. In embodiments, the expression of at least 55 genes from Table 1 is determined. In embodiments, the expression of at least 60 genes from Table 1 is determined. In embodiments, the expression of at least 65 genes from Table 1 is determined.

In embodiments, the level of expression of one gene from Table 1 is determined. In embodiments, the expression of two genes from Table 1 is determined. In embodiments, the expression of 3 genes from Table 1 is determined. In embodiments, the expression of 4 genes from Table 1 is determined. In embodiments, the expression of 5 genes from Table 1 is determined. In embodiments, the expression of 6 genes from Table 1 is determined. In embodiments, the expression of 7 genes from Table 1 is determined. In embodiments, the expression of 8 genes from Table 1 is determined. In embodiments, the expression of 9 genes from Table 1 is determined. In embodiments, the expression of 10 genes from Table 1 is determined. In embodiments, the expression of 11 genes from Table 1 is determined. In embodiments, the expression of 12 genes from Table 1 is determined. In embodiments, the expression of 13 genes from Table 1 is determined. In embodiments, the expression of 14 genes from Table 1 is determined. In embodiments, the expression of 15 genes from Table 1 is determined. In embodiments, the expression of 16 genes from Table 1 is determined. In embodiments, the expression of 17 genes from Table 1 is determined. In embodiments, the expression of 18 genes from Table 1 is determined. In embodiments, the expression of 19 genes from Table 1 is determined. In embodiments, the expression of 20 genes from Table 1 is determined. In embodiments, the expression of 21 genes from Table 1 is determined. In embodiments, the expression of 22 genes from Table 1 is determined. In embodiments, the expression of 23 genes from Table 1 is determined. In embodiments, the expression of 24 genes from Table 1 is determined. In embodiments, the expression of 25 genes from Table 1 is determined. In embodiments, the expression of 26 genes from Table 1 is determined. In embodiments, the expression of 27 genes from Table 1 is determined. In embodiments, the expression of 28 genes from Table 1 is determined. In embodiments, the expression of 29 genes from Table 1 is determined. In embodiments, the expression of 30 genes from Table 1 is determined. In embodiments, the expression of 31 genes from Table 1 is determined. In embodiments, the expression of 32 genes from Table 1 is determined. In embodiments, the expression of 33 genes from Table 1 is determined. In embodiments, the expression of 34 genes from Table 1 is determined. In embodiments, the expression of 35 genes from Table 1 is determined. In embodiments, the expression of 36 genes from Table 1 is determined. In embodiments, the expression of 37 genes from Table 1 is determined. In embodiments, the expression of 38 genes from Table 1 is determined. In embodiments, the expression of 39 genes from Table 1 is determined. In embodiments, the expression of 40 genes from Table 1 is determined. In embodiments, the expression of 41 genes from Table 1 is determined. In embodiments, the expression of 42 genes from Table 1 is determined. In embodiments, the expression of 43 genes from Table 1 is determined. In embodiments, the expression of 44 genes from Table 1 is determined. In embodiments, the expression of 45 genes from Table 1 is determined. In embodiments, the expression of 46 genes from Table 1 is determined. In embodiments, the expression of 47 genes from Table 1 is determined. In embodiments, the expression of 48 genes from Table 1 is determined. In embodiments, the expression of 49 genes from Table 1 is determined. In embodiments, the expression of 50 genes from Table 1 is determined. In embodiments, the expression of 51 genes from Table 1 is determined. In embodiments, the expression of 52 genes from Table 1 is determined. In embodiments, the expression of 53 genes from Table 1 is determined. In embodiments, the expression of 54 genes from Table 1 is determined. In embodiments, the expression of 55 genes from Table 1 is determined. In embodiments, the expression of 56 genes from Table 1 is determined. In embodiments, the expression of 57 genes from Table 1 is determined. In embodiments, the expression of 58 genes from Table 1 is determined. In embodiments, the expression of 59 genes from Table 1 is determined. In embodiments, the expression of 60 genes from Table 1 is determined. In embodiments, the expression of 61 genes from Table 1 is determined. In embodiments, the expression of 62 genes from Table 1 is determined. In embodiments, the expression of 63 genes from Table 1 is determined. In embodiments, the expression of 64 genes from Table 1 is determined. In embodiments, the expression of 65 genes from Table 1 is determined. In embodiments, the expression of 66 genes from Table 1 is determined. In embodiments, the expression of 67 genes from Table 1 is determined.

Table 2 includes a list of genes (or proteins) that are up-regulated by adenosine (adenosine pathway) and may be detected using the methods described herein. In embodiments, expression of any combination of genes listed in Table 2 is positively correlated with high adenosine levels in a tumor or tumor microenvironment. In embodiments, the gene(s) or protein(s) of Table 2 are up-regulated in a cell in the presence of adenosine. In embodiments, a level of expression in a subject or tumor of any combination of the genes/proteins of Table 2 that is higher than a control indicates that the tumor can be treated with an adenosine pathway inhibitor. The level of expression of any combination of one or more, two or more, three or more, and so on, of the genes (or proteins) in Table 2 may be determined. In an embodiment, a subject having a low level of any one or more of these genes/proteins (compared to a control) is administered an adenosine pathway inhibitor. In embodiments, any one or more of the genes (or proteins) in Table 2 may be excluded.

Tables 7, 8, and 9 include lists of genes (or proteins) that have expression patterns in various cancer types that correlate with expression patterns of genes known to be up-regulated by adenosine (adenosine pathway) and may be detected using the methods described herein. In embodiments, expression of any combination of genes listed in Tables 7, 8, and/or 9 is positively correlated with high adenosine levels in a tumor or tumor microenvironment. In embodiments, the gene(s) or protein(s) of Tables 7, 8, and/or 9 are up-regulated in a cell in the presence of adenosine. In embodiments, a level of expression in a subject or tumor of any combination of the genes/proteins of Tables 7, 8, and/or 9 that is higher than a control indicates that the tumor can be treated with an adenosine pathway inhibitor. The level of expression of any combination of one or more, two or more, three or more, and so on, of the genes (or proteins) in Tables 7, 8, and/or 9 may be determined. In an embodiment, a subject having a low level of any one or more of these genes/proteins (compared to a control) is administered an adenosine pathway inhibitor. In embodiments, any one or more of the genes (or proteins) in Tables 7, 8, and/or 9 may be excluded.

In embodiments, the level of at least one protein and at least one gene are determined. The gene and protein expression levels may be determined from the same biological sample or from different biological samples. In embodiments, the level of expression of at least one protein from Table 1 and the level of expression of at least one gene from Table 1 are determined. In embodiments, the level of expression of at least one protein from Table 2 and the level of expression of at least one gene from Table 2 are determined. In embodiments, the level of expression of at least one protein from Table 7 and the level of expression of at least one gene from Table 7 are determined. In embodiments, the level of expression of at least one protein from Table 8 and the level of expression of at least one gene from Table 8 are determined. In embodiments, the level of expression of at least one protein from Table 9 and the level of expression of at least one gene from Table 9 are determined.

In embodiments, the level of expression of at least one gene from Table 2 is determined. In embodiments, the expression of at least two genes from Table 2 is determined. In embodiments, the expression of at least 3 genes from Table 2 is determined. In embodiments, the expression of at least 4 genes from Table 2 is determined. In embodiments, the expression of at least 5 genes from Table 2 is determined. In embodiments, the expression of at least 6 genes from Table 2 is determined. In embodiments, the expression of at least 7 genes from Table 2 is determined. In embodiments, the expression of at least 8 genes from Table 2 is determined. In embodiments, the expression of at least 9 genes from Table 2 is determined. In embodiments, the expression of at least 10 genes from Table 2 is determined. In embodiments, the expression of at least 11 genes from Table 2 is determined. In embodiments, the expression of at least 12 genes from Table 2 is determined. In embodiments, the expression of at least 13 genes from Table 2 is determined. In embodiments, the expression of at least 14 genes from Table 2 is determined. In embodiments, the expression of at least 15 genes from Table 2 is determined. In embodiments, the expression of at least 16 genes from Table 2 is determined. In embodiments, the expression of at least 17 genes from Table 2 is determined. In embodiments, the expression of at least 18 genes from Table 2 is determined. In embodiments, the expression of at least 19 genes from Table 2 is determined. In embodiments, the expression of at least 20 genes from Table 2 is determined. In embodiments, the expression of at least 21 genes from Table 2 is determined. In embodiments, the expression of at least 22 genes from Table 2 is determined. In embodiments, the expression of at least 23 genes from Table 2 is determined. In embodiments, the expression of at least 24 genes from Table 2 is determined. In embodiments, the expression of at least 25 genes from Table 2 is determined. In embodiments, the expression of at least 26 genes from Table 2 is determined. In embodiments, the expression of at least 27 genes from Table 2 is determined. In embodiments, the expression of at least 28 genes from Table 2 is determined. In embodiments, the expression of at least 29 genes from Table 2 is determined. In embodiments, the expression of at least 30 genes from Table 2 is determined. In embodiments, the expression of at least 35 genes from Table 2 is determined. In embodiments, the expression of at least 40 genes from Table 2 is determined. In embodiments, the expression of at least 45 genes from Table 2 is determined. In embodiments, the expression of at least 50 genes from Table 2 is determined. In embodiments, the expression of at least 55 genes from Table 2 is determined. In embodiments, the expression of at least 60 genes from Table 2 is determined. In embodiments, the expression of at least 65 genes from Table 2 is determined. In embodiments, the expression of at least 70 genes from Table 2 is determined. In embodiments, the expression of at least 75 genes from Table 2 is determined. In embodiments, the expression of at least 80 genes from Table 2 is determined. In embodiments, the expression of at least 85 genes from Table 2 is determined. In embodiments, the expression of at least 90 genes from Table 2 is determined. In embodiments, the expression of at least 95 genes from Table 2 is determined. In embodiments, the expression of at least 100 genes from Table 2 is determined. In an embodiment, a subject having a high level of any one or more of these genes/proteins (compared to a control) is administered an adenosine pathway inhibitor.

In embodiments, the level of expression of one gene from Table 2 is determined. In embodiments, the expression of two genes from Table 2 is determined. In embodiments, the expression of 3 genes from Table 2 is determined. In embodiments, the expression of 4 genes from Table 2 is determined. In embodiments, the expression of 5 genes from Table 2 is determined. In embodiments, the expression of 6 genes from Table 2 is determined. In embodiments, the expression of 7 genes from Table 2 is determined. In embodiments, the expression of 8 genes from Table 2 is determined. In embodiments, the expression of 9 genes from Table 2 is determined. In embodiments, the expression of 10 genes from Table 2 is determined. In embodiments, the expression of 11 genes from Table 2 is determined. In embodiments, the expression of 12 genes from Table 2 is determined. In embodiments, the expression of 13 genes from Table 2 is determined. In embodiments, the expression of 14 genes from Table 2 is determined. In embodiments, the expression of 15 genes from Table 2 is determined. In embodiments, the expression of 16 genes from Table 2 is determined. In embodiments, the expression of 17 genes from Table 2 is determined. In embodiments, the expression of 18 genes from Table 2 is determined. In embodiments, the expression of 19 genes from Table 2 is determined. In embodiments, the expression of 20 genes from Table 2 is determined. In embodiments, the expression of 21 genes from Table 2 is determined. In embodiments, the expression of 22 genes from Table 2 is determined. In embodiments, the expression of 23 genes from Table 2 is determined. In embodiments, the expression of 24 genes from Table 2 is determined. In embodiments, the expression of 25 genes from Table 2 is determined. In embodiments, the expression of 26 genes from Table 2 is determined. In embodiments, the expression of 27 genes from Table 2 is determined. In embodiments, the expression of 28 genes from Table 2 is determined. In embodiments, the expression of 29 genes from Table 2 is determined. In embodiments, the expression of 30 genes from Table 2 is determined. In embodiments, the expression of 31 genes from Table 2 is determined. In embodiments, the expression of 32 genes from Table 2 is determined. In embodiments, the expression of 33 genes from Table 2 is determined. In embodiments, the expression of 34 genes from Table 2 is determined. In embodiments, the expression of 35 genes from Table 2 is determined. In embodiments, the expression of 36 genes from Table 2 is determined. In embodiments, the expression of 37 genes from Table 2 is determined. In embodiments, the expression of 38 genes from Table 2 is determined. In embodiments, the expression of 39 genes from Table 2 is determined. In embodiments, the expression of 40 genes from Table 2 is determined. In embodiments, the expression of 41 genes from Table 2 is determined. In embodiments, the expression of 42 genes from Table 2 is determined. In embodiments, the expression of 43 genes from Table 2 is determined. In embodiments, the expression of 44 genes from Table 2 is determined. In embodiments, the expression of 45 genes from Table 2 is determined. In embodiments, the expression of 46 genes from Table 2 is determined. In embodiments, the expression of 47 genes from Table 2 is determined. In embodiments, the expression of 48 genes from Table 2 is determined. In embodiments, the expression of 49 genes from Table 2 is determined. In embodiments, the expression of 50 genes from Table 2 is determined. In embodiments, the expression of 51 genes from Table 2 is determined. In embodiments, the expression of 52 genes from Table 2 is determined. In embodiments, the expression of 53 genes from Table 2 is determined. In embodiments, the expression of 54 genes from Table 2 is determined. In embodiments, the expression of 55 genes from Table 2 is determined. In embodiments, the expression of 56 genes from Table 2 is determined. In embodiments, the expression of 57 genes from Table 2 is determined. In embodiments, the expression of 58 genes from Table 2 is determined. In embodiments, the expression of 59 genes from Table 2 is determined. In embodiments, the expression of 60 genes from Table 2 is determined. In embodiments, the expression of 61 genes from Table 2 is determined. In embodiments, the expression of 62 genes from Table 2 is determined. In embodiments, the expression of 63 genes from Table 2 is determined. In embodiments, the expression of 64 genes from Table 2 is determined. In embodiments, the expression of 65 genes from Table 2 is determined. In embodiments, the expression of 66 genes from Table 2 is determined. In embodiments, the expression of 67 genes from Table 2 is determined. In embodiments, the expression of 68 genes from Table 2 is determined. In embodiments, the expression of 69 genes from Table 2 is determined. In embodiments, the expression of 70 genes from Table 2 is determined. In embodiments, the expression of 71 genes from Table 2 is determined. In embodiments, the expression of 72 genes from Table 2 is determined. In embodiments, the expression of 73 genes from Table 2 is determined. In embodiments, the expression of 74 genes from Table 2 is determined. In embodiments, the expression of 75 genes from Table 2 is determined. In embodiments, the expression of 76 genes from Table 2 is determined. In embodiments, the expression of 77 genes from Table 2 is determined. In embodiments, the expression of 78 genes from Table 2 is determined. In embodiments, the expression of 79 genes from Table 2 is determined. In embodiments, the expression of 80 genes from Table 2 is determined. In embodiments, the expression of 81 genes from Table 2 is determined. In embodiments, the expression of 82 genes from Table 2 is determined. In embodiments, the expression of 83 genes from Table 2 is determined. In embodiments, the expression of 84 genes from Table 2 is determined. In embodiments, the expression of 85 genes from Table 2 is determined. In embodiments, the expression of 86 genes from Table 2 is determined. In embodiments, the expression of 87 genes from Table 2 is determined. In embodiments, the expression of 88 genes from Table 2 is determined. In embodiments, the expression of 89 genes from Table 2 is determined. In embodiments, the expression of 90 genes from Table 2 is determined. In embodiments, the expression of 91 genes from Table 2 is determined. In embodiments, the expression of 92 genes from Table 2 is determined. In embodiments, the expression of 93 genes from Table 2 is determined. In embodiments, the expression of 94 genes from Table 2 is determined. In embodiments, the expression of 95 genes from Table 2 is determined. In embodiments, the expression of 96 genes from Table 2 is determined. In embodiments, the expression of 97 genes from Table 2 is determined. In embodiments, the expression of 98 genes from Table 2 is determined. In embodiments, the expression of 99 genes from Table 2 is determined. In embodiments, the expression of 100 genes from Table 2 is determined. In embodiments, the expression of 101 genes from Table 2 is determined. In embodiments, the expression of 102 genes from Table 2 is determined. In embodiments, the expression of 103 genes from Table 2 is determined. In embodiments, the expression of 104 genes from Table 2 is determined. In embodiments, the expression of 105 genes from Table 2 is determined. In embodiments, the expression of 106 genes from Table 2 is determined. In embodiments, the expression of 107 genes from Table 2 is determined. In embodiments, the expression of 108 genes from Table 2 is determined. In embodiments, the expression of 109 genes from Table 2 is determined.

In embodiments, the level of expression of at least one gene from Table 7 is determined. In embodiments, the expression of at least two genes from Table 7 is determined. In embodiments, the expression of at least 3 genes from Table 7 is determined. In embodiments, the expression of at least 4 genes from Table 7 is determined. In embodiments, the expression of at least 5 genes from Table 7 is determined. In embodiments, the expression of at least 6 genes from Table 7 is determined. In embodiments, the expression of at least 7 genes from Table 7 is determined. In embodiments, the expression of at least 8 genes from Table 7 is determined. In embodiments, the expression of at least 9 genes from Table 7 is determined. In embodiments, the expression of at least 10 genes from Table 7 is determined. In embodiments, the expression of at least 11 genes from Table 7 is determined. In embodiments, the expression of at least 12 genes from Table 7 is determined. In embodiments, the expression of at least 13 genes from Table 7 is determined. In embodiments, the expression of at least 14 genes from Table 7 is determined. In embodiments, the expression of at least 15 genes from Table 7 is determined. In embodiments, the expression of at least 16 genes from Table 7 is determined. In embodiments, the expression of at least 17 genes from Table 7 is determined. In embodiments, the expression of at least 18 genes from Table 7 is determined. In embodiments, the expression of at least 19 genes from Table 7 is determined. In embodiments, the expression of at least 20 genes from Table 7 is determined. In embodiments, the expression of at least 21 genes from Table 7 is determined. In embodiments, the expression of at least 22 genes from Table 7 is determined. In embodiments, the expression of at least 23 genes from Table 7 is determined. In embodiments, the expression of at least 24 genes from Table 7 is determined. In embodiments, the expression of at least 25 genes from Table 7 is determined. In embodiments, the expression of at least 26 genes from Table 7 is determined. In embodiments, the expression of at least 27 genes from Table 7 is determined. In embodiments, the expression of at least 28 genes from Table 7 is determined. In embodiments, the expression of at least 29 genes from Table 7 is determined. In embodiments, the expression of at least 30 genes from Table 7 is determined. In embodiments, the expression of at least 35 genes from Table 7 is determined. In embodiments, the expression of at least 40 genes from Table 7 is determined. In embodiments, the expression of at least 45 genes from Table 7 is determined. In embodiments, the expression of at least 50 genes from Table 7 is determined. In embodiments, the expression of at least 55 genes from Table 7 is determined. In embodiments, the expression of at least 60 genes from Table 7 is determined. In embodiments, the expression of at least 65 genes from Table 7 is determined. In embodiments, the expression of at least 70 genes from Table 7 is determined. In embodiments, the expression of at least 75 genes from Table 7 is determined. In embodiments, the expression of at least 80 genes from Table 7 is determined. In embodiments, the expression of at least 85 genes from Table 7 is determined. In embodiments, the expression of at least 90 genes from Table 7 is determined. In an embodiment, a subject having a high level of any one or more of these genes/proteins (compared to a control) is administered an adenosine pathway inhibitor.

In embodiments, the level of expression of one gene from Table 7 is determined. In embodiments, the expression of two genes from Table 7 is determined. In embodiments, the expression of 3 genes from Table 7 is determined. In embodiments, the expression of 4 genes from Table 7 is determined. In embodiments, the expression of 5 genes from Table 7 is determined. In embodiments, the expression of 6 genes from Table 7 is determined. In embodiments, the expression of 7 genes from Table 7 is determined. In embodiments, the expression of 8 genes from Table 7 is determined. In embodiments, the expression of 9 genes from Table 7 is determined. In embodiments, the expression of 10 genes from Table 7 is determined. In embodiments, the expression of 11 genes from Table 7 is determined. In embodiments, the expression of 12 genes from Table 7 is determined. In embodiments, the expression of 13 genes from Table 7 is determined. In embodiments, the expression of 14 genes from Table 7 is determined. In embodiments, the expression of 15 genes from Table 7 is determined. In embodiments, the expression of 16 genes from Table 7 is determined. In embodiments, the expression of 17 genes from Table 7 is determined. In embodiments, the expression of 18 genes from Table 7 is determined. In embodiments, the expression of 19 genes from Table 7 is determined. In embodiments, the expression of 20 genes from Table 7 is determined. In embodiments, the expression of 21 genes from Table 7 is determined. In embodiments, the expression of 22 genes from Table 7 is determined. In embodiments, the expression of 23 genes from Table 7 is determined. In embodiments, the expression of 24 genes from Table 7 is determined. In embodiments, the expression of 25 genes from Table 7 is determined. In embodiments, the expression of 26 genes from Table 7 is determined. In embodiments, the expression of 27 genes from Table 7 is determined. In embodiments, the expression of 28 genes from Table 7 is determined. In embodiments, the expression of 29 genes from Table 7 is determined. In embodiments, the expression of 30 genes from Table 7 is determined. In embodiments, the expression of 31 genes from Table 7 is determined. In embodiments, the expression of 32 genes from Table 7 is determined. In embodiments, the expression of 33 genes from Table 7 is determined. In embodiments, the expression of 34 genes from Table 7 is determined. In embodiments, the expression of 35 genes from Table 7 is determined. In embodiments, the expression of 36 genes from Table 7 is determined. In embodiments, the expression of 37 genes from Table 7 is determined. In embodiments, the expression of 38 genes from Table 7 is determined. In embodiments, the expression of 39 genes from Table 7 is determined. In embodiments, the expression of 40 genes from Table 7 is determined. In embodiments, the expression of 41 genes from Table 7 is determined. In embodiments, the expression of 42 genes from Table 7 is determined. In embodiments, the expression of 43 genes from Table 7 is determined. In embodiments, the expression of 44 genes from Table 7 is determined. In embodiments, the expression of 45 genes from Table 7 is determined. In embodiments, the expression of 46 genes from Table 7 is determined. In embodiments, the expression of 47 genes from Table 7 is determined. In embodiments, the expression of 48 genes from Table 7 is determined. In embodiments, the expression of 49 genes from Table 7 is determined. In embodiments, the expression of 50 genes from Table 7 is determined. In embodiments, the expression of 51 genes from Table 7 is determined. In embodiments, the expression of 52 genes from Table 7 is determined. In embodiments, the expression of 53 genes from Table 7 is determined. In embodiments, the expression of 54 genes from Table 7 is determined. In embodiments, the expression of 55 genes from Table 7 is determined. In embodiments, the expression of 56 genes from Table 7 is determined. In embodiments, the expression of 57 genes from Table 7 is determined. In embodiments, the expression of 58 genes from Table 7 is determined. In embodiments, the expression of 59 genes from Table 7 is determined. In embodiments, the expression of 60 genes from Table 7 is determined. In embodiments, the expression of 61 genes from Table 7 is determined. In embodiments, the expression of 62 genes from Table 7 is determined. In embodiments, the expression of 63 genes from Table 7 is determined. In embodiments, the expression of 64 genes from Table 7 is determined. In embodiments, the expression of 65 genes from Table 7 is determined. In embodiments, the expression of 66 genes from Table 7 is determined. In embodiments, the expression of 67 genes from Table 7 is determined. In embodiments, the expression of 68 genes from Table 7 is determined. In embodiments, the expression of 69 genes from Table 7 is determined. In embodiments, the expression of 70 genes from Table 7 is determined. In embodiments, the expression of 71 genes from Table 7 is determined. In embodiments, the expression of 72 genes from Table 7 is determined. In embodiments, the expression of 73 genes from Table 7 is determined. In embodiments, the expression of 74 genes from Table 7 is determined. In embodiments, the expression of 75 genes from Table 7 is determined. In embodiments, the expression of 76 genes from Table 7 is determined. In embodiments, the expression of 77 genes from Table 7 is determined. In embodiments, the expression of 78 genes from Table 7 is determined. In embodiments, the expression of 79 genes from Table 7 is determined. In embodiments, the expression of 80 genes from Table 7 is determined. In embodiments, the expression of 81 genes from Table 7 is determined. In embodiments, the expression of 82 genes from Table 7 is determined. In embodiments, the expression of 83 genes from Table 7 is determined. In embodiments, the expression of 84 genes from Table 7 is determined. In embodiments, the expression of 85 genes from Table 7 is determined. In embodiments, the expression of 86 genes from Table 7 is determined. In embodiments, the expression of 87 genes from Table 7 is determined. In embodiments, the expression of 88 genes from Table 7 is determined. In embodiments, the expression of 89 genes from Table 7 is determined. In embodiments, the expression of 90 genes from Table 7 is determined. In embodiments, the expression of 91 genes from Table 7 is determined.

In embodiments, the level of expression of one gene from Table 8 is determined. In embodiments, the expression of two genes from Table 8 is determined. In embodiments, the expression of 3 genes from Table 8 is determined. In embodiments, the expression of 4 genes from Table 8 is determined. In embodiments, the expression of 5 genes from Table 8 is determined. In embodiments, the expression of 6 genes from Table 8 is determined. In embodiments, the expression of 7 genes from Table 8 is determined. In embodiments, the expression of 8 genes from Table 8 is determined. In embodiments, the expression of 9 genes from Table 8 is determined. In embodiments, the expression of 10 genes from Table 8 is determined. In embodiments, the expression of 11 genes from Table 8 is determined. In embodiments, the expression of 12 genes from Table 8 is determined. In embodiments, the expression of 13 genes from Table 8 is determined. In embodiments, the expression of 14 genes from Table 8 is determined. In embodiments, the expression of 15 genes from Table 8 is determined. In embodiments, the expression of 16 genes from Table 8 is determined. In embodiments, the expression of 17 genes from Table 8 is determined. In embodiments, the expression of 18 genes from Table 8 is determined. In embodiments, the expression of 19 genes from Table 8 is determined. In embodiments, the expression of 20 genes from Table 8 is determined. In embodiments, the expression of 21 genes from Table 8 is determined. In embodiments, the expression of 22 genes from Table 8 is determined. In embodiments, the expression of 23 genes from Table 8 is determined. In embodiments, the expression of 24 genes from Table 8 is determined. In embodiments, the expression of 25 genes from Table 8 is determined. In embodiments, the expression of 26 genes from Table 8 is determined. In embodiments, the expression of 27 genes from Table 8 is determined. In embodiments, the expression of 28 genes from Table 8 is determined. In embodiments, the expression of 29 genes from Table 8 is determined. In embodiments, the expression of 30 genes from Table 8 is determined. In embodiments, the expression of 31 genes from Table 8 is determined. In embodiments, the expression of 32 genes from Table 8 is determined. In embodiments, the expression of 33 genes from Table 8 is determined. In embodiments, the expression of 34 genes from Table 8 is determined. In embodiments, the expression of 35 genes from Table 8 is determined. In embodiments, the expression of 36 genes from Table 8 is determined. In embodiments, the expression of 37 genes from Table 8 is determined. In embodiments, the expression of 38 genes from Table 8 is determined. In embodiments, the expression of 39 genes from Table 8 is determined. In embodiments, the expression of 40 genes from Table 8 is determined. In embodiments, the expression of 41 genes from Table 8 is determined. In embodiments, the expression of 42 genes from Table 8 is determined. In embodiments, the expression of 43 genes from Table 8 is determined. In embodiments, the expression of 44 genes from Table 8 is determined. In embodiments, the expression of 45 genes from Table 8 is determined. In embodiments, the expression of 46 genes from Table 8 is determined. In embodiments, the expression of 47 genes from Table 8 is determined. In embodiments, the expression of 48 genes from Table 8 is determined. In embodiments, the expression of 49 genes from Table 8 is determined. In embodiments, the expression of 50 genes from Table 8 is determined. In embodiments, the expression of 51 genes from Table 8 is determined. In embodiments, the expression of 52 genes from Table 8 is determined. In embodiments, the expression of 53 genes from Table 8 is determined. In embodiments, the expression of 54 genes from Table 8 is determined. In embodiments, the expression of 55 genes from Table 8 is determined. In embodiments, the expression of 56 genes from Table 8 is determined. In embodiments, the expression of 57 genes from Table 8 is determined. In embodiments, the expression of 58 genes from Table 8 is determined. In embodiments, the expression of 59 genes from Table 8 is determined. In embodiments, the expression of 60 genes from Table 8 is determined. In embodiments, the expression of 61 genes from Table 8 is determined. In embodiments, the expression of 62 genes from Table 8 is determined. In embodiments, the expression of 63 genes from Table 8 is determined. In embodiments, the expression of 64 genes from Table 8 is determined. In embodiments, the expression of 65 genes from Table 8 is determined. In embodiments, the expression of 66 genes from Table 8 is determined. In embodiments, the expression of 67 genes from Table 8 is determined. In embodiments, the expression of 68 genes from Table 8 is determined. In embodiments, the expression of 69 genes from Table 8 is determined. In embodiments, the expression of 70 genes from Table 8 is determined. In embodiments, the expression of 71 genes from Table 8 is determined. In embodiments, the expression of 72 genes from Table 8 is determined. In embodiments, the expression of 73 genes from Table 8 is determined. In embodiments, the expression of 74 genes from Table 8 is determined. In embodiments, the expression of 75 genes from Table 8 is determined. In embodiments, the expression of 76 genes from Table 8 is determined. In embodiments, the expression of 77 genes from Table 8 is determined. In embodiments, the expression of 78 genes from Table 8 is determined. In embodiments, the expression of 79 genes from Table 8 is determined. In embodiments, the expression of 80 genes from Table 8 is determined. In embodiments, the expression of 81 genes from Table 8 is determined. In embodiments, the expression of 82 genes from Table 8 is determined. In embodiments, the expression of 83 genes from Table 8 is determined. In embodiments, the expression of 84 genes from Table 8 is determined. In embodiments, the expression of 85 genes from Table 8 is determined. In embodiments, the expression of 86 genes from Table 8 is determined. In embodiments, the expression of 87 genes from Table 8 is determined. In embodiments, the expression of 88 genes from Table 8 is determined. In embodiments, the expression of 89 genes from Table 8 is determined. In embodiments, the expression of 90 genes from Table 8 is determined. In embodiments, the expression of 91 genes from Table 8 is determined. In embodiments, the expression of 92 genes from Table 8 is determined. In embodiments, the expression of 93 genes from Table 8 is determined. In embodiments, the expression of 94 genes from Table 8 is determined. In embodiments, the expression of 95 genes from Table 8 is determined. In embodiments, the expression of 96 genes from Table 8 is determined. In embodiments, the expression of 97 genes from Table 8 is determined. In embodiments, the expression of 98 genes from Table 8 is determined. In embodiments, the expression of 99 genes from Table 8 is determined. In embodiments, the expression of 100 genes from Table 8 is determined. In embodiments, the expression of 101 genes from Table 8 is determined. In embodiments, the expression of 102 genes from Table 8 is determined. In embodiments, the expression of 103 genes from Table 8 is determined. In embodiments, the expression of 104 genes from Table 8 is determined. In embodiments, the expression of 105 genes from Table 8 is determined. In embodiments, the expression of 106 genes from Table 8 is determined. In embodiments, the expression of 107 genes from Table 8 is determined. In embodiments, the expression of 108 genes from Table 8 is determined. In embodiments, the expression of 109 genes from Table 8 is determined. In embodiments, the expression of 110 genes from Table 8 is determined. In embodiments, the expression of 120 genes from Table 8 is determined. In embodiments, the expression of 130 genes from Table 8 is determined. In embodiments, the expression of 140 genes from Table 8 is determined. In embodiments, the expression of 150 genes from Table 8 is determined. In embodiments, the expression of 160 genes from Table 8 is determined. In embodiments, the expression of 170 genes from Table 8 is determined. In embodiments, the expression of 180 genes from Table 8 is determined. In embodiments, the expression of 190 genes from Table 8 is determined. In embodiments, the expression of 196 genes from Table 8 is determined.

In embodiments, the level of expression of one gene from Table 9 is determined. In embodiments, the expression of two genes from Table 9 is determined. In embodiments, the expression of 3 genes from Table 9 is determined. In embodiments, the expression of 4 genes from Table 9 is determined. In embodiments, the expression of 5 genes from Table 9 is determined. In embodiments, the expression of 6 genes from Table 9 is determined. In embodiments, the expression of 7 genes from Table 9 is determined. In embodiments, the expression of 8 genes from Table 9 is determined. In embodiments, the expression of 9 genes from Table 9 is determined. In embodiments, the expression of 10 genes from Table 9 is determined. In embodiments, the expression of 11 genes from Table 9 is determined. In embodiments, the expression of 12 genes from Table 9 is determined. In embodiments, the expression of 13 genes from Table 9 is determined. In embodiments, the expression of 14 genes from Table 9 is determined. In embodiments, the expression of 15 genes from Table 9 is determined. In embodiments, the expression of 16 genes from Table 9 is determined. In embodiments, the expression of 17 genes from Table 9 is determined. In embodiments, the expression of 18 genes from Table 9 is determined. In embodiments, the expression of 19 genes from Table 9 is determined. In embodiments, the expression of 20 genes from Table 9 is determined. In embodiments, the expression of 21 genes from Table 9 is determined. In embodiments, the expression of 22 genes from Table 9 is determined. In embodiments, the expression of 23 genes from Table 9 is determined.

In embodiments, the level of expression of at least one protein from Table 1 is determined. In embodiments, the expression of at least two proteins from Table 1 is determined. In embodiments, the expression of at least 3 proteins from Table 1 is determined. In embodiments, the expression of at least 4 proteins from Table 1 is determined. In embodiments, the expression of at least 5 proteins from Table 1 is determined. In embodiments, the expression of at least 6 proteins from Table 1 is determined. In embodiments, the expression of at least 7 proteins from Table 1 is determined. In embodiments, the expression of at least 8 proteins from Table 1 is determined. In embodiments, the expression of at least 9 proteins from Table 1 is determined. In embodiments, the expression of at least 10 proteins from Table 1 is determined. In embodiments, the expression of at least 11 proteins from Table 1 is determined. In embodiments, the expression of at least 12 proteins from Table 1 is determined. In embodiments, the expression of at least 13 proteins from Table 1 is determined. In embodiments, the expression of at least 14 proteins from Table 1 is determined. In embodiments, the expression of at least 15 proteins from Table 1 is determined. In embodiments, the expression of at least 16 proteins from Table 1 is determined. In embodiments, the expression of at least 17 proteins from Table 1 is determined. In embodiments, the expression of at least 18 proteins from Table 1 is determined. In embodiments, the expression of at least 19 proteins from Table 1 is determined. In embodiments, the expression of at least 20 proteins from Table 1 is determined. In embodiments, the expression of at least 21 proteins from Table 1 is determined. In embodiments, the expression of at least 22 proteins from Table 1 is determined. In embodiments, the expression of at least 23 proteins from Table 1 is determined. In embodiments, the expression of at least 24 proteins from Table 1 is determined. In embodiments, the expression of at least 25 proteins from Table 1 is determined. In embodiments, the expression of at least 26 proteins from Table 1 is determined. In embodiments, the expression of at least 27 proteins from Table 1 is determined. In embodiments, the expression of at least 28 proteins from Table 1 is determined. In embodiments, the expression of at least 29 proteins from Table 1 is determined. In embodiments, the expression of at least 30 proteins from Table 1 is determined. In embodiments, the expression of at least 35 proteins from Table 1 is determined. In embodiments, the expression of at least 40 proteins from Table 1 is determined. In embodiments, the expression of at least 45 proteins from Table 1 is determined. In embodiments, the expression of at least 50 proteins from Table 1 is determined. In embodiments, the expression of at least 55 proteins from Table 1 is determined. In embodiments, the expression of at least 60 proteins from Table 1 is determined. In embodiments, the expression of at least 65 proteins from Table 1 is determined.

In embodiments, the level of expression of one protein from Table 1 is determined. In embodiments, the expression of two proteins from Table 1 is determined. In embodiments, the expression of 3 proteins from Table 1 is determined. In embodiments, the expression of 4 proteins from Table 1 is determined. In embodiments, the expression of 5 proteins from Table 1 is determined. In embodiments, the expression of 6 proteins from Table 1 is determined. In embodiments, the expression of 7 proteins from Table 1 is determined. In embodiments, the expression of 8 proteins from Table 1 is determined. In embodiments, the expression of 9 proteins from Table 1 is determined. In embodiments, the expression of 10 proteins from Table 1 is determined. In embodiments, the expression of 11 proteins from Table 1 is determined. In embodiments, the expression of 12 proteins from Table 1 is determined. In embodiments, the expression of 13 proteins from Table 1 is determined. In embodiments, the expression of 14 proteins from Table 1 is determined. In embodiments, the expression of 15 proteins from Table 1 is determined. In embodiments, the expression of 16 proteins from Table 1 is determined. In embodiments, the expression of 17 proteins from Table 1 is determined. In embodiments, the expression of 18 proteins from Table 1 is determined. In embodiments, the expression of 19 proteins from Table 1 is determined. In embodiments, the expression of 20 proteins from Table 1 is determined. In embodiments, the expression of 21 proteins from Table 1 is determined. In embodiments, the expression of 22 proteins from Table 1 is determined. In embodiments, the expression of 23 proteins from Table 1 is determined. In embodiments, the expression of 24 proteins from Table 1 is determined. In embodiments, the expression of 25 proteins from Table 1 is determined. In embodiments, the expression of 26 proteins from Table 1 is determined. In embodiments, the expression of 27 proteins from Table 1 is determined. In embodiments, the expression of 28 proteins from Table 1 is determined. In embodiments, the expression of 29 proteins from Table 1 is determined. In embodiments, the expression of 30 proteins from Table 1 is determined. In embodiments, the expression of 31 proteins from Table 1 is determined. In embodiments, the expression of 32 proteins from Table 1 is determined. In embodiments, the expression of 33 proteins from Table 1 is determined. In embodiments, the expression of 34 proteins from Table 1 is determined. In embodiments, the expression of 35 proteins from Table 1 is determined. In embodiments, the expression of 36 proteins from Table 1 is determined. In embodiments, the expression of 37 proteins from Table 1 is determined. In embodiments, the expression of 38 proteins from Table 1 is determined. In embodiments, the expression of 39 proteins from Table 1 is determined. In embodiments, the expression of 40 proteins from Table 1 is determined. In embodiments, the expression of 41 proteins from Table 1 is determined. In embodiments, the expression of 42 proteins from Table 1 is determined. In embodiments, the expression of 43 proteins from Table 1 is determined. In embodiments, the expression of 44 proteins from Table 1 is determined. In embodiments, the expression of 45 proteins from Table 1 is determined. In embodiments, the expression of 46 proteins from Table 1 is determined. In embodiments, the expression of 47 proteins from Table 1 is determined. In embodiments, the expression of 48 proteins from Table 1 is determined. In embodiments, the expression of 49 proteins from Table 1 is determined. In embodiments, the expression of 50 proteins from Table 1 is determined. In embodiments, the expression of 51 proteins from Table 1 is determined. In embodiments, the expression of 52 proteins from Table 1 is determined. In embodiments, the expression of 53 proteins from Table 1 is determined. In embodiments, the expression of 54 proteins from Table 1 is determined. In embodiments, the expression of 55 proteins from Table 1 is determined. In embodiments, the expression of 56 proteins from Table 1 is determined. In embodiments, the expression of 57 proteins from Table 1 is determined. In embodiments, the expression of 58 proteins from Table 1 is determined. In embodiments, the expression of 59 proteins from Table 1 is determined. In embodiments, the expression of 60 proteins from Table 1 is determined. In embodiments, the expression of 61 proteins from Table 1 is determined. In embodiments, the expression of 62 proteins from Table 1 is determined. In embodiments, the expression of 63 proteins from Table 1 is determined. In embodiments, the expression of 64 proteins from Table 1 is determined. In embodiments, the expression of 65 proteins from Table 1 is determined. In embodiments, the expression of 66 proteins from Table 1 is determined. In embodiments, the expression of 67 proteins from Table 1 is determined.

In embodiments, the level of expression of at least one protein from Table 2 is determined. In embodiments, the expression of at least two proteins from Table 2 is determined. In embodiments, the expression of at least 3 proteins from Table 2 is determined. In embodiments, the expression of at least 4 proteins from Table 2 is determined. In embodiments, the expression of at least 5 proteins from Table 2 is determined. In embodiments, the expression of at least 6 proteins from Table 2 is determined. In embodiments, the expression of at least 7 proteins from Table 2 is determined. In embodiments, the expression of at least 8 proteins from Table 2 is determined. In embodiments, the expression of at least 9 proteins from Table 2 is determined. In embodiments, the expression of at least 10 proteins from Table 2 is determined. In embodiments, the expression of at least 11 proteins from Table 2 is determined. In embodiments, the expression of at least 12 proteins from Table 2 is determined. In embodiments, the expression of at least 13 proteins from Table 2 is determined. In embodiments, the expression of at least 14 proteins from Table 2 is determined. In embodiments, the expression of at least 15 proteins from Table 2 is determined. In embodiments, the expression of at least 16 proteins from Table 2 is determined. In embodiments, the expression of at least 17 proteins from Table 2 is determined. In embodiments, the expression of at least 18 proteins from Table 2 is determined. In embodiments, the expression of at least 19 proteins from Table 2 is determined. In embodiments, the expression of at least 20 proteins from Table 2 is determined. In embodiments, the expression of at least 21 proteins from Table 2 is determined. In embodiments, the expression of at least 22 proteins from Table 2 is determined. In embodiments, the expression of at least 23 proteins from Table 2 is determined. In embodiments, the expression of at least 24 proteins from Table 2 is determined. In embodiments, the expression of at least 25 proteins from Table 2 is determined. In embodiments, the expression of at least 26 proteins from Table 2 is determined. In embodiments, the expression of at least 27 proteins from Table 2 is determined. In embodiments, the expression of at least 28 proteins from Table 2 is determined. In embodiments, the expression of at least 29 proteins from Table 2 is determined. In embodiments, the expression of at least 30 proteins from Table 2 is determined. In embodiments, the expression of at least 35 proteins from Table 2 is determined. In embodiments, the expression of at least 40 proteins from Table 2 is determined. In embodiments, the expression of at least 45 proteins from Table 2 is determined. In embodiments, the expression of at least 50 proteins from Table 2 is determined. In embodiments, the expression of at least 55 proteins from Table 2 is determined. In embodiments, the expression of at least 60 proteins from Table 2 is determined. In embodiments, the expression of at least 65 proteins from Table 2 is determined. In embodiments, the expression of at least 70 proteins from Table 2 is determined. In embodiments, the expression of at least 75 proteins from Table 2 is determined. In embodiments, the expression of at least 80 proteins from Table 2 is determined. In embodiments, the expression of at least 85 proteins from Table 2 is determined. In embodiments, the expression of at least 90 proteins from Table 2 is determined. In embodiments, the expression of at least 95 proteins from Table 2 is determined. In embodiments, the expression of at least 100 proteins from Table 2 is determined. In an embodiment, a subject having a high level of any one or more of these genes/proteins (compared to a control) is administered an adenosine pathway inhibitor.

In embodiments, the level of expression of one protein from Table 2 is determined. In embodiments, the expression of two proteins from Table 2 is determined. In embodiments, the expression of 3 proteins from Table 2 is determined. In embodiments, the expression of 4 proteins from Table 2 is determined. In embodiments, the expression of 5 proteins from Table 2 is determined. In embodiments, the expression of 6 proteins from Table 2 is determined. In embodiments, the expression of 7 proteins from Table 2 is determined. In embodiments, the expression of 8 proteins from Table 2 is determined. In embodiments, the expression of 9 proteins from Table 2 is determined. In embodiments, the expression of 10 proteins from Table 2 is determined. In embodiments, the expression of 11 proteins from Table 2 is determined. In embodiments, the expression of 12 proteins from Table 2 is determined. In embodiments, the expression of 13 proteins from Table 2 is determined. In embodiments, the expression of 14 proteins from Table 2 is determined. In embodiments, the expression of 15 proteins from Table 2 is determined. In embodiments, the expression of 16 proteins from Table 2 is determined. In embodiments, the expression of 17 proteins from Table 2 is determined. In embodiments, the expression of 18 proteins from Table 2 is determined. In embodiments, the expression of 19 proteins from Table 2 is determined. In embodiments, the expression of 20 proteins from Table 2 is determined. In embodiments, the expression of 21 proteins from Table 2 is determined. In embodiments, the expression of 22 proteins from Table 2 is determined. In embodiments, the expression of 23 proteins from Table 2 is determined. In embodiments, the expression of 24 proteins from Table 2 is determined. In embodiments, the expression of 25 proteins from Table 2 is determined. In embodiments, the expression of 26 proteins from Table 2 is determined. In embodiments, the expression of 27 proteins from Table 2 is determined. In embodiments, the expression of 28 proteins from Table 2 is determined. In embodiments, the expression of 29 proteins from Table 2 is determined. In embodiments, the expression of 30 proteins from Table 2 is determined. In embodiments, the expression of 31 proteins from Table 2 is determined. In embodiments, the expression of 32 proteins from Table 2 is determined. In embodiments, the expression of 33 proteins from Table 2 is determined. In embodiments, the expression of 34 proteins from Table 2 is determined. In embodiments, the expression of 35 proteins from Table 2 is determined. In embodiments, the expression of 36 proteins from Table 2 is determined. In embodiments, the expression of 37 proteins from Table 2 is determined. In embodiments, the expression of 38 proteins from Table 2 is determined. In embodiments, the expression of 39 proteins from Table 2 is determined. In embodiments, the expression of 40 proteins from Table 2 is determined. In embodiments, the expression of 41 proteins from Table 2 is determined. In embodiments, the expression of 42 proteins from Table 2 is determined. In embodiments, the expression of 43 proteins from Table 2 is determined. In embodiments, the expression of 44 proteins from Table 2 is determined. In embodiments, the expression of 45 proteins from Table 2 is determined. In embodiments, the expression of 46 proteins from Table 2 is determined. In embodiments, the expression of 47 proteins from Table 2 is determined. In embodiments, the expression of 48 proteins from Table 2 is determined. In embodiments, the expression of 49 proteins from Table 2 is determined. In embodiments, the expression of 50 proteins from Table 2 is determined. In embodiments, the expression of 51 proteins from Table 2 is determined. In embodiments, the expression of 52 proteins from Table 2 is determined. In embodiments, the expression of 53 proteins from Table 2 is determined. In embodiments, the expression of 54 proteins from Table 2 is determined. In embodiments, the expression of 55 proteins from Table 2 is determined. In embodiments, the expression of 56 proteins from Table 2 is determined. In embodiments, the expression of 57 proteins from Table 2 is determined. In embodiments, the expression of 58 proteins from Table 2 is determined. In embodiments, the expression of 59 proteins from Table 2 is determined. In embodiments, the expression of 60 proteins from Table 2 is determined. In embodiments, the expression of 61 proteins from Table 2 is determined. In embodiments, the expression of 62 proteins from Table 2 is determined. In embodiments, the expression of 63 proteins from Table 2 is determined. In embodiments, the expression of 64 proteins from Table 2 is determined. In embodiments, the expression of 65 proteins from Table 2 is determined. In embodiments, the expression of 66 proteins from Table 2 is determined. In embodiments, the expression of 67 proteins from Table 2 is determined. In embodiments, the expression of 68 proteins from Table 2 is determined. In embodiments, the expression of 69 proteins from Table 2 is determined. In embodiments, the expression of 70 proteins from Table 2 is determined. In embodiments, the expression of 71 proteins from Table 2 is determined. In embodiments, the expression of 72 proteins from Table 2 is determined. In embodiments, the expression of 73 proteins from Table 2 is determined. In embodiments, the expression of 74 proteins from Table 2 is determined. In embodiments, the expression of 75 proteins from Table 2 is determined. In embodiments, the expression of 76 proteins from Table 2 is determined. In embodiments, the expression of 77 proteins from Table 2 is determined. In embodiments, the expression of 78 proteins from Table 2 is determined. In embodiments, the expression of 79 proteins from Table 2 is determined. In embodiments, the expression of 80 proteins from Table 2 is determined. In embodiments, the expression of 81 proteins from Table 2 is determined. In embodiments, the expression of 82 proteins from Table 2 is determined. In embodiments, the expression of 83 proteins from Table 2 is determined. In embodiments, the expression of 84 proteins from Table 2 is determined. In embodiments, the expression of 85 proteins from Table 2 is determined. In embodiments, the expression of 86 proteins from Table 2 is determined. In embodiments, the expression of 87 proteins from Table 2 is determined. In embodiments, the expression of 88 proteins from Table 2 is determined. In embodiments, the expression of 89 proteins from Table 2 is determined. In embodiments, the expression of 90 proteins from Table 2 is determined. In embodiments, the expression of 91 proteins from Table 2 is determined. In embodiments, the expression of 92 proteins from Table 2 is determined. In embodiments, the expression of 93 proteins from Table 2 is determined. In embodiments, the expression of 94 proteins from Table 2 is determined. In embodiments, the expression of 95 proteins from Table 2 is determined. In embodiments, the expression of 96 proteins from Table 2 is determined. In embodiments, the expression of 97 proteins from Table 2 is determined. In embodiments, the expression of 98 proteins from Table 2 is determined. In embodiments, the expression of 99 proteins from Table 2 is determined. In embodiments, the expression of 100 proteins from Table 2 is determined. In embodiments, the expression of 101 proteins from Table 2 is determined. In embodiments, the expression of 102 proteins from Table 2 is determined. In embodiments, the expression of 103 proteins from Table 2 is determined. In embodiments, the expression of 104 proteins from Table 2 is determined. In embodiments, the expression of 105 proteins from Table 2 is determined. In embodiments, the expression of 106 proteins from Table 2 is determined. In embodiments, the expression of 107 proteins from Table 2 is determined. In embodiments, the expression of 108 proteins from Table 2 is determined. In embodiments, the expression of 109 genes from Table 2 is determined.

In embodiments, the level of expression of at least one protein from Table 7 is determined. In embodiments, the expression of at least two proteins from Table 7 is determined. In embodiments, the expression of at least 3 proteins from Table 7 is determined. In embodiments, the expression of at least 4 proteins from Table 7 is determined. In embodiments, the expression of at least 5 proteins from Table 7 is determined. In embodiments, the expression of at least 6 proteins from Table 7 is determined. In embodiments, the expression of at least 7 proteins from Table 7 is determined. In embodiments, the expression of at least 8 proteins from Table 7 is determined. In embodiments, the expression of at least 9 proteins from Table 7 is determined. In embodiments, the expression of at least 10 proteins from Table 7 is determined. In embodiments, the expression of at least 11 proteins from Table 7 is determined. In embodiments, the expression of at least 12 proteins from Table 7 is determined. In embodiments, the expression of at least 13 proteins from Table 7 is determined. In embodiments, the expression of at least 14 proteins from Table 7 is determined. In embodiments, the expression of at least 15 proteins from Table 7 is determined. In embodiments, the expression of at least 16 proteins from Table 7 is determined. In embodiments, the expression of at least 17 proteins from Table 7 is determined. In embodiments, the expression of at least 18 proteins from Table 7 is determined. In embodiments, the expression of at least 19 proteins from Table 7 is determined. In embodiments, the expression of at least 20 proteins from Table 7 is determined. In embodiments, the expression of at least 21 proteins from Table 7 is determined. In embodiments, the expression of at least 22 proteins from Table 7 is determined. In embodiments, the expression of at least 23 proteins from Table 7 is determined. In embodiments, the expression of at least 24 proteins from Table 7 is determined. In embodiments, the expression of at least 25 proteins from Table 7 is determined. In embodiments, the expression of at least 26 proteins from Table 7 is determined. In embodiments, the expression of at least 27 proteins from Table 7 is determined. In embodiments, the expression of at least 28 proteins from Table 7 is determined. In embodiments, the expression of at least 29 proteins from Table 7 is determined. In embodiments, the expression of at least 30 proteins from Table 7 is determined. In embodiments, the expression of at least 35 proteins from Table 7 is determined. In embodiments, the expression of at least 40 proteins from Table 7 is determined. In embodiments, the expression of at least 45 proteins from Table 7 is determined. In embodiments, the expression of at least 50 proteins from Table 7 is determined. In embodiments, the expression of at least 55 proteins from Table 7 is determined. In embodiments, the expression of at least 60 proteins from Table 7 is determined. In embodiments, the expression of at least 65 proteins from Table 7 is determined. In embodiments, the expression of at least 70 proteins from Table 7 is determined. In embodiments, the expression of at least 75 proteins from Table 7 is determined. In embodiments, the expression of at least 80 proteins from Table 7 is determined. In embodiments, the expression of at least 85 proteins from Table 7 is determined. In embodiments, the expression of at least 90 proteins from Table 7 is determined. In embodiments, the expression of at least 95 proteins from Table 7 is determined. In an embodiment, a subject having a high level of any one or more of these genes/proteins (compared to a control) is administered an adenosine pathway inhibitor.

In embodiments, the level of expression of one protein from Table 7 is determined. In embodiments, the expression of two proteins from Table 7 is determined. In embodiments, the expression of 3 proteins from Table 7 is determined. In embodiments, the expression of 4 proteins from Table 7 is determined. In embodiments, the expression of 5 proteins from Table 7 is determined. In embodiments, the expression of 6 proteins from Table 7 is determined. In embodiments, the expression of 7 proteins from Table 7 is determined. In embodiments, the expression of 8 proteins from Table 7 is determined. In embodiments, the expression of 9 proteins from Table 7 is determined. In embodiments, the expression of 10 proteins from Table 7 is determined. In embodiments, the expression of 11 proteins from Table 7 is determined. In embodiments, the expression of 12 proteins from Table 7 is determined. In embodiments, the expression of 13 proteins from Table 7 is determined. In embodiments, the expression of 14 proteins from Table 7 is determined. In embodiments, the expression of 15 proteins from Table 7 is determined. In embodiments, the expression of 16 proteins from Table 7 is determined. In embodiments, the expression of 17 proteins from Table 7 is determined. In embodiments, the expression of 18 proteins from Table 7 is determined. In embodiments, the expression of 19 proteins from Table 7 is determined. In embodiments, the expression of 20 proteins from Table 7 is determined. In embodiments, the expression of 21 proteins from Table 7 is determined. In embodiments, the expression of 22 proteins from Table 7 is determined. In embodiments, the expression of 23 proteins from Table 7 is determined. In embodiments, the expression of 24 proteins from Table 7 is determined. In embodiments, the expression of 25 proteins from Table 7 is determined. In embodiments, the expression of 26 proteins from Table 7 is determined. In embodiments, the expression of 27 proteins from Table 7 is determined. In embodiments, the expression of 28 proteins from Table 7 is determined. In embodiments, the expression of 29 proteins from Table 7 is determined. In embodiments, the expression of 30 proteins from Table 7 is determined. In embodiments, the expression of 31 proteins from Table 7 is determined. In embodiments, the expression of 32 proteins from Table 7 is determined. In embodiments, the expression of 33 proteins from Table 7 is determined. In embodiments, the expression of 34 proteins from Table 7 is determined. In embodiments, the expression of 35 proteins from Table 7 is determined. In embodiments, the expression of 36 proteins from Table 7 is determined. In embodiments, the expression of 37 proteins from Table 7 is determined. In embodiments, the expression of 38 proteins from Table 7 is determined. In embodiments, the expression of 39 proteins from Table 7 is determined. In embodiments, the expression of 40 proteins from Table 7 is determined. In embodiments, the expression of 41 proteins from Table 7 is determined. In embodiments, the expression of 42 proteins from Table 7 is determined. In embodiments, the expression of 43 proteins from Table 7 is determined. In embodiments, the expression of 44 proteins from Table 7 is determined. In embodiments, the expression of 45 proteins from Table 7 is determined. In embodiments, the expression of 46 proteins from Table 7 is determined. In embodiments, the expression of 47 proteins from Table 7 is determined. In embodiments, the expression of 48 proteins from Table 7 is determined. In embodiments, the expression of 49 proteins from Table 7 is determined. In embodiments, the expression of 50 proteins from Table 7 is determined. In embodiments, the expression of 51 proteins from Table 7 is determined. In embodiments, the expression of 52 proteins from Table 7 is determined. In embodiments, the expression of 53 proteins from Table 7 is determined. In embodiments, the expression of 54 proteins from Table 7 is determined. In embodiments, the expression of 55 proteins from Table 7 is determined. In embodiments, the expression of 56 proteins from Table 7 is determined. In embodiments, the expression of 57 proteins from Table 7 is determined. In embodiments, the expression of 58 proteins from Table 7 is determined. In embodiments, the expression of 59 proteins from Table 7 is determined. In embodiments, the expression of 60 proteins from Table 7 is determined. In embodiments, the expression of 61 proteins from Table 7 is determined. In embodiments, the expression of 62 proteins from Table 7 is determined. In embodiments, the expression of 63 proteins from Table 7 is determined. In embodiments, the expression of 64 proteins from Table 7 is determined. In embodiments, the expression of 65 proteins from Table 7 is determined. In embodiments, the expression of 66 proteins from Table 7 is determined. In embodiments, the expression of 67 proteins from Table 7 is determined. In embodiments, the expression of 68 proteins from Table 7 is determined. In embodiments, the expression of 69 proteins from Table 7 is determined. In embodiments, the expression of 70 proteins from Table 7 is determined. In embodiments, the expression of 71 proteins from Table 7 is determined. In embodiments, the expression of 72 proteins from Table 7 is determined. In embodiments, the expression of 73 proteins from Table 7 is determined. In embodiments, the expression of 74 proteins from Table 7 is determined. In embodiments, the expression of 75 proteins from Table 7 is determined. In embodiments, the expression of 76 proteins from Table 7 is determined. In embodiments, the expression of 77 proteins from Table 7 is determined. In embodiments, the expression of 78 proteins from Table 7 is determined. In embodiments, the expression of 79 proteins from Table 7 is determined. In embodiments, the expression of 80 proteins from Table 7 is determined. In embodiments, the expression of 81 proteins from Table 7 is determined. In embodiments, the expression of 82 proteins from Table 7 is determined. In embodiments, the expression of 83 proteins from Table 7 is determined. In embodiments, the expression of 84 proteins from Table 7 is determined. In embodiments, the expression of 85 proteins from Table 7 is determined. In embodiments, the expression of 86 proteins from Table 7 is determined. In embodiments, the expression of 87 proteins from Table 7 is determined. In embodiments, the expression of 88 proteins from Table 7 is determined. In embodiments, the expression of 89 proteins from Table 7 is determined. In embodiments, the expression of 90 proteins from Table 7 is determined. In embodiments, the expression of 91 proteins from Table 7 is determined. In embodiments, the expression of 92 proteins from Table 7 is determined. In embodiments, the expression of 93 proteins from Table 7 is determined. In embodiments, the expression of 94 proteins from Table 7 is determined. In embodiments, the expression of 95 proteins from Table 7 is determined. In embodiments, the expression of 96 proteins from Table 7 is determined.

In embodiments, the level of expression of one protein from Table 8 is determined. In embodiments, the expression of two proteins from Table 8 is determined. In embodiments, the expression of 3 proteins from Table 8 is determined. In embodiments, the expression of 4 proteins from Table 8 is determined. In embodiments, the expression of 5 proteins from Table 8 is determined. In embodiments, the expression of 6 proteins from Table 8 is determined. In embodiments, the expression of 7 proteins from Table 8 is determined. In embodiments, the expression of 8 proteins from Table 8 is determined. In embodiments, the expression of 9 proteins from Table 8 is determined. In embodiments, the expression of 10 proteins from Table 8 is determined. In embodiments, the expression of 11 proteins from Table 8 is determined. In embodiments, the expression of 12 proteins from Table 8 is determined. In embodiments, the expression of 13 proteins from Table 8 is determined. In embodiments, the expression of 14 proteins from Table 8 is determined. In embodiments, the expression of 15 proteins from Table 8 is determined. In embodiments, the expression of 16 proteins from Table 8 is determined. In embodiments, the expression of 17 proteins from Table 8 is determined. In embodiments, the expression of 18 proteins from Table 8 is determined. In embodiments, the expression of 19 proteins from Table 8 is determined. In embodiments, the expression of 20 proteins from Table 8 is determined. In embodiments, the expression of 21 proteins from Table 8 is determined. In embodiments, the expression of 22 proteins from Table 8 is determined. In embodiments, the expression of 23 proteins from Table 8 is determined. In embodiments, the expression of 24 proteins from Table 8 is determined. In embodiments, the expression of 25 proteins from Table 8 is determined. In embodiments, the expression of 26 proteins from Table 8 is determined. In embodiments, the expression of 27 proteins from Table 8 is determined. In embodiments, the expression of 28 proteins from Table 8 is determined. In embodiments, the expression of 29 proteins from Table 8 is determined. In embodiments, the expression of 30 proteins from Table 8 is determined. In embodiments, the expression of 31 proteins from Table 8 is determined. In embodiments, the expression of 32 proteins from Table 8 is determined. In embodiments, the expression of 33 proteins from Table 8 is determined. In embodiments, the expression of 34 proteins from Table 8 is determined. In embodiments, the expression of 35 proteins from Table 8 is determined. In embodiments, the expression of 36 proteins from Table 8 is determined. In embodiments, the expression of 37 proteins from Table 8 is determined. In embodiments, the expression of 38 proteins from Table 8 is determined. In embodiments, the expression of 39 proteins from Table 8 is determined. In embodiments, the expression of 40 proteins from Table 8 is determined. In embodiments, the expression of 41 proteins from Table 8 is determined. In embodiments, the expression of 42 proteins from Table 8 is determined. In embodiments, the expression of 43 proteins from Table 8 is determined. In embodiments, the expression of 44 proteins from Table 8 is determined. In embodiments, the expression of 45 proteins from Table 8 is determined. In embodiments, the expression of 46 proteins from Table 8 is determined. In embodiments, the expression of 47 proteins from Table 8 is determined. In embodiments, the expression of 48 proteins from Table 8 is determined. In embodiments, the expression of 49 proteins from Table 8 is determined. In embodiments, the expression of 50 proteins from Table 8 is determined. In embodiments, the expression of 51 proteins from Table 8 is determined. In embodiments, the expression of 52 proteins from Table 8 is determined. In embodiments, the expression of 53 proteins from Table 8 is determined. In embodiments, the expression of 54 proteins from Table 8 is determined. In embodiments, the expression of 55 proteins from Table 8 is determined. In embodiments, the expression of 56 proteins from Table 8 is determined. In embodiments, the expression of 57 proteins from Table 8 is determined. In embodiments, the expression of 58 proteins from Table 8 is determined. In embodiments, the expression of 59 proteins from Table 8 is determined. In embodiments, the expression of 60 proteins from Table 8 is determined. In embodiments, the expression of 61 proteins from Table 8 is determined. In embodiments, the expression of 62 proteins from Table 8 is determined. In embodiments, the expression of 63 proteins from Table 8 is determined. In embodiments, the expression of 64 proteins from Table 8 is determined. In embodiments, the expression of 65 proteins from Table 8 is determined. In embodiments, the expression of 66 proteins from Table 8 is determined. In embodiments, the expression of 67 proteins from Table 8 is determined. In embodiments, the expression of 68 proteins from Table 8 is determined. In embodiments, the expression of 69 proteins from Table 8 is determined. In embodiments, the expression of 70 proteins from Table 8 is determined. In embodiments, the expression of 71 proteins from Table 8 is determined. In embodiments, the expression of 72 proteins from Table 8 is determined. In embodiments, the expression of 73 proteins from Table 8 is determined. In embodiments, the expression of 74 proteins from Table 8 is determined. In embodiments, the expression of 75 proteins from Table 8 is determined. In embodiments, the expression of 76 proteins from Table 8 is determined. In embodiments, the expression of 77 proteins from Table 8 is determined. In embodiments, the expression of 78 proteins from Table 8 is determined. In embodiments, the expression of 79 proteins from Table 8 is determined. In embodiments, the expression of 80 proteins from Table 8 is determined. In embodiments, the expression of 81 proteins from Table 8 is determined. In embodiments, the expression of 82 proteins from Table 8 is determined. In embodiments, the expression of 83 proteins from Table 8 is determined. In embodiments, the expression of 84 proteins from Table 8 is determined. In embodiments, the expression of 85 proteins from Table 8 is determined. In embodiments, the expression of 86 proteins from Table 8 is determined. In embodiments, the expression of 87 proteins from Table 8 is determined. In embodiments, the expression of 88 proteins from Table 8 is determined. In embodiments, the expression of 89 proteins from Table 8 is determined. In embodiments, the expression of 90 proteins from Table 8 is determined. In embodiments, the expression of 91 proteins from Table 8 is determined. In embodiments, the expression of 92 proteins from Table 8 is determined. In embodiments, the expression of 93 proteins from Table 8 is determined. In embodiments, the expression of 94 proteins from Table 8 is determined. In embodiments, the expression of 95 proteins from Table 8 is determined. In embodiments, the expression of 96 proteins from Table 8 is determined. In embodiments, the expression of 97 proteins from Table 8 is determined. In embodiments, the expression of 98 proteins from Table 8 is determined. In embodiments, the expression of 99 proteins from Table 8 is determined. In embodiments, the expression of 100 proteins from Table 8 is determined. In embodiments, the expression of 101 proteins from Table 8 is determined. In embodiments, the expression of 102 proteins from Table 8 is determined. In embodiments, the expression of 103 proteins from Table 8 is determined. In embodiments, the expression of 104 proteins from Table 8 is determined. In embodiments, the expression of 105 proteins from Table 8 is determined. In embodiments, the expression of 106 proteins from Table 8 is determined. In embodiments, the expression of 107 proteins from Table 8 is determined. In embodiments, the expression of 108 proteins from Table 8 is determined. In embodiments, the expression of 109 proteins from Table 8 is determined. In embodiments, the expression of 110 proteins from Table 8 is determined. In embodiments, the expression of 120 proteins from Table 8 is determined. In embodiments, the expression of 130 proteins from Table 8 is determined. In embodiments, the expression of 140 proteins from Table 8 is determined. In embodiments, the expression of 150 proteins from Table 8 is determined. In embodiments, the expression of 160 proteins from Table 8 is determined. In embodiments, the expression of 170 proteins from Table 8 is determined. In embodiments, the expression of 180 proteins from Table 8 is determined. In embodiments, the expression of 190 proteins from Table 8 is determined. In embodiments, the expression of 196 proteins from Table 8 is determined.

In embodiments, the level of expression of one protein from Table 9 is determined. In embodiments, the expression of two proteins from Table 9 is determined. In embodiments, the expression of 3 proteins from Table 9 is determined. In embodiments, the expression of 4 proteins from Table 9 is determined. In embodiments, the expression of 5 proteins from Table 9 is determined. In embodiments, the expression of 6 proteins from Table 9 is determined. In embodiments, the expression of 7 proteins from Table 9 is determined. In embodiments, the expression of 8 proteins from Table 9 is determined. In embodiments, the expression of 9 proteins from Table 9 is determined. In embodiments, the expression of 10 proteins from Table 9 is determined. In embodiments, the expression of 11 proteins from Table 9 is determined. In embodiments, the expression of 12 proteins from Table 9 is determined. In embodiments, the expression of 13 proteins from Table 9 is determined. In embodiments, the expression of 14 proteins from Table 9 is determined. In embodiments, the expression of 15 proteins from Table 9 is determined. In embodiments, the expression of 16 proteins from Table 9 is determined. In embodiments, the expression of 17 proteins from Table 9 is determined. In embodiments, the expression of 18 proteins from Table 9 is determined. In embodiments, the expression of 19 proteins from Table 9 is determined. In embodiments, the expression of 20 proteins from Table 9 is determined. In embodiments, the expression of 21 proteins from Table 9 is determined. In embodiments, the expression of 22 proteins from Table 9 is determined. In embodiments, the expression of 23 proteins from Table 9 is determined.

In embodiments, the gene or protein level of one or more of CD68, CD163, LBP, CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1B, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18 is increased (compared to a control) in a biological sample from a subject having or suspected of having cancer.

In embodiments, the gene or protein level of one or more of CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18 is increased (compared to a control) in a biological sample from a subject having or suspected of having cancer. In embodiments, the gene or protein level of one or more of BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18 is increased (compared to a control) in a biological sample from a subject having or suspected of having cancer. In an embodiment, a subject having a high level of any one or more of these genes/proteins (compared to a control) is administered an adenosine pathway inhibitor.

In embodiments, the gene or protein level of one or more of CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA is decreased (compared to a control) in a biological sample from a subject having or suspected of having cancer. In embodiments, the gene or protein level of one or more of AKT3, BMI1, CD164, CD34, CD36, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, VEGFA, APP, ATG10, BCL2, CCL15, CD24, CD46, CD59, CDH1, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, MIF, PPARG, RORA, RORC, SPA17, STAT5B, TLR3, and/or TOLLIP is decreased (compared to a control) in a biological sample from a subject having or suspected of having cancer. In an embodiment, a subject having a low level of any one or more of these genes/proteins (compared to a control) is administered an adenosine pathway inhibitor.

In embodiments, the gene or protein level of CCL20 is increased (compared to a control) in a biological sample from a subject having or suspected of having cancer. In embodiments, the gene or protein level of CX3CL1 is decreased (compared to a control) in a biological sample from a subject having or suspected of having cancer. In embodiments, the gene or protein level of CCL20 is increased (compared to a control) and the gene or protein level of CX3CL1 is decreased (compared to a control) in a biological sample from a subject having or suspected of having cancer. In an embodiment, a subject having a high level of CCL20 and/or low level of CX3CL1 (compared to a control) is administered an adenosine pathway inhibitor.

In embodiments, the gene or protein level of IL6 is increased (compared to a control) in a biological sample from a subject having or suspected of having cancer. In an embodiment, a subject having a high level of IL6 (compared to a control) is administered an adenosine pathway inhibitor.

In embodiments, the gene or protein level of CD68 is increased (compared to a control) in a biological sample from a subject having or suspected of having cancer. In an embodiment, a subject having a high level of CD68 (compared to a control) is administered an adenosine pathway inhibitor.

In embodiments, the gene or protein level of CD163 is increased (compared to a control) in a biological sample from a subject having or suspected of having cancer. In an embodiment, a subject having a high level of CD163 (compared to a control) is administered an adenosine pathway inhibitor.

In embodiments, the gene(s) or protein(s) are down-regulated in a tumor (or tumor cell) in response to adenosine. In embodiments, the gene(s) or protein(s) are up-regulated in a tumor (or tumor cell) in response to adenosine. In embodiments, the gene(s) or protein(s) are down-regulated in an immune cell in response to adenosine. In embodiments, the gene(s) or protein(s) are up-regulated in an immune cell in response to adenosine. In embodiments, the immune cell is a peripheral blood mononuclear cell (PBMC) or a granulocyte. In embodiments, the PBMC is a T cell, a B cell, or a natural killer cell. In embodiments, the granulocyte is a neutrophil, a basophil, or an eosinophil.

TABLE 1

Genes/Proteins Down-Regulated by Adenosine Pathway and/or Anti-correlated With Adenosine Pathway in Tumors

| | |
|---|---|
| AKT3 | Protein kinase Akt-3 |
| APP | amyloid precursor protein |
| ATG10 | Autophagy Related 10 |
| BCL2 | B-cell lymphoma 2 |
| BMI1 | BMI1 proto-oncogene, polycomb ring finger |
| CCL15 | C-C motif chemokine ligand 15 |
| CCL24 | C-C motif chemokine ligand 24 |
| CCNE1 | Cyclin E1 |
| CD164 | cluster of differentiation 164 |
| CD24 | cluster of differentiation 24 |
| CD34 | cluster of differentiation 34 |
| CD36 | cluster of differentiation 36 |
| CD46 | cluster of differentiation 46 |
| CD59 | cluster of differentiation 59 |
| CDH1 | cadherin 1 |
| CDH5 | cadherin 5 |
| CREB1 | cAMP responsive element binding protein 1 |
| CREB5 | cAMP responsive element binding protein 5 |
| CX3CL1 | C-X3-C motif chemokine ligand 1 |
| CXCL14 | C-X-C Motif Chemokine Ligand 14 |
| CYFIP2 | cytoplasmic FMR1 interacting protein 2 |
| DEFB1 | defensin beta 1 |
| DOCK9 | dedicator of cytokinesis 9 |
| DPP4 | dipeptidyl peptidase 4 |
| ECSIT | ECSIT signalling integrator |
| EHF | ETS homologous factor |
| ENG | endoglin |
| EPCAM | epithelial cell adhesion molecule |
| FUT7 | fucosyltransferase 7 |
| GALM | galactose mutarotase |
| GBP6 | guanylate binding protein family member 6 |
| HMGB1 | high mobility group box 1 |
| IFIT1 | interferon induced protein with tetratricopeptide repeats 1 |
| IGF1R | insulin like growth factor 1 receptor |
| IL5 | Interleukin 5 |
| ITGA1 | integrin subunit alpha 1 |

TABLE 1-continued

Genes/Proteins Down-Regulated by Adenosine Pathway and/or Anti-correlated With Adenosine Pathway in Tumors

| | |
|---|---|
| ITGA6 | integrin subunit alpha 6 |
| ITGB3 | integrin subunit beta 3 |
| JAM3 | junctional adhesion molecule 3 |
| LAP3 | leucine aminopeptidase 3 |
| MAF | MAF bZIP transcription factor |
| MAP2K4 | mitogen-activated protein kinase kinase 4 |
| MAPK1 | mitogen-activated protein kinase 1 |
| MAPK3 | mitogen-activated protein kinase 3 |
| MAPK8 | mitogen-activated protein kinase 8 |
| MASP1 | mannan binding lectin serine peptidase 1 |
| MCAM | melanoma cell adhesion molecule |
| MFGE8 | milk fat globule-EGF factor 8 protein |
| MIF | macrophage migration inhibitory factor |
| MRPL11 | mitochondrial ribosomal protein L11 |
| NOTCH1 | notch 1 |
| NRP1 | neuropilin 1 |
| OST4 | olichyl-diphosphoologosaccharide—protein glycotransferase OST4 |
| PPARG | peroxisome proliferator activated receptor gamma |
| PRKCE | protein kinase C epsilon |
| RORA | RAR-related orphan receptor alpha |
| RORC | RAR related orphan receptor C |
| SMAD2 | SMAD family member 2 |
| SPA17 | sperm autoantigenic protein 17 |
| STAT5B | signal transducer and activator of transcription 5B |
| TAL1 | T-cell acute lymphocytic leukemia protein 1 |
| TBX21 | T-box 21 |
| THY1 | Thy-1 cell surface antigen |
| TLR3 | toll like receptor 3 |
| TNFSF12 | TNF superfamily member 12 |
| TOLLIP | toll interacting protein |
| TRAF6 | TNF receptor associated factor 6 |
| TXNIP | thioredoxin interacting protein |
| VEGFA | vascular endothelial growth factor A |
| WDR83OS | WD repeat domain 83 opposite strand |

TABLE 2

Genes/Proteins Up-Regulated by Adenosine Pathway and/or Correlated With Adenosine Pathway in Tumors

| | |
|---|---|
| ADA | adenosine deaminase |
| ALCAM | activated leukocyte cell adhesion molecule |
| BCL6 | B-cell lymphoma 6 |
| BIRC5 | Baculoviral IAP Repeat Containing 5 |
| BST1 | Bone Marrow Stromal Cell Antigen 1 |
| C1R | COMPLEMENT COMPONENT 1, r SUBCOMPONENT |
| C1S | complement component 1, s subcomponent |
| C2 | complement component 2 |
| C4BPA | Complement Component 4 Binding Protein Alpha |
| C9 | Complement component 9 |
| CARD11 | caspase recruitment domain family member 11 |
| CCDC60 | Coiled-Coil Domain Containing 60 |
| CCL11 | C-C motif chemokine ligand 11 |
| CCL2 | C-C motif chemokine ligand 2 |
| CCL20 | C-C motif chemokine ligand 20 |
| CCL3 | C-C motif chemokine ligand 3 |
| CCL7 | C-C motif chemokine ligand 7 |
| CCL8 | C-C motif chemokine ligand 8 |
| CCR6 | C-C motif chemokine receptor 6 |
| CD14 | cluster of differentiation 14 |
| CD300E | CD300 antigen-like family member E |
| CD86 | Cluster of Differentiation 86 |
| CD93 | Cluster of Differentiation 93 |
| CD63 | Cluster of Differentiation 63 |
| CD168 | Cluster of Differentiation 168 |
| CDK1 | cyclin dependent kinase 1 |
| CEACAM6 | carcinoembryonic antigen related cell adhesion molecule 6 |
| CEBPB | CCAAT enhancer binding protein beta |
| CFD | complement factor D |
| CLEC5A | C-type lectin domain family 5 member A |
| CSF1 | colony stimulating factor 1 |

TABLE 2-continued

Genes/Proteins Up-Regulated by Adenosine Pathway and/or Correlated With Adenosine Pathway in Tumors

| | |
|---|---|
| CSF2RB | colony stimulating factor 2 receptor beta common subunit |
| CSF3 | Colony Stimulating Factor 3 |
| CT45A1 | cancer/testis antigen family 45 member A1 |
| CXCL1 | C-X-C Motif Chemokine Ligand 1 |
| CXCL16 | C-X-C Motif Chemokine Ligand 16 |
| CXCL2 | C-X-C Motif Chemokine Ligand 2 |
| CXCL3 | C-X-C Motif Chemokine Ligand 3 |
| CXCL5 | C-X-C Motif Chemokine Ligand 5 |
| CXCL6 | C-X-C Motif Chemokine Ligand 6 |
| CXCL8 | C-X-C Motif Chemokine Ligand 8 |
| CXCR1 | C-X-C motif chemokine receptor 1 |
| CXCR2 | C-X-C motif chemokine receptor 2 |
| CXCR4 | C-X-C motif chemokine receptor 4 |
| DFNA5 | gasdermin E |
| DMBT1 | deleted in malignant brain tumors 1 |
| ECEL1 | Endothelin Converting Enzyme Like 1 |
| EML6 | Echinoderm Microtubule Associated Protein Like 6 |
| EMR3 | EGF-like module-containing mucin-like hormone receptor-like 3 |
| EPB41L3 | erythrocyte membrane protein band 4.1 like 3 |
| FCGR2A | Fc fragment of IgG receptor IIa |
| FOXJ1 | forkhead box J1 |
| GPR157 | G Protein-Coupled Receptor 157 |
| HAMP | hepcidin antimicrobial peptide |
| HAS1 | hyaluronan synthase 1 |
| HSD11B1 | hydroxysteroid 11-beta dehydrogenase 1 |
| IFI16 | interferon gamma inducible protein 16 |
| IL1A | Interleukin 1 Alpha |
| IL 1B | Interleukin 1 Beta |
| IL23A | Interleukin 23 Subunit Alpha |
| IL24 | Interleukin 24 |
| IL6 | Interleukin 6 |
| IL8 | Interleukin 8 |
| INHBA | Inhibin Beta A |
| IRAK4 | interleukin 1 receptor associated kinase 4 |
| ITCH | itchy E3 ubiquitin protein ligase |
| ITGAM | integrin subunit alpha M |
| KLC4 | Kinesin Light Chain 4 |
| LAYN | Layilin |
| LBP | Lipopolysaccharide Binding Protein |
| LIF | leukemia inhibitory factor |
| LOC100505585 | |
| LY96 | lymphocyte antigen 96 |
| LYN | LYN proto-oncogene, Src family tyrosine kinase |
| MAP2K2 | mitogen-activated protein kinase kinase 2 |
| MS4A7 | Membrane Spanning 4-Domains A7 |
| NID1 | nidogen 1 |
| NPR1 | Natriuretic Peptide Receptor 1 |
| PADI2 | Peptidyl Arginine Deiminase 2 |
| PID1 | Phosphotyrosine Interaction Domain Containing 1 |
| PLAUR | plasminogen activator, urokinase receptor |
| PPBP | Pro-Platelet Basic Protein |
| PRAME | preferentially expressed antigen in melanoma |
| PSMD7 | proteasome 26S subunit, non-ATPase 7 |
| PTGS2 | Prostaglandin-endoperoxide synthase |
| RHCG | Rh Family C Glycoprotein |
| RIPK2 | receptor interacting serine/threonine kinase 2 |
| SAA1 | serum amyloid A1 |
| SERPINB2 | serpin family B member 2 |
| SLC11A1 | Natural resistance-associated macrophage protein 1 |
| SLC7A7 | Solute Carrier Family 7 Member 7 |
| SPON1 | Spondin 1 |
| ST6GALNAC2 | ST6 N-Acetylgalactosaminide Alpha-2,6-Sialyltransferase 2 |
| STAT2 | signal transducer and activator of transcription 2 |
| STAT3 | signal transducer and activator of transcription 3 |
| SYTL3 | Synaptotagmin Like 3 |
| TFRC | transferrin receptor |
| TGIF1 | TGFB Induced Factor Homeobox 1 |
| THBS1 | Thrombospondin 1 |
| TLR5 | toll like receptor 5 |
| TNFRSF11A | TNF receptor superfamily member 11a |
| TNFSF14 | TNF superfamily member 14 |
| TNFSF18 | TNF superfamily member 18 |
| TNFSF4 | TNF superfamily member 4 |
| TREM1 | triggering receptor expressed on myeloid cells 1 |
| TREM2 | triggering receptor expressed on myeloid cells 2 |
| TTK | TTK protein kinase |
| ZBTB18 | Zinc Finger and BTB Domain Containing 18 |
| S100A8 | S100 calcium binding protein A8 |
| ERRG | estrogen related receptor gamma |

In embodiments, one or more of the genes or proteins listed in Table 1 or Table 2 is not detected. That is, any gene or protein disclosed herein may be specifically excluded from the method.

In embodiments, the gene or protein to be detected is selected from CCL2, CCL3, CCL7, CCL24, CCNE1, CD14, CD300E, CD86, CD93, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, IL1A, IL-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, and/or WDR83OS.

In embodiments, the gene or protein to be detected is selected from CCL2, CCL3, CCL7, CD300E, CD93, CSF3, CXCL1, CXCL2, CXCL3, CXCL5, CXCL8, ECEL1, HAS1, IL-1β, IL8, IL23, INHBA, PADI2, PID1, PTGS2, SCL747, SERPINB2, ST6GALNAC2, and/or THBS1.

In embodiments, the gene or protein to be detected is selected from CXCL1, CXCL2, CXCL3, CXCL5, SERPINB2, IL8, and/or IL-1β.

In embodiments, genes are selected from IL1β, PTGS2, CXCL1, CXCL2, CXCL3, CXCL5, CXCL6, and CXCL8.

In embodiments, the gene or protein to be detected is selected from CCL24, CCNE1, EHF, FUT7, GALM, GBP6, IL5, LAP3, MRPL11, OST4, WDR83OS, and/or TBX21.

In embodiments, the gene or protein to be detected is selected from EHF, FUT7, and/or OST4.

In embodiments, the gene or protein to be detected is selected from CXCL1, CXCL2, CXCL3, CXCL5, SERPINB2, IL8, and/or IL1B. This group of genes/proteins may be referred to as the "adenosine composite gene expression module."

It is further contemplated that expression of CCL20 can be used to determine whether a tumor may be susceptible to treatment with an adenosine pathway inhibitor. In an embodiment, expression of CX3CL1 can be used. In an embodiment, tumors that highly express CCL20, but not CX3CL1, are expected to be susceptible to treatment with an adenosine pathway inhibitor.

In embodiments, the gene or protein to be detected is selected from C1R, C1S, C4BPA, CCL11, CCL20, CXCL16, CXCL2, HAMP, HSD11B1, ITGAM, LIF, S100A8, SAA1, SLC11A1, TFRC, TLR5, TNFSF14, and/or TREM2. This group of genes/proteins may be referred to as the "adenosine signature gene module." These genes may be co-regulated with one or more additional genes described herein, for example and without limitation, CXCL1, CXCL2, CXCL3, CXCL5, SERPINB2, IL8, and/or IL1B. Functionally, co-regulated genes include complement, chemokines, and markers of myeloid cells. In embodiments, a level of expression of the one or more genes (or proteins) that is higher than a control indicates that the subject is a candidate for treatment with an adenosine pathway inhibitor (e.g., ADORA2A antagonist).

In embodiments, the gene or protein to be detected is selected from APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, and/or TOLLIP. This group of genes/proteins may be referred to as the "CX3CL1 Gene Module." Expression of these genes may be negatively correlated with expression of one or more additional genes or proteins as described herein, for example and without limitation, CXCL1, CXCL2, CXCL3, CXCL5, SERPINB2, IL8, and/or IL1B. Functionally, negatively correlated genes/proteins include elements of complement regulation and MAPK pathway signaling. In embodiments, a level of expression of the one or more genes (or proteins) that is lower than a control indicates that the subject is a candidate for treatment with an adenosine pathway inhibitor (e.g., ADORA2A antagonist).

In embodiments, the gene or protein to be detected is selected from AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, and/or VEGFA. This group of genes/proteins may be referred to as the "growth factor module." Expression of these genes may be negatively correlated with expression of one or more additional genes or proteins as described herein, for example and without limitation, CXCL1, CXCL2, CXCL3, CXCL5, SERPINB2, IL8, and/or IL1β. Functionally, negatively correlated genes/proteins include the Reactome pathway database as being enriched for signaling by FGFR, EGFR, NGF, and ERBB2. In embodiments, a level of expression of the one or more genes (or proteins) that is lower than a control indicates that the subject is a candidate for treatment with an adenosine pathway inhibitor (e.g., ADORA2A antagonist).

In an aspect is provided a method for detecting a level of expression of one or more genes in a subject having or suspected of having cancer. In an embodiment, the method includes (a) obtaining a biological sample from the subject; and (b) detecting the level of expression of one or more genes selected from ACTBL2, ADAM8, ALOX5AP, ANXA2P2, AQP9, AREG, ARHGAP9, BCL2A1, BCL3, BDKRB2, BIRC3, C10orf55, C15orf48, C19orf59, C1orf38, C1R, C1S, C3, C5AR1, C8orf4, CASP4, CCL18, CCL2, CCL20, CCL3, CCL3L1, CCL4, CCL4L2, CCL7, CCL8, CCR1, CD14, CD300A, CD300E, CD300LB, CD53, CD69, CD86, CDCP1, CEACAM3, CFB, CLEC4A, CLEC4D, CLEC4E, CLEC5A, CLEC7A, CSF2, CSF2RB, CSF3, CSF3R, CXCL1, CXCL2, CXCL3, CXCL5, CXCL6, CXCR1, CXCR2, CXorf21, CYR61, CYTH4, CYTIP, DAPP1, DUSP1, DUSP5, EGR3, EMP1, EMR2, EMR3, EREG, F3, FCAR, FCER1G, FCGR2A, FCGR2B, FCGR3B, FFAR2, FGR, FOS, FOSL1, FPR1, FPR2, GOS2, GLIPR1, GNA15, GPR109A, GPR109B, GPR183, GPR84, GPR97, GPRC5A, HAS1, HBEGF, HCK, HK3, ICAM1, IER3, IL10, IL1A, IL1B, IL1R2, IL1RL1, IL1RN, IL4R, IL6, IL7R, IL8, JUNB, KLF6, LAMC2, LCP2, LIF, LILRA5, LILRA6, LILRB2, LILRB3, LRG1, LYN, MAFF, MAP3K8, MCL1, MEFV, MMP1, MMP12, MMP3, MMP7, MNDA, MYO1G, NAMPT, NCF2, NCF4, NCOA7, NFE2, NFKBIZ, NLRP3, NNMT, OBFC2A, OSM, OSMR, P2RY6, PF4V1, PHLDA1, PI3, PLAU, PLAUR, PLEK, PLK3, PPBP, PPPIR15A, PRDM1, PTGS2, PTPN22, RARRES1, RASGRP4, RGS1, RGS2, RND1, RND3, S100A12, S100A8, S100A9, SAA1, SAA2, SAA4, SAMSN1, SAT1, SELE, SERPINA1, SERPINB2, SERPINB4, SERPINB7, SERPINB8, SERPINE1, SLC11A1, SLC2A14, SLC2A3, SNAI1, SOCS3, SOD2, SPI1, SRGN, STX11, TDO2, TGM2, THBS1, TLR2, TNF, TNFAIP2, TNFAIP3, TNFAIP6, TNIP3, TREM1, VNN1, VNN2, VNN3, ZC3H12A, ZFP36 in the biological sample. In embodiments, the method further includes (c) comparing the level of expression of the one or more genes in the sample to a level of expression of the one or more genes in a suitable control. In embodiments, the suitable control is a sample from a healthy subject, a sample from a non-cancerous tissue, or an average level of expression in a population.

In an aspect is provided a method treating a subject having cancer. In an embodiment, the method includes (a) obtaining a biological sample from the subject; (b) detecting a level of expression of one or more genes selected from ACTBL2, ADAM8, ALOX5AP, ANXA2P2, AQP9, AREG, ARHGAP9, BCL2A1, BCL3, BDKRB2, BIRC3, C10orf55, C15orf48, C19orf59, C1orf38, C1R, C1S, C3, C5AR1, C8orf4, CASP4, CCL18, CCL2, CCL20, CCL3, CCL3L1, CCL4, CCL4L2, CCL7, CCL8, CCR1, CD14, CD300A, CD300E, CD300LB, CD53, CD69, CD86, CDCP1, CEACAM3, CFB, CLEC4A, CLEC4D, CLEC4E, CLEC5A, CLEC7A, CSF2, CSF2RB, CSF3, CSF3R, CXCL1, CXCL2, CXCL3, CXCL5, CXCL6, CXCR1, CXCR2, CXorf21, CYR61, CYTH4, CYTIP, DAPP1, DUSP1, DUSP5, EGR3, EMP1, EMR2, EMR3, EREG, F3, FCAR, FCER1G, FCGR2A, FCGR2B, FCGR3B, FFAR2, FGR, FOS, FOSL1, FPR1, FPR2, GOS2, GLIPR1, GNA15, GPR109A, GPR109B, GPR183, GPR84, GPR97, GPRC5A, HAS1, HBEGF, HCK, HK3, ICAM1, IER3, IL10, IL1A, IL1B, IL1R2, IL1RL1, IL1RN, IL4R, IL6, IL7R, IL8, JUNB, KLF6, LAMC2, LCP2, LIF, LILRA5, LILRA6, LILRB2, LILRB3, LRG1, LYN, MAFF, MAP3K8, MCL1, MEFV, MMP1, MMP12, MMP3, MMP7, MNDA, MYO1G, NAMPT, NCF2, NCF4, NCOA7, NFE2, NFKBIZ, NLRP3, NNMT, OBFC2A, OSM, OSMR, P2RY6, PF4V1, PHLDA1, PI3, PLAU, PLAUR, PLEK, PLK3, PPBP, PPPIR15A, PRDM1, PTGS2, PTPN22, RARRES1, RASGRP4, RGS1, RGS2, RND1, RND3, S100A12, S100A8, S100A9, SAA1, SAA2, SAA4, SAMSN1, SAT1, SELE, SERPINA1, SERPINB2, SERPINB4, SERPINB7, SERPINB8, SERPINE1, SLC11A1, SLC2A14, SLC2A3, SNAI1, SOCS3, SOD2, SPI1, SRGN, STX11, TDO2, TGM2, THBS1, TLR2, TNF, TNFAIP2, TNFAIP3, TNFAIP6, TNIP3, TREM1, VNN1, VNN2, VNN3, ZC3H12A, and/or ZFP36 in the biological sample; and (c) administering to the subject an effective amount of an adenosine pathway inhibitor, thereby treating the cancer. In embodiments, the method includes comparing the level of expression of the one or more genes in the sample to a level of expression of the one or more genes in a suitable control. In embodiments, the suitable control is a sample from a healthy subject, a sample from a non-cancerous tissue, or an average level of expression in a population.

In embodiments, the adenosine pathway inhibitor is an A2A receptor (ADORA2A) antagonist. In embodiments, the ADORA2A antagonist is CPI-444. In embodiments, the adenosine pathway inhibitor is is a CD73 antagonist, a CD38 antagonist, a CD39 antagonist, or adenosine deaminase. In embodiments, the CD73 antagonist is an anti-CD73 antibody.

In an aspect is provided a method of identifying a subject for treatment with an adenosine pathway inhibitor. In an embodiment, the subject has or is suspected of having cancer. In embodiments, the method includes (a) obtaining a biological sample from the subject; and (b) detecting a level of expression of one or more genes selected from ACTBL2, ADAM8, ALOX5AP, ANXA2P2, AQP9, AREG, ARHGAP9, BCL2A1, BCL3, BDKRB2, BIRC3, C10orf55, C15orf48, C19orf59, C1orf38, C1R, C1S, C3, C5AR1, C8orf4, CASP4, CCL18, CCL2, CCL20, CCL3, CCL3L1, CCL4, CCL4L2, CCL7, CCL8, CCR1, CD14, CD300A, CD300E, CD300LB, CD53, CD69, CD86, CDCP1, CEACAM3, CFB, CLEC4A, CLEC4D, CLEC4E, CLEC5A, CLEC7A, CSF2, CSF2RB, CSF3, CSF3R, CXCL1, CXCL2, CXCL3, CXCL5, CXCL6, CXCR1, CXCR2, CXorf21, CYR61, CYTH4, CYTIP, DAPP1, DUSP1, DUSP5, EGR3, EMP1, EMR2, EMR3, EREG, F3, FCAR, FCER1G, FCGR2A, FCGR2B, FCGR3B, FFAR2, FGR, FOS, FOSL1, FPR1, FPR2, GOS2, GLIPR1, GNA15, GPR109A, GPR109B, GPR183, GPR84, GPR97, GPRC5A, HAS1, HBEGF, HCK, HK3, ICAM1, IER3, IL10, IL1A, IL1B, IL1R2, IL1RL1, IL1RN, IL4R, IL6, IL7R, IL8, JUNB, KLF6, LAMC2, LCP2, LIF, LILRA5, LILRA6, LILRB2, LILRB3, LRG1, LYN, MAFF, MAP3K8, MCL1, MEFV, MMP1, MMP12, MMP3, MMP7, MNDA, MYO1G, NAMPT, NCF2, NCF4, NCOA7, NFE2, NFKBIZ, NLRP3, NNMT, OBFC2A, OSM, OSMR, P2RY6, PF4V1, PHLDA1, PI3, PLAU, PLAUR, PLEK, PLK3, PPBP, PPPIR15A, PRDM1, PTGS2, PTPN22, RARRES1, RASGRP4, RGS1, RGS2, RND1, RND3, S100A12, S100A8, S100A9, SAA1, SAA2, SAA4, SAMSN1, SAT1, SELE, SERPINA1, SERPINB2, SERPINB4, SERPINB7, SERPINB8, SERPINE1, SLC11A1, SLC2A14, SLC2A3, SNAI1, SOCS3, SOD2, SPI1, SRGN, STX11, TDO2, TGM2, THBS1, TLR2, TNF, TNFAIP2, TNFAIP3, TNFAIP6, TNIP3, TREM1, VNN1, VNN2, VNN3, ZC3H12A, and/or ZFP36 in the biological sample. In embodiments, a level of expression that is higher than a suitable control indicates that the subject is a candidate for treatment with the adenosine pathway inhibitor. In embodiments, the suitable control is a sample from a healthy subject, a sample from a non-cancerous tissue, or an average level of expression in a population.

In an aspect is provided a method of selecting a subject for treatment with an adenosine pathway inhibitor, said subject having or suspected of having cancer, the method comprising: (a) obtaining a biological sample from the subject; (b) detecting a high level of expression of one or more genes or proteins selected from ACTBL2, ADAM8, ALOX5AP, ANXA2P2, AQP9, AREG, ARHGAP9, BCL2A1, BCL3, BDKRB2, BIRC3, C10orf55, C15orf48, C19orf59, C1orf38, C1R, C1S, C3, C5AR1, C8orf4, CASP4, CCL18, CCL2, CCL20, CCL3, CCL3L1, CCL4, CCL4L2, CCL7, CCL8, CCR1, CD14, CD300A, CD300E, CD300LB, CD53, CD69, CD86, CDCP1, CEACAM3, CFB, CLEC4A, CLEC4D, CLEC4E, CLEC5A, CLEC7A, CSF2, CSF2RB, CSF3, CSF3R, CXCL1, CXCL2, CXCL3, CXCL5, CXCL6, CXCR1, CXCR2, CXorf21, CYR61, CYTH4, CYTIP, DAPP1, DUSP1, DUSP5, EGR3, EMP1, EMR2, EMR3, EREG, F3, FCAR, FCER1G, FCGR2A, FCGR2B, FCGR3B, FFAR2, FGR, FOS, FOSL1, FPR1, FPR2, GOS2, GLIPR1, GNA15, GPR109A, GPR109B, GPR183, GPR84, GPR97, GPRC5A, HAS1, HBEGF, HCK, HK3, ICAM1, IER3, IL10, ILIA, IL1B, IL1R2, IL1RL1, IL1RN, IL4R, IL6, IL7R, IL8, JUNB, KLF6, LAMC2, LCP2, LIF, LILRA5, LILRA6, LILRB2, LILRB3, LRG1, LYN, MAFF, MAP3K8, MCL1, MEFV, MMP1, MMP12, MMP3, MMP7, MNDA, MYO1G, NAMPT, NCF2, NCF4, NCOA7, NFE2, NFKBIZ, NLRP3, NNMT, OBFC2A, OSM, OSMR, P2RY6, PF4V1, PHLDA1, PI3, PLAU, PLAUR, PLEK, PLK3, PPBP, PPPIR15A, PRDM1, PTGS2, PTPN22, RARRES1, RASGRP4, RGS1, RGS2, RND1, RND3, S100A12, S100A8, S100A9, SAA1, SAA2, SAA4, SAMSN1, SAT1, SELE, SERPINA1, SERPINB2, SERPINB4, SERPINB7, SERPINB8, SERPINE1, SLC11A1, SLC2A14, SLC2A3, SNAI1, SOCS3, SOD2, SPI1, SRGN, STX11, TDO2, TGM2, THBS1, TLR2, TNF, TNFAIP2, TNFAIP3, TNFAIP6, TNIP3, TREM1, VNN1, VNN2, VNN3, ZC3H12A, and/or ZFP36 in the biological sample; and (c) selecting the subject for treatment with the adenosine pathway inhibitor.

In embodiments, a "high level" of expression is a level of expression of the gene or protein that is higher than the level of expression of the gene or protein in a control. The control may be any suitable control, examples of which are described herein.

In embodiments, a "low level" of expression is a level of expression of the gene or protein that is lower than the level of expression of the gene or protein in a control. The control may be any suitable control, examples of which are described herein.

In embodiments, gene(s) or protein(s) other than those listed herein are not detected. any one of the genes or proteins listed herein may be explicitly excluded from a list of gene(s) or protein(s) that are detected in a method described herein.

RNA may be detected by any known methodology, including but not limited to rtPCR, RNA sequencing, nanopore sequencing, microarray, hybridization-based sequencing, hybridization-based detection and quantification (e.g., NanoString).

Protein may be detected by any known methodology, including but not limited to high-performance liquid chromatography (HPLC); mass spectrometry (MS), e.g., Liquid chromatography-mass spectrometry; Enzyme-linked immunosorbent assay (ELISA); Protein immunoprecipitation; immunoelectrophoresis; Western blot; protein immunostaining; immunofluorescence; mass cytometry; immunohistochemistry.

In embodiments, tumors that express the genes of the Adenosine composite gene expression or Adenosine Signature Gene Module, or a subset of those genes, or genes in the pathways represented by the Adenosine Signature Gene Module, may define patients to be treated with an antagonist of the adenosine pathway. In embodiments, such tumors are enriched in adenosine.

In embodiments, tumors that demonstrate low levels of expression of the genes of the Growth Factor Gene Module, or a subset of those genes, or genes in the pathways represented by the Growth Factor Gene Module, may define patients to be treated with an antagonist of the adenosine pathway. In embodiments, such tumors are enriched in adenosine.

In embodiments, tumors that demonstrate low levels of expression of the genes of the CXCL1 Gene Module, or a subset of those genes, or genes in the pathways represented by the CXCL1 Gene Module, may define patients to be treated with an antagonist of the adenosine pathway. In embodiments, such tumors are enriched in adenosine.

In embodiments, the adenosine pathway is inhibited by an antagonist of A2AR, such as CPI-444.

In embodiments, the adenosine pathway would be inhibited by an antagonist of A2BR. In embodiments, the adenosine pathway is inhibited by a CD73 antagonist. In embodiments, the CD73 antagonist is an anti-CD73 antibody. In embodiments, the adenosine pathway is inhibited by a CD38 antagonist. In embodiments, the adenosine pathway is inhibited by a CD39 antagonist. In embodiments, the adenosine pathway is inhibited by adenosine deaminase.

III. Methods

Methods of Detecting Biomarker(s)

The present disclosure relates to methods for detecting a level of expression of one or more genes or proteins (as described above) in a subject having or suspected of having cancer, comprising detecting the level of expression of the one or more genes in a biological sample from the subject. Without being bound by theory, it is believed that the expression level of one or more of the genes or proteins indicates a level of activation of the adenosine pathway in the subject (or in the cancer) and the susceptibility of the cancer to treatment with an inhibitor of the adenosine pathway.

In embodiments, the method further comprises comparing the level of expression of the one or more genes or proteins in the sample to a level of expression of the one or more genes or proteins in a suitable control.

In embodiments is provided a method for detecting a level of expression of one or more genes (or proteins) in a subject having or suspected of having cancer, the method comprising: (a) obtaining a biological sample from the subject; and (b) detecting the level of expression of the one or more genes (or proteins) in the biological sample, wherein the one or more genes (or proteins) is selected from those listed in Table 1. In embodiments, the method further comprises (c) comparing the level of expression of the one or more genes (or proteins) in the sample to a level of expression of the one or more genes (or proteins) in a suitable control.

In embodiments, a level of expression of the one or more genes or proteins that is higher than a control indicates that the subject is a candidate for treatment with an adenosine pathway inhibitor (e.g., ADORA2A antagonist). In embodiments, the gene or protein to be detected is selected from CD68, CD163, LBP, IL6, CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18. In embodiments, the gene or protein to be detected is selected from IL6, CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18. In embodiments, the gene or protein to be detected is selected from CCL2, CCL3, CCL7, CD300E, CD93, CSF3, CXCL1, CXCL2, CXCL3, CXCL5, CXCL8, ECEL1, HAS1, IL-1β, IL8, IL23, INHBA, PADI2, PID1, PTGS2, SCL747, SERPINB2, ST6GALNAC2, and/or THBS1. In embodiments, the gene or protein to be detected is selected from CXCL1, CXCL2, CXCL3, CXCL5, SERPINB2, IL8, and/or IL1β. In embodiments, the gene or protein to be detected is selected from C1R, C1S, C4BPA, CCL11, CCL20, CXCL16, CXCL2, HAMP, HSD11B1, ITGAM, LIF, S100A8, SAA1, SLC11A1, TFRC, TLR5, TNFSF14, and/or TREM2. In an embodiment, the gene or protein to be detected is CCL20. In an embodiment, the gene or protein to be detected is IL6. In an embodiment, the gene or protein to be detected is IL8.

In embodiments, a level of expression of the one or more genes or proteins that is lower than a control indicates that the subject is a candidate for treatment with an adenosine pathway inhibitor (e.g., ADORA2A antagonist). In embodiments, the genes or proteins are selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA. In embodiments, the genes or proteins are selected from CCL24, CCNE1, EHF, FUT7, GALM, GBP6, IL5, LAP3, MRPL11, OST4, WDR83OS, and/or TBX21. In embodiments, the genes or proteins are selected from APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, and/or TOLLIP. In embodiments, the genes or proteins are selected from AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, and/or VEGFA. In an embodiment, the gene or protein to be detected is CX3CL1.

Methods of Treatment

The present disclosure further relates to a method of treating a subject having cancer, the method comprising: obtaining a biological sample from the subject; detecting a level of expression of one or more genes or proteins (as described above) in the biological sample; and administering to the subject an effective amount of an adenosine pathway inhibitor (e.g., ADORA2A antagonist), thereby treating the cancer.

The present disclosure further relates to a method of identifying a subject for treatment with an adenosine pathway inhibitor (e.g., ADORA2A antagonist), said subject having or suspected of having cancer, the method comprising: obtaining a biological sample from the subject; and detecting a level of expression of one or more genes or proteins in the biological sample; wherein a level of expression of the one or more genes or proteins that is higher than a control indicates that the subject is a candidate for treatment with an adenosine pathway inhibitor (e.g., ADORA2A antagonist). In embodiments, the genes or proteins are selected from CD68, CD163, LBP, CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18. In embodiments, the genes or proteins are selected from CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18. In embodiments, the genes or proteins are selected from BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18. In embodiments, the genes or proteins are selected from CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, and/or THBS1. In embodiments, the gene or protein to be detected is selected from C1R, C1S, C4BPA, CCL11, CCL20, CXCL16, CXCL2, HAMP, HSD11B1, ITGAM, LIF, S100A8, SAA1, SLC11A1, TFRC, TLR5, TNFSF14, and/or TREM2. In embodiments, the gene or protein to be detected is selected from CXCL1, CXCL2, CXCL3, CXCL5, SERPINB2, IL8, and/or IL1B. In an embodiment, the gene or protein to be detected is CCL20. In an embodiment, the gene or protein to be detected is IL6.

The present disclosure further relates to a method of identifying a subject for treatment with an adenosine pathway inhibitor (e.g., ADORA2A antagonist), said subject having or suspected of having cancer, the method comprising: (a) obtaining a biological sample from the subject; and (b) detecting a level of expression of one or more genes or proteins in the biological sample; wherein a level of expression of the one or more genes or proteins that is lower than a control indicates that the subject is a candidate for treatment with an adenosine pathway inhibitor (e.g., ADORA2A antagonist). In embodiments, the genes or proteins to be detected is selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA. In embodiments, the genes or proteins to be detected is selected from CCL24, CCNE1, EHF, FUT7, GALM, GBP6, IL5, LAP3, MRPL11, OST4, WDR83OS, and/or TBX21. In embodiments, the genes or proteins to be detected are selected from APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, and/or TOLLIP. In embodiments, the genes or proteins to be detected are selected from AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, and/or VEGFA. In an embodiment, the gene or protein to be detected is selected from AKT3, BMI1, CD164, CD34, CD36, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, VEGFA, APP, ATG10, BCL2, CCL15, CD24, CD46, CD59, CDH1, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, MIF, PPARG, RORA, RORC, SPA17, STAT5B, TLR3, and/or TOLLIP. In an embodiment, the gene or protein to be detected is CX3CL1.

In embodiments is provided a method of treating a subject having cancer, the method comprising: (a) obtaining a biological sample from the subject; (b) detecting a level of expression of one or more genes or proteins in the biological sample, wherein the genes or proteins are selected from those listed in Table 1; and (c) administering to the subject an effective amount of an adenosine pathway inhibitor (e.g., ADORA2A antagonist) thereby treating the cancer.

In embodiments, the genes or proteins detected are selected from CCL24, CCNE1, EHF, FUT7, GALM, GBP6, IL5, LAP3, MRPL11, OST4, WDR83OS, and/or TBX21, and a level of expression of the one or more genes that is lower than a control indicates that the subject is a candidate for treatment with an adenosine pathway inhibitor (e.g., ADORA2A antagonist) i.

In embodiments is provided a method of treating a subject having cancer, the method comprising: (a) optionally obtaining a biological sample from the subject; (b) receiving an identification of a patient as having a reduced level of expression of one or more genes or proteins selected from CCL24, CCNE1, EHF, FUT7, GALM, GBP6, IL5, LAP3, MRPL11, OST4, WDR83OS, and/or TBX21 in a biological sample; and (c) administering to the subject an effective amount of an adenosine pathway inhibitor (e.g., ADORA2A antagonist), thereby treating the cancer.

In embodiments is provided a method of treating a subject having cancer, the method comprising: (a) optionally obtaining a biological sample from the subject; (b) receiving an identification of a patient as having an increased level of expression of one or more genes or proteins selected from CCL24, CCNE1, EHF, FUT7, GALM, GBP6, IL5, LAP3, MRPL11, OST4, WDR83OS, and/or TBX21 in a biological sample; and (c) administering to the subject an effective amount of an adenosine pathway inhibitor (e.g., ADORA2A antagonist), thereby treating the cancer.

In an aspect is provided a method of treating a subject having cancer, the method comprising: (a) obtaining a biological sample from the subject; (b) detecting a level of expression of CD163 and/or CD68 in the sample; and (c) administering to the subject an effective amount of an adenosine pathway inhibitor (e.g., ADORA2A antagonist), thereby treating the cancer. In embodiments, a level of CD163 and/or CD68 gene expression is detected. In embodiments, a level of CD163 and/or CD68 protein expression is detected. In embodiments, the adenosine pathway inhibitor is administered if the level of expression of CD163 and/or CD68 is higher than a control. In embodiments, a level of expression of at least one additional gene and/or protein is detected. In embodiments, the at least one additional gene and/or protein is selected from the genes/proteins listed in Table 1 and/or Table 2. In embodiments, the at least one additional gene and/or protein is selected from LBP, BIRC5, BST1, CARD11, CCL2, CCL3, CCL7, CCL24, CCNE1, CD14, CD300E, CD86, CD93, CDK1, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, IL1A, IL-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, C1R, C1S, C4BPA, CCL11, CCL20, CXCL16, CXCL2, HAMP, HSD11B1, ITGAM, LIF, SAA1, TFRC, TLR5, TNFRSF11A, TNFSF14, TREM1, TREM2, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, TNFSF18, APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CD36, CDH1, CDH5, CREB1, DOCK9, ENG, HMGB1, ITGA1, JAM3, MAF, MAPK3, MAPK8, MCAM, MFGE8, MIF, NOTCH1, NRP1, PRKCE, RORA, TLR3, SMAD2, TAL1, THY1, TNFSF12, TRAF6, TXNIP, VEGFA, S100A8, and/or WDR83OS.

In embodiments, the ADORA2A antagonist is CPI-444. In embodiments, the ADORA2A antagonist is AZD4635 (AstraZeneca), EVOEXS21546 (Exscientia-Evotec), AB928 (Arcus Biosciences), SEL330-475 (Selvita), EOS100850 (iTEOS), and PBF-509 (Palobiofarma SL).

Without being bound by theory, it is believed that high adenosine production by a tumor (high adenosine levels in the tumor microenvironment) leads to activation of the CXCR2 pathway (for example, by increasing expression of, e.g., CXCL1, CXCL2, CXCL5, and/or IL8 by the tumor), thereby recruiting neutrophils and myeloid-derived suppressor cells (MDSCs) into the tumor. Presence of these cells inhibits T cell infiltration of the tumor, and thus promotes an immune suppressive environment. Treatment of the tumor/subject with a CXCR2 inhibitor (e.g., anti-CXCR2 antibody) can inhibit the CXCR2 pathway and promote T cell infiltration into the tumor, promoting an immune permissive environment. In embodiments, sensitivity of the tumor to immunotherapy is increased. In embodiments, a method as described herein further comprises administering a CXCR2 inhibitor to the subject. In embodiments, the CXCR2 inhibitor is selected from AZD5069 (AstraZeneca), anti-CXCR2 antibody, Navarixin (MK-7123; Ligand Pharmaceuticals/Merck & Co.).

In some examples of the disclosed methods, when the expression level of a gene/protein or a subset of genes/proteins is assessed, the expression level is compared with a control expression level of the gene(s) and/or protein(s). By control expression level is meant the expression level of the gene(s) and/or protein(s) from a sample or subject lacking cancer, a sample or subject at a selected stage of cancer or cancer state, or in the absence of a particular variable such as a therapeutic agent. Alternatively, the control level comprises a known amount of the gene(s) and/or protein(s). Such a known amount correlates with an average level of subjects lacking cancer, at a selected stage of cancer or cancer state, or in the absence of a particular variable such as a therapeutic agent. A control level also includes the expression level of the gene(s) and/or protein(s) from one or more selected samples or subjects as described herein. For example, a control level includes an assessment of the expression level of the gene(s) and/or protein(s) in a sample from a subject that does not have cancer, is at a selected stage of cancer or cancer state, or have cancer but have not yet received treatment for the cancer. Another exemplary control level includes an assessment of the expression level of the gene(s) and/or protein(s) in samples taken from multiple subjects that do not have cancer, are at a selected stage of cancer, or have cancer but have not yet received treatment for the cancer.

Suitable controls for comparison of gene or protein expression in a patient or tumor include, without limitation, a sample from a healthy subject, a sample from a non-cancerous tissue (from the same patient or a different individual), or an average level of expression in a population (e.g., a population having cancer or a healthy population). Other suitable controls include, without limitation, comparison of samples after treatment to baseline samples; and genes that are not known to change with adenosine level and/or constitutive genes that are required for the maintenance of basic cellular function (so-called housekeeping genes are well-known in the art). In embodiments, the control is an expression threshold based on responsiveness to treatment with an adenosine pathway inhibitor.

In embodiments, the control is a sample from a non-cancerous tissue. In embodiments, the control is a sample from healthy tissue in proximity to the tumor (e.g., apparently healthy peripheral tissue in a tumor biopsy). In embodiments, the control is a blood sample from a healthy subject. In embodiments, the control is an average of expression in a population of subjects. In embodiments, the control is a median of expression in a population of subjects. In embodiments, the control is a baseline sample (sample taken before treatment, e.g. with an adenosine pathway inhibitor) from the subject.

In some embodiments, a threshold for elevated expression levels of the gene(s) and/or protein(s) is above the median expression level of a group of control sample. In some embodiments it is above the first quartile of expression of the gene(s) and/or protein(s) in a group of control samples. In some embodiments it is above the third quartile of expression of the gene(s) and/or protein(s) in a group of control sample. In some embodiments it is above the 5th percentile of expression of the gene(s) and/or protein(s) in a group of control samples. In some embodiments it is above the 10th percentile of expression of the gene(s) and/or protein(s) in a group of control samples. In some embodiments it is above the 20th percentile of expression of the gene(s) and/or protein(s) in a group of control samples. In some embodiments it is above the 30th percentile of expression of the gene(s) and/or protein(s) in a group of control samples. In some embodiments it is above the 40th percentile of expression of the gene(s) and/or protein(s) in a group of control samples. In some embodiments it is above the 45th percentile of expression of the gene(s) and/or protein(s) in a group of control samples. In some embodiments it is above the 50th percentile of expression of the gene(s) and/or protein(s) in a group of control samples. In some embodiments it is above the 60th percentile of expression of the gene(s) and/or protein(s) in a group of control samples. In some embodiments it is above the 70th percentile of expression of the gene(s) and/or protein(s) in a group of control samples. In some embodiments it is above the 80th percentile of expression of the gene(s) and/or protein(s) in a group of control samples. In some embodiments it is above the 90th percentile of expression of the gene(s) and/or protein(s) in a group of control samples.

In some embodiments, a threshold for reduced expression levels of the gene(s) and/or protein(s) is below the median expression level of a group of control sample. In some embodiments it is below the first quartile of expression of the gene(s) and/or protein(s) in a group of control samples. In some embodiments it is below the third quartile of expression of the gene(s) and/or protein(s) in a group of control sample. In some embodiments it is below the 5th percentile of expression of the gene(s) and/or protein(s) in a group of control samples. In some embodiments it is below the 10th percentile of expression of the gene(s) and/or protein(s) in a group of control samples. In some embodiments it is below the 20th percentile of expression of the gene(s) and/or protein(s) in a group of control samples. In some embodiments it is below the 30th percentile of expression of the gene(s) and/or protein(s) in a group of control samples. In some embodiments it is below the 40th percentile of expression of the gene(s) and/or protein(s) in a group of control samples. In some embodiments it is below the 45th percentile of expression of the gene(s) and/or protein(s) in a group of control samples. In some embodiments it is below the 50th percentile of expression of the gene(s) and/or protein(s) in a group of control samples. In some embodiments it is below the 60th percentile of expression of the gene(s) and/or protein(s) in a group of control samples. In some embodiments it is below the 70th percentile of expression of the gene(s) and/or protein(s) in a group of control samples. In some embodiments it is below the 80th percentile of expression of the gene(s) and/or protein(s) in a group of control samples. In some embodiments it is below the 90th percentile of expression of the gene(s) and/or protein(s) in a group of control samples.

Methods of Identifying Genes

In an aspect is provided a method of identifying one or more genes having an expression that is correlated with activation of the adenosine pathway. In embodiments, the method comprises comparing the expression of the one or more genes with the expression of one or more adenosine-activated genes, wherein adenosine-activated genes are genes known to be up-regulated in response to activation of the adenosine pathway. In embodiments, the method comprises comparing the expression of the one or more genes with the expression of one or more adenosine-repressed genes, wherein adenosine-repressed genes are genes known to be down-regulated in response to activation of the adenosine pathway.

In embodiments, the one or more adenosine-activated genes are selected from the genes in Tables 2-9. In embodiments, the one or more adenosine-repressed genes are selected from the genes in Table 1.

In embodiments, the method comprises correlating the expression of the one or more genes to expression of the one or more adenosine-activated genes. In an embodiment, the expressions are correlated by determining which genes in a group of genes are in the top 5% of genes most highly correlated with expression of the one or more adenosine-activated (or adenosine-repressed) genes. In embodiments, correlation is determined in one or more tumor types.

In embodiments, high expression of the one or more adenosine-activated genes is determined based on a baseline expression level. In embodiments, the baseline expression level is the average level of expression of the gene(s) in a particular cancer. In an embodiment, the baseline expression level is the average level of expression of the gene(s) in the cancer type to be treated.

In embodiments, the genes to be correlated are a database of gene expression levels. In embodiments, the genes to be correlated are from a publically-available database of gene expression levels. In embodiments, the genes to be correlated are from a database of gene expression levels in a cancer. In embodiments, the genes to be correlated are from The Cancer Genome Atlas (TCGA).

In embodiments, the expressions are correlated by determining which genes in a group of genes are in the top 5% of genes most highly correlated with expression of the one or more adenosine-activated (or adenosine-repressed) genes. In embodiments, the expressions are correlated by determining which genes in a group of genes are in the top 4% of genes most highly correlated with expression of the one or more adenosine-activated (or adenosine-repressed) genes. In embodiments, the expressions are correlated by determining which genes in a group of genes are in the top 3% of genes most highly correlated with expression of the one or more adenosine-activated (or adenosine-repressed) genes. In embodiments, the expressions are correlated by determining which genes in a group of genes are in the top 2.5% of genes most highly correlated with expression of the one or more adenosine-activated (or adenosine-repressed) genes. In embodiments, the expressions are correlated by determining which genes in a group of genes are in the top 2% of genes most highly correlated with expression of the one or more adenosine-activated (or adenosine-repressed) genes. In embodiments, the expressions are correlated by determining which genes in a group of genes are in the top 1% of genes most highly correlated with expression of the one or more adenosine-activated (or adenosine-repressed) genes. In embodiments, the expressions are correlated by determining which genes in a group of genes are in the top 1.5% of genes most highly correlated with expression of the one or more adenosine-activated (or adenosine-repressed) genes. In embodiments, the expressions are correlated by determining which genes in a group of genes are in the top 1% of genes most highly correlated with expression of the one or more adenosine-activated (or adenosine-repressed) genes.

In embodiments, the expressions are correlated by determining which genes in a group of demonstrate a Spearman's correlation value of 0.4 when correlated with expression of the one or more adenosine-activated (or adenosine-repressed) genes. In embodiments, the expressions are correlated by determining which genes in a group of demonstrate a Spearman's correlation value of 0.5 when correlated with expression of the one or more adenosine-activated (or adenosine-repressed) genes.

In embodiments, the expressions are correlated by determining which genes in a group of demonstrate a Spearman's correlation value of 0.6 when correlated with expression of the one or more adenosine-activated (or adenosine-repressed) genes. In embodiments, the expressions are correlated by determining which genes in a group of demonstrate a Spearman's correlation value of 0.7 when correlated with expression of the one or more adenosine-activated (or adenosine-repressed) genes. In embodiments, the expressions are correlated by determining which genes in a group of demonstrate a Spearman's correlation value of 0.8 when correlated with expression of the one or more adenosine-activated (or adenosine-repressed) genes. In embodiments, the expressions are correlated by determining which genes in a group of demonstrate a Spearman's correlation value of 0.9 when correlated with expression of the one or more adenosine-activated (or adenosine-repressed) genes.

In embodiments, the cancer or tumor type is adrenalcortical cancer, bladder/urothelial cancer, breast cancer, cervical cancer, cholangiocarcinoma, colorectal adenocarcinoma, diffuse large B-cell lymphoma, glioma, head and neck squamous cell carcinoma, renal cancer, renal clear cell cancer, papillary cell cancer, hepatocellular cancer, lung cancer, mesothelioma, ovarian cancer, pancreatic cancer, pheochromocytoma, paraganglioma, prostate cancer, rectal cancer, sarcoma, melanoma, stomach or esophageal cancer, testicular cancer, thyroid cancer, thymoma, uterine cancer, and/or uveal melanoma.

IV. Kits

In embodiments is provided a kit for determining a level of gene expression in a biological sample, the kit comprising: (i) a primer for one or more genes selected from CCL2, CCL3, CCL7, CCL24, CCNE1, CD14, CD300E, CD86, CD93, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, IL1A, IL-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, and/or WDR83OS; and (ii) a reagent for processing of the biological sample. In embodiments, the reagent for processing of the biological sample is a reagent for preparing cDNA from the biological sample, those listed in Table 1 and/or Table 2

In embodiments is provided a kit for determining a level of gene expression in a biological sample, the kit comprising: (i) a primer for one or more genes selected from those listed in Table 1 and/or Table 2; and (ii) a reagent for processing of the biological sample. In embodiments, the reagent for processing of the biological sample is a reagent for preparing cDNA from the biological sample.

In embodiments, the kit further comprises one or more reagents for RNA sequencing. In embodiments, the kit further comprises a microarray configured for sequencing of the one or more genes. In embodiments, the kit further comprises reagents for quantitative PCR of the one or more genes. In embodiments, the kit further comprises reagents for RNA-seq. In embodiments, the kit further comprises instructions for determining the level of gene expression in the biological sample. In embodiments, the biological sample is selected from a blood sample, a tumor biopsy, or immune cells. In embodiments, the kit further comprises a control.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1: mRNA Expression in PBMCs is Modulated by NECA

RNA purified from normal, healthy human peripheral blood mononuclear cells (PBMCs) treated with 5'-N-ethylcarboxamidoadenosine (NECA) and activated with anti-CD3/CD28 antibody were analyzed by NanoString hybridization-based quantification (NanoString Technologies, Inc.). FIG. 1 shows the NanoString quantification data; labeled genes are consistently modulated by NECA treatment. Each dot represents the expression level of a specific gene. Dot shade represents the concentration of NECA used and/or different PBMC donors. Genes above the diagonal axis are upregulated relative to the DMSO control. Genes below the diagonal axis are downregulated relative to the DMSO control. Table 3 provides a list of genes up- or down-regulated by 0.1 µM, 1 µM, and/or 10 µM NECA treatment (compared to vehicle-treated control), as determined by NanoString NPR1 sequencing.

TABLE 3

| | NanoString NECA Response | | | | | |
|---|---|---|---|---|---|---|
| | logFC | AveExpr | t | P. Value | adj. P. Val | B |
| IL23A | 0.4627649 | 7.334838 | 14.798268 | 1.786369e−07 | 0.0001439813 | 7.9505117 |
| SLC11A1 | 0.7021764 | 6.491349 | 10.203259 | 3.872126e−06 | 0.0012732331 | 4.9849006 |
| CXCL2 | 1.0933451 | 10.195356 | 9.788027 | 5.416504e−06 | 0.0012732331 | 4.6475145 |
| PPBP | 0.6830220 | 6.958370 | 9.602293 | 6.318774e−06 | 0.0012732331 | 4.4919476 |
| CXCL6 | 0.6534592 | 6.258443 | 9.040855 | 1.022672e−05 | 0.0014021847 | 4.0032089 |
| CXCL3 | 1.1014168 | 11.285506 | 9.017618 | 1.043810e−05 | 0.0014021847 | 3.9823596 |
| IL6 | 0.7013922 | 9.696798 | 8.785498 | 1.283590e−05 | 0.0014779619 | 3.7712731 |
| IL1A | 0.6367293 | 8.647285 | 8.465251 | 1.720125e−05 | 0.0017330256 | 3.4713983 |
| IL8 | 0.6411258 | 13.867136 | 8.184402 | 2.240173e−05 | 0.0019841851 | 3.1998235 |
| CXCL5 | 1.3377878 | 10.968259 | 8.085931 | 2.461768e−05 | 0.0019841851 | 3.1026377 |
| THBS1 | 0.8702939 | 8.654629 | 7.844189 | 3.115335e−05 | 0.0022826908 | 2.8595930 |
| IL1B | 0.6345216 | 11.465422 | 7.716214 | 3.537004e−05 | 0.0023756877 | 2.7283049 |
| PTGS2 | 0.6892445 | 6.477524 | 7.527272 | 4.278893e−05 | 0.0026529134 | 2.5310619 |
| IL24 | 0.5768303 | 5.631345 | 7.436029 | 4.697147e−05 | 0.0027042145 | 2.4343268 |
| CXCL1 | 0.6908547 | 11.778099 | 7.017143 | 7.289634e−05 | 0.0039169631 | 1.9774180 |
| CD86 | 0.3147833 | 6.509483 | 6.679459 | 1.053756e−04 | 0.0053082971 | 1.5931758 |
| CLEC5A | 0.3832928 | 7.397527 | 6.504225 | 1.282517e−04 | 0.0058185249 | 1.3879565 |
| PLAUR | 0.5031196 | 6.596991 | 6.492660 | 1.299422e−04 | 0.0058185249 | 1.3742698 |
| CD14 | 0.4485481 | 6.012462 | 6.384296 | 1.470223e−04 | 0.0062368414 | 1.2451525 |
| TBX21 | −0.1237810 | 9.998925 | −6.160737 | 1.905559e−04 | 0.0076794030 | 0.9737429 |

Data were confirmed by RNA sequencing (RNA-Seq). Tables 4-6 provide a list of genes up- or down-regulated by 0.1 μM, 1 μM, and 10 μM NECA treatment (compared to vehicle-treated control), as determined by RNA-Seq.

TABLE 4

| Control (DMSO) vs 0.1 μm NECA | | | | | | |
|---|---|---|---|---|---|---|
| | logFC | AveExpr | t | P. Value | adj. P. Val | B |
| OST4 | -0.2352447 | 8.6345128 | -11.970085 | 9.130909e-06 | 0.1459928 | 2.52992769 |
| LAYN | 0.4228418 | 3.3566114 | 11.161307 | 1.429928e-05 | 0.1459928 | 2.32994552 |
| IL23A | 0.7971259 | 5.1913339 | 10.653898 | 1.923995e-05 | 0.1459928 | 2.18870314 |
| CXCL2 | 1.4518477 | 6.0095672 | 9.200030 | 4.859080e-05 | 0.2447682 | 1.70118485 |
| EHF | -0.2752739 | 0.3920579 | -9.003396 | 5.561691e-05 | 0.2447682 | 1.62418640 |
| SPON1 | 0.3610858 | 1.2812223 | 8.791529 | 6.451455e-05 | 0.2447682 | 1.53784040 |
| CXCL5 | 2.3880055 | 7.2219322 | 8.416007 | 8.457489e-05 | 0.2569563 | 1.37564914 |
| CXCL3 | 1.6938152 | 6.5581731 | 8.327199 | 9.030269e-05 | 0.2569563 | 1.33549284 |
| HAS1 | 2.0592455 | 3.1302598 | 7.587293 | 1.596760e-04 | 0.3710055 | 0.97161761 |
| EPB41L3 | 1.1827820 | 4.0241563 | 7.561761 | 1.629791e-04 | 0.3710055 | 0.95806543 |
| WDR83OS | -0.2872011 | 6.1538619 | -7.357523 | 1.923783e-04 | 0.3932963 | 0.84708953 |
| EML6 | 0.2117477 | 0.8770298 | 7.166861 | 2.253531e-04 | 0.3932963 | 0.73923990 |
| MRPL11 | -0.1900318 | 5.9598013 | -7.111915 | 2.360127e-04 | 0.3932963 | 0.70737138 |
| FUT7 | -0.2134840 | 3.2412131 | -7.073810 | 2.437404e-04 | 0.3932963 | 0.68505992 |
| CSF3 | 1.6028984 | 3.5125600 | 7.001723 | 2.591567e-04 | 0.3932963 | 0.64237158 |
| SLC7A7 | 0.5935059 | 4.5833442 | 6.917625 | 2.785495e-04 | 0.3963063 | 0.59178022 |
| ZBTB18 | 0.2430712 | 6.0833469 | 6.746980 | 3.231814e-04 | 0.4327590 | 0.48636644 |
| NPR1 | 0.7891637 | 1.4976083 | 6.524711 | 3.939395e-04 | 0.4982022 | 0.343423 |
| CCL24 | -1.0683889 | 3.9397950 | -6.432892 | 4.281577e-04 | 0.5129780 | 0.28244202 |
| SYTL3 | 0.2894392 | 7.1630457 | 6.182207 | 5.399904e-04 | 0.6146170 | 0.10996986 |
| ST6GALNAC2 | 0.5341875 | 2.0517115 | 5.976222 | 6.568806e-04 | 0.6695229 | -0.03854598 |
| PADI2 | 0.4801685 | 1.7177200 | 5.970771 | 6.603396e-04 | 0.6695229 | -0.04256211 |
| PTGS2 | 1.1842585 | 5.1027784 | 5.945778 | 6.764640e-04 | 0.6695229 | -0.06103360 |
| KLC4 | 0.2159937 | 3.5957446 | 5.793114 | 7.851248e-04 | 0.7283496 | -0.17593573 |
| INHBA | 0.5196461 | 5.7314423 | 5.734928 | 8.316022e-04 | 0.7283496 | -0.22068184 |
| MS4A7 | 0.9318833 | 2.7682162 | 5.711971 | 8.507842e-04 | 0.7283496 | -0.23848306 |
| CD93 | 0.9975052 | 2.9396984 | 5.696625 | 8.638833e-04 | 0.7283496 | -0.25042868 |

51

TABLE 5

| Control (DMSO) vs 1 μm NECA | | | | | | |
|---|---|---|---|---|---|---|
| | logFC | AveExpr | t | P. Value | adj. P. Val | B |
| IL23A | 1.36344204 | 5.19133391 | 18.222934 | 5.910866e-07 | 0.01345550 | 5.003777 |
| CXCL2 | 2.36081829 | 6.00956717 | 14.959970 | 2.153135e-06 | 0.01675823 | 4.404362 |
| LAYN | 0.52769487 | 3.35661136 | 13.929003 | 3.427337e-06 | 0.01675823 | 4.154923 |
| SPON1 | 0.56674776 | 1.28122227 | 13.798880 | 3.642781e-06 | 0.01675823 | 4.120859 |
| FUT7 | -0.41577673 | 3.24121313 | -13.776796 | 3.680863e-06 | 0.01675823 | 4.115016 |
| CXCL3 | 2.57339804 | 6.55817311 | 12.651438 | 6.391316e-06 | 0.02215030 | 3.791954 |
| CSF3 | 2.80241003 | 3.51256001 | 12.241386 | 7.904467e-06 | 0.02215030 | 3.660729 |
| CXCL5 | 3.45116519 | 7.22193218 | 12.162882 | 8.238833e-06 | 0.02215030 | 3.634704 |
| HAS1 | 3.23765037 | 3.13025984 | 11.929128 | 9.334356e-06 | 0.02215030 | 3.555423 |
| EPB41L3 | 1.85388331 | 4.02415632 | 11.852245 | 9.730410e-06 | 0.02215030 | 3.528748 |
| PTGS2 | 2.22964251 | 5.10277836 | 11.194311 | 1.403189e-05 | 0.02826544 | 3.287631 |
| SLC7A7 | 0.95144755 | 4.58334422 | 11.089656 | 1.490008e-05 | 0.02826544 | 3.247049 |
| INHBA | 0.96880024 | 5.73144231 | 10.636710 | 1.943867e-05 | 0.03403861 | 3.063837 |
| GPR157 | 0.92828868 | 3.52957346 | 9.977468 | 2.916818e-05 | 0.04742746 | 2.773507 |
| MS4A7 | 1.53451659 | 2.76821622 | 9.405827 | 4.229917e-05 | 0.06058963 | 2.496589 |
| ZBTB18 | 0.33849489 | 6.08334692 | 9.395675 | 4.258628e-05 | 0.06058963 | 2.491454 |
| ST6GALNAC2 | 0.83059948 | 2.05171148 | 9.292332 | 4.564542e-05 | 0.06112190 | 2.438606 |
| PADI2 | 0.71731455 | 1.71772002 | 8.919620 | 5.895677e-05 | 0.07220253 | 2.240666 |
| OST4 | -0.17467913 | 8.63451280 | -8.888293 | 6.026393e-05 | 0.07220253 | 2.223489 |
| CCDC60 | 0.07658115 | 0.02839705 | 8.678638 | 6.991132e-05 | 0.07480295 | 2.106290 |
| PID1 | 1.72878073 | 2.06172975 | 8.617287 | 7.305870e-05 | 0.07480295 | 2.071243 |
| IL24 | 2.87636460 | 2.26316631 | 8.599890 | 7.398028e-05 | 0.07480295 | 2.061243 |
| EREG | 1.89042090 | 2.63480414 | 8.570229 | 7.557845e-05 | 0.07480295 | 2.044167 |
| EMR3 | 1.36402609 | 2.02038959 | 8.497153 | 7.970017e-05 | 0.07559561 | 2.001610 |
| CD93 | 1.45354972 | 2.93969845 | 8.301038 | 9.207320e-05 | 0.08073785 | 1.884998 |
| TGIF1 | 0.47686174 | 5.75488492 | 8.260751 | 9.487740e-05 | 0.08073785 | 1.860582 |
| EHF | -0.25218803 | 0.39205795 | -8.248325 | 9.576182e-05 | 0.08073785 | 1.853020 |

TABLE 6

Control (DMSO) vs 10 µm NECA

|  | logFC | AveExpr | t | P. Value | adj. P. Val | B |
|---|---|---|---|---|---|---|
| CXCL2 | 3.0114695 | 6.0095672 | 19.082999 | 4.363216e−07 | 0.00782629 | 5.966260 |
| IL23A | 1.3324364 | 5.1913339 | 17.808531 | 6.876024e−07 | 0.00782629 | 5.720905 |
| CSF3 | 3.5076869 | 3.5125600 | 15.322151 | 1.841900e−06 | 0.01072075 | 5.129214 |
| CXCL3 | 3.1059218 | 6.5581731 | 15.269452 | 1.883809e−06 | 0.01072075 | 5.114749 |
| HAS1 | 3.8065888 | 3.1302598 | 14.025382 | 3.277149e−06 | 0.01362460 | 4.745597 |
| SPON1 | 0.5679964 | 1.2812223 | 13.829280 | 3.591092e−06 | 0.01362460 | 4.682195 |
| INHBA | 1.1918043 | 5.7314423 | 13.153012 | 4.970709e−06 | 0.01616475 | 4.451478 |
| EPB41L3 | 2.0000860 | 4.0241563 | 12.786948 | 5.966277e−06 | 0.01697704 | 4.318281 |
| GPR157 | 1.1388489 | 3.5295735 | 12.240619 | 7.907658e−06 | 0.01850472 | 4.107731 |
| CXCL5 | 3.3540123 | 7.2219322 | 11.820488 | 9.899583e−06 | 0.01850472 | 3.935558 |
| IL5 | −0.6885411 | 3.1041696 | −11.796658 | 1.002874e−05 | 0.01850472 | 3.925511 |
| PTGS2 | 2.3486150 | 5.1027784 | 11.791634 | 1.005621e−05 | 0.01850472 | 3.923388 |
| PADI2 | 0.9386170 | 1.7177200 | 11.671458 | 1.073977e−05 | 0.01850472 | 3.872214 |
| NID1 | 1.0868853 | 1.5369851 | 11.566496 | 1.138051e−05 | 0.01850472 | 3.826862 |
| CCNE1 | −0.4517546 | 4.5711709 | −10.996299 | 1.572663e−05 | 0.02328128 | 3.569350 |
| LAP3 | −0.4286219 | 7.8532183 | −10.925695 | 1.638659e−05 | 0.02328128 | 3.536101 |
| CD93 | 1.8954553 | 2.9396984 | 10.824704 | 1.738630e−05 | 0.02328128 | 3.488001 |
| SLC7A7 | 0.9134148 | 4.5833442 | 10.646362 | 1.932679e−05 | 0.02398947 | 3.401468 |
| PID1 | 2.1240047 | 2.0617298 | 10.587321 | 2.002284e−05 | 0.02398947 | 3.372366 |
| ECEL1 | 0.6918315 | 0.5334337 | 10.496000 | 2.115658e−05 | 0.02408042 | 3.326898 |
| LOC100505585 | 0.6638804 | 0.9321985 | 10.027489 | 2.826034e−05 | 0.02754795 | 3.084657 |
| DFNA5 | 0.6558752 | 1.4449118 | 9.965051 | 2.939868e−05 | 0.02754795 | 3.051201 |
| RHCG | 0.5767413 | 0.3322303 | 9.899768 | 3.064515e−05 | 0.02754795 | 3.015916 |
| CD300E | 1.7103407 | 1.6697661 | 9.838551 | 3.186905e−05 | 0.02754795 | 2.982542 |
| GBP6 | −0.8039494 | 3.6192663 | −9.833788 | 3.196658e−05 | 0.02754795 | 2.979934 |
| GALM | −0.3188743 | 4.1620985 | −9.830849 | 3.202694e−05 | 0.02754795 | 2.978323 |
| ST6GALNAC2 | 0.8759531 | 2.0517115 | 9.799725 | 3.267416e−05 | 0.02754795 | 2.961230 |

In vitro A2AR stimulation resulted in dose-dependent increases in CXCR2 ligands (CXCL1,2,3,5,8) and key mediators of neutrophil/MDSC biology (CSF3, IL-23). Increases in monocyte/macrophage inflammatory mediators such as IL-1b and CCL2,3,7,8, 20 were also observed, as were increases in SERPINB2, S100A8, PTGS2, THBS1. Expression of CXCL10 and GZMB were decreased, consistent with a suppressed IFNg response. CPI-444 treatment inhibited these changes at the transcript and protein level. A2AR agonists induce a specific gene signature (increase in a certain subset of genes and/or decrease in a second subset of genes) dominated by immunosuppressive mediators of MDSC and monocyte/macrophage biology. Inhibition of these genes by CPI-444 are observed. These gene signatures may be used as biomarkers for patient selection.

Example 2: CPI-444 Inhibits NECA-Induced Cytokine Expression

NECA activation of CXCL5 protein expression was evaluated. PBMCs were harvested from two different human donors. As shown in FIG. 2A, cells were treated with NECA, followed by CPI-444, then treated with anti-CD3/CD28 to activate the PBMCs. CPI-444 (Corvus Pharmaceuticals) is an antagonist of the adenosine A2A receptor. CXCL5 protein in the culture supernatants was evaluated by ELISA two days after activation. Data is provided in FIGS. 2B and 2C. CXCL5 expression is activated by NECA. This activation in CXCL5 can be blocked by the addition of CPI-444, a A2AR receptor antagonist that neutralizes the immunosuppressive effects of NECA. This establishes that the induction of CXCL5 is specific to signaling through adenosine receptors.

Example 3: CCL20 Expression Correlates With Expression of a Subset of Adenosine-Regulated Genes in Multiple Tumor Types Gene expression of CCL20 compared to expression of a subset of genes that were shown to be regulated by adenosine was determined in multiple solid tumor types, using the Cancer Genome Atlas (National Cancer Institute, National Human Genome Research Institute; found on at cancergenome.nih.gov) Genomic Data Commons Data Portal. Level of expression for the adenosine pathway was calculated in each tumor type as the mean of Log2 of the expression of genes shown to be induced by adenosine (CXCL1, CXCL2, CXCL3, CXCL5, SERPINB2, IL8, and IL1B). Gene expression of CCL20 and expression of this subset of genes are highly correlated in solid tumors (FIGS. 3A and 3B), indicating that CCL20 (and co-regulated genes) may be used as a surrogate for expression of this subset of genes. For all tumor types, $p<0.0001$. For all tumor types, this group of genes is in top 5% of all gene correlations with CCL20. For 7 of 12 tumor types, this group of genes is in top 1% of all gene correlations with CCL20.

Example 4: Gene Expression Correlates With Expression of a Subset of Adenosine-Regulated Genes in Baseline RCC Samples in Human Clinical Trial Methods: Tumor biopsies obtained at trial screening from patients with RCC (n=30) were analyzed for gene expression profiles with the Nanostring PanCancer Immune Panel that included 770 markers of immune activity and inflammation. The gene expression correlation (Spearman) matrix was hierarchically clustered (Ward's method) to identify modules of genes that were co-expressed across tumors. Gene expression was normalized to housekeeper genes included in the PanCancer Immune Panel. Gene cluster expression intensity was compared between patients with evaluable best change in tumor size ≤0 (n=8) vs >0 (n=15). The composite gene expression score was calculated as the average of the Log2 of expression values (normalized Nanostring counts) for seven genes (CXCL1, CXCL2, CXCL3, CXCL5, IL1B, IL8, SERPINB2) shown to be induced in vitro in normal peripheral blood mononuclear cells by adenosine. Protein expression was determined from blood (plasma) samples from baseline (untreated) renal cell carcinoma (RCC) patients using MesoScale assay.

Results: Gene expression compared to the composite gene expression score was determined in tumor samples from baseline (untreated) renal cell carcinoma (RCC) patients using the Nanostring Pan Cancer Immune Panel.

Figure 4A:
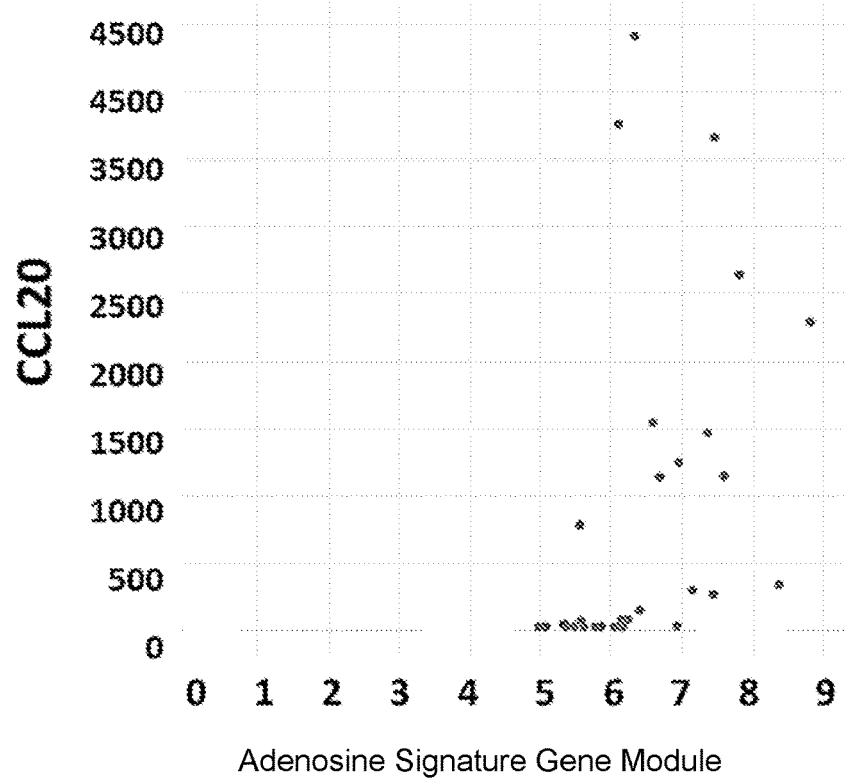
FIG. 4A shows the correlation of mean log 2 expression of genes in the adenosine composite gene expression module (X axis) with CCL20 gene expression (Y axis) in baseline RCC samples. There is a positive correlation between expression of these genes and CCL20.
Figure 4B:
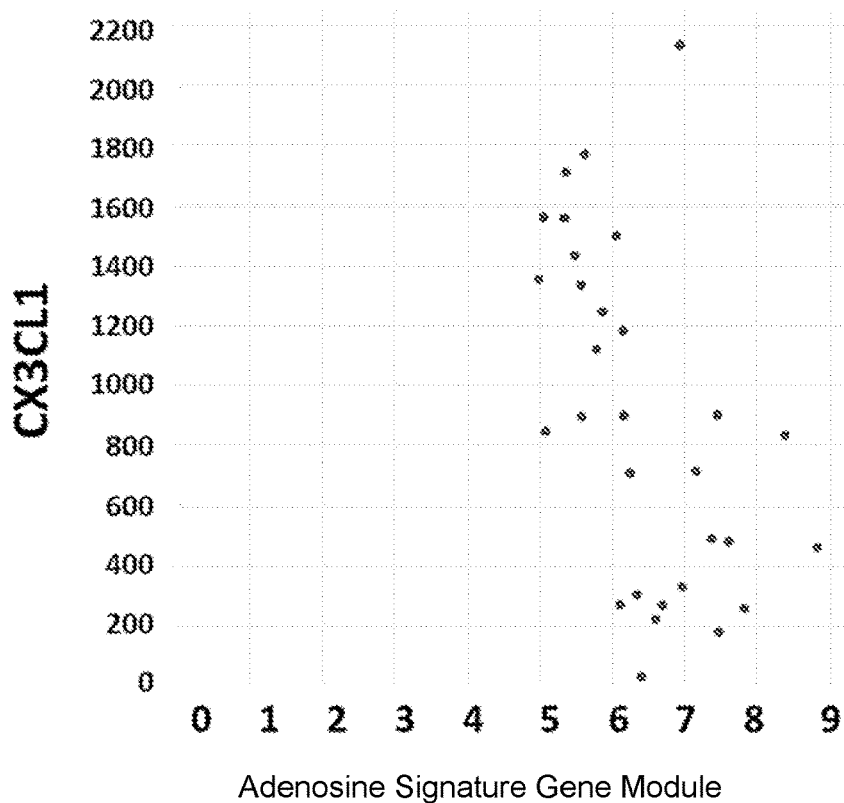
FIG. 4B shows the correlation of mean log 2 expression of genes in the adenosine composite gene expression module (X axis) with CX3CL1 gene expression (Y axis) in baseline RCC samples. There is a negative correlation between expression of these genes and CX3CL1.
Figure 5A:
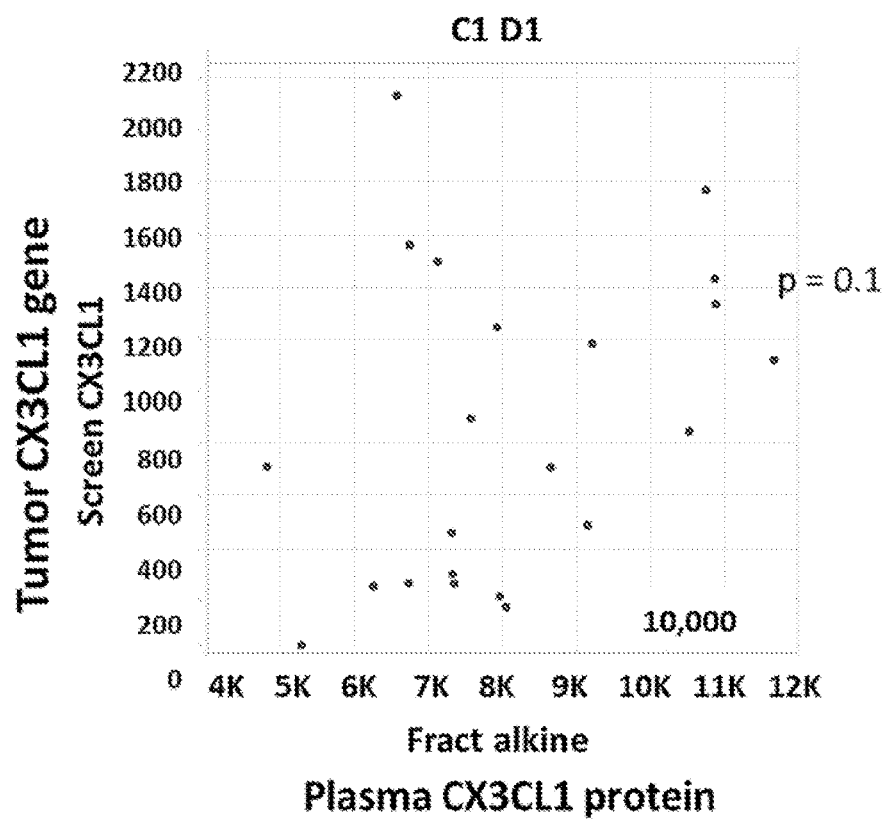
FIG. 5A shows the correlation between tumor CX3CL1 gene expression and circulating (plasma) CX3CL1 protein levels in baseline plasma samples from patients with RCC.
Figure 5B:
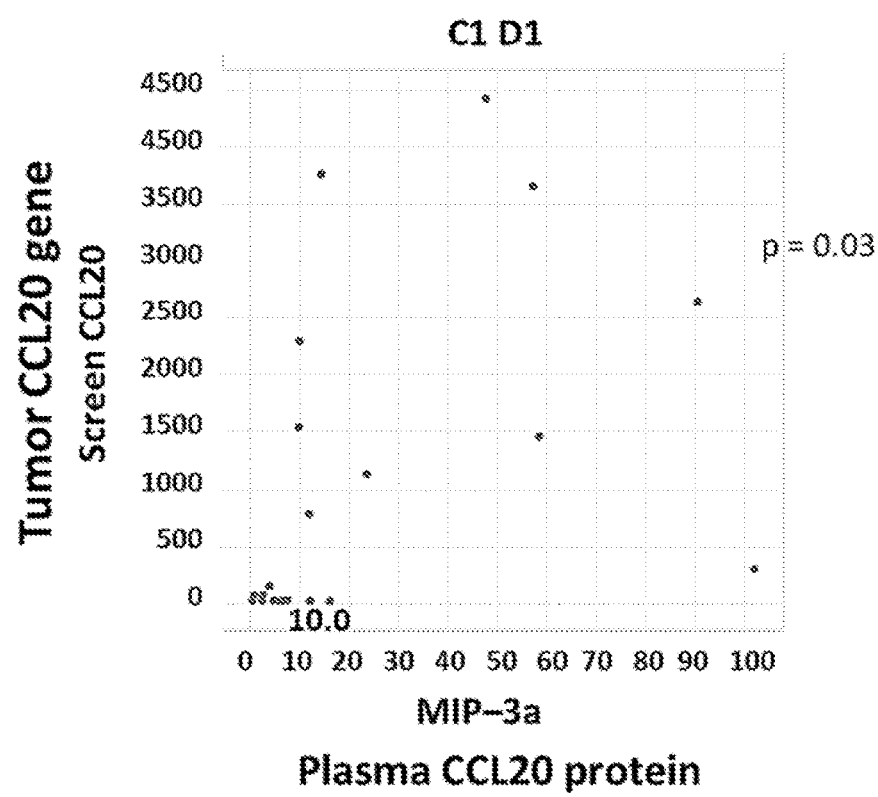
FIG. 5B shows the correlation between tumor CCL20 gene expression and circulating (plasma) CCL20 protein levels in baseline plasma samples from patients with RCC.
Figure 7:
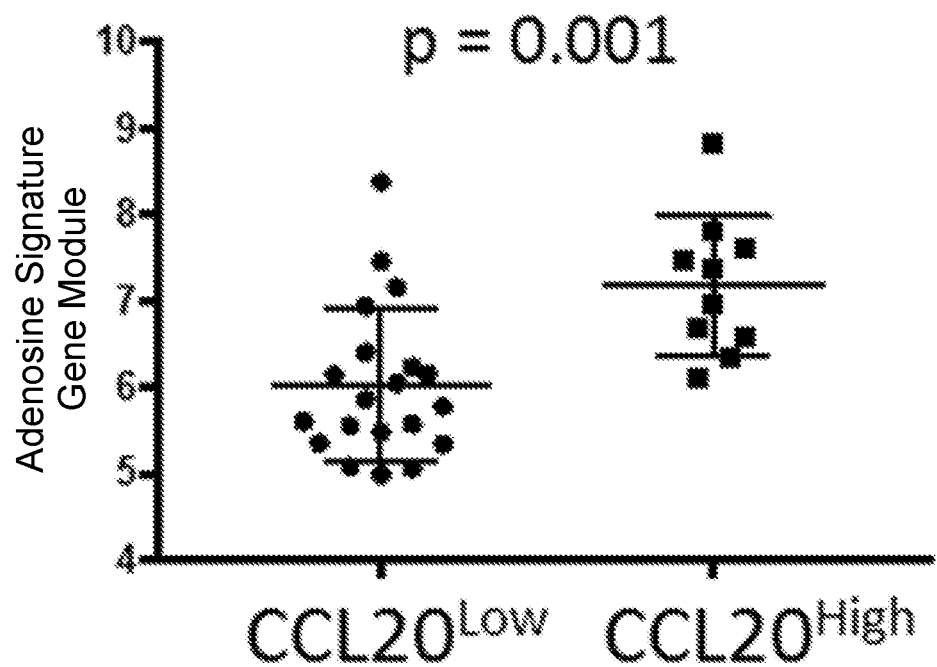
FIG. 7 shows the relationship between low or high CCL20 gene expression and the correlation of mean log 2 expression of genes in the adenosine composite gene expression module in baseline RCC samples. Tumors that are $CCL20^{High}$, $CX3CL1^{Low}$ have significantly higher expression of these genes than $CCL20^{Low}$, $CX3CL1^{High}$ tumors.

Gene expression of CCL20 and the composite gene expression score are highly correlated in solid tumors evaluated in the RCC samples (FIGS. 4A and 7A). In contrast, gene expression of CX3CL1 and the composite gene expression score are negatively correlated in the RCC samples (FIG. 4B). Gene expression in RCC samples and plasma protein levels for CX3CL1 (FIG. 5A) and CCL20 (FIG. 5B) are correlated, indicating that plasma levels of CX3CL1 and/or CCL20 can be evaluated as a proxy for composite gene expression score (e.g., the levels of multiple genes as described herein) in the tumor.

Figure 6A:
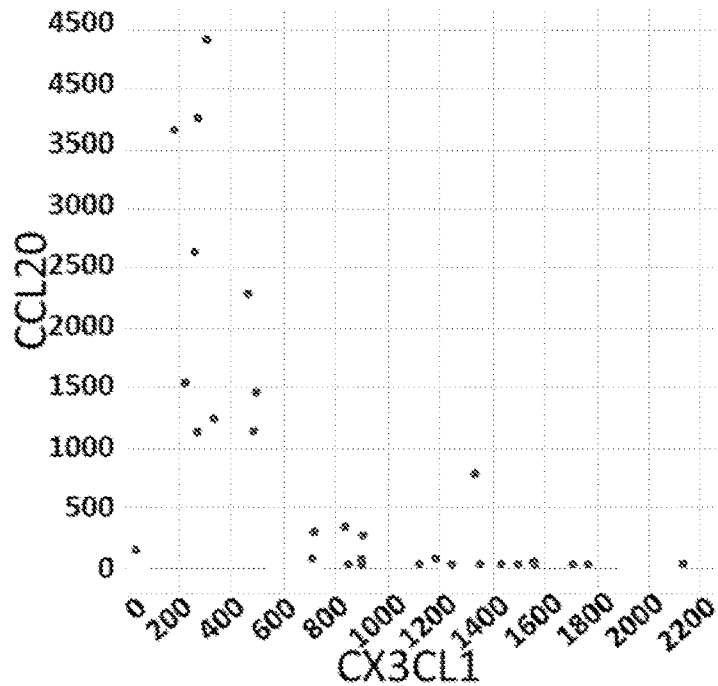
FIG. 6A shows CX3CL1 gene expression (X axis) correlation with CCL20 gene expression (Y axis) in baseline RCC samples. There is a negative correlation between CCL20 and CX3CL1 gene expression in RCC tumors; tumors express either CCL20 or CX3CL1.
Figure 6B:
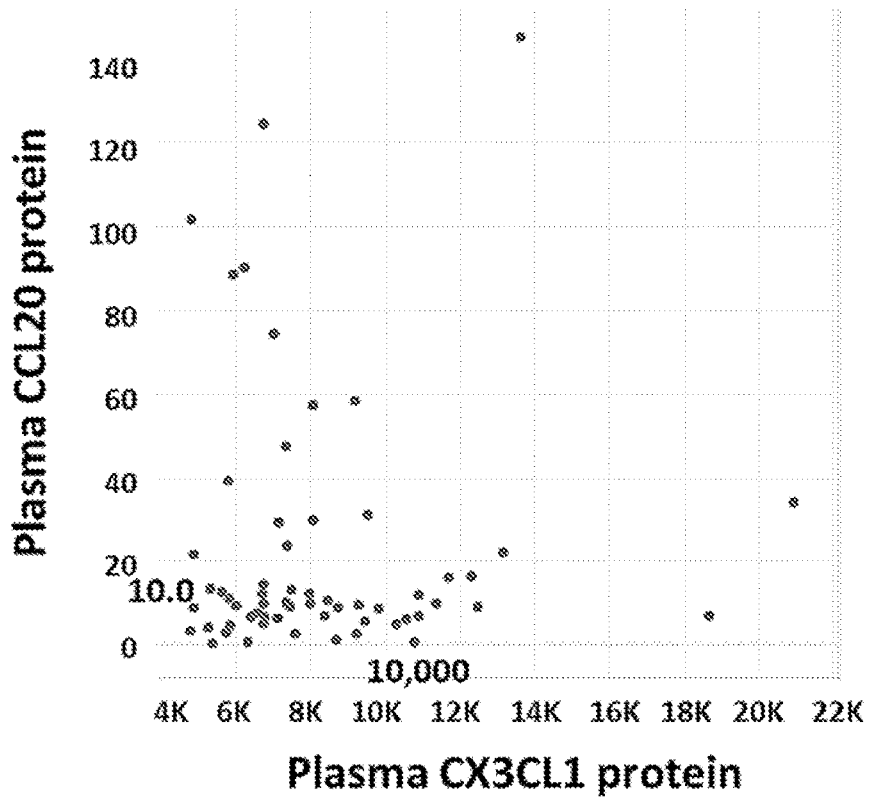
FIG. 6B shows CX3CL1 protein levels (X axis) correlation with CCL20 protein levels (Y axis) in baseline plasma samples from patients with RCC. There is a negative correlation between CCL20 and CX3CL1 plasma levels.

Gene expression of CCL20 and CX3CL1 are negatively correlated in the RCC samples (FIG. 6A), as are plasma protein levels (FIG. 6B).

To evaluate the correlation of composite gene expression score with various gene modules, expression levels for genes were determined using the Nanostring Pan Cancer Immune Panel. To find modules of co-regulated genes, first the Spearman's correlation values were calculated between all pairs of genes assayed across all renal patient tumor samples. Next, all the genes were clustered by Ward's method so that genes with high correlation values, meaning they showed correlated expression, were clustered together. Finally, all genes with a dendrogram height less than or equal to 12 were classified as being in the same cluster, which comprises a module of co-regulated genes showing similar expression patterns across the patients.

The adenosine composite gene expression score is part of a gene module of co-regulated genes. This "Adenosine Pathway" gene module is negatively correlated with other gene modules. One module it is negatively correlated with is the CX3CL1 Gene Module, which consists of APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, and TOLLIP. Functionally, this module contains elements of complement regulation and MAPK pathway signaling. A second gene module that is negatively correlated with the adenosine composite gene expression module is the Growth Factor Module, which consists of AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, and VEGFA. Functionally, this module is characterized by the Reactome pathway database as being enriched for signaling by FGFR, EGFR, NGF, and ERBB2.

Figure 8A:
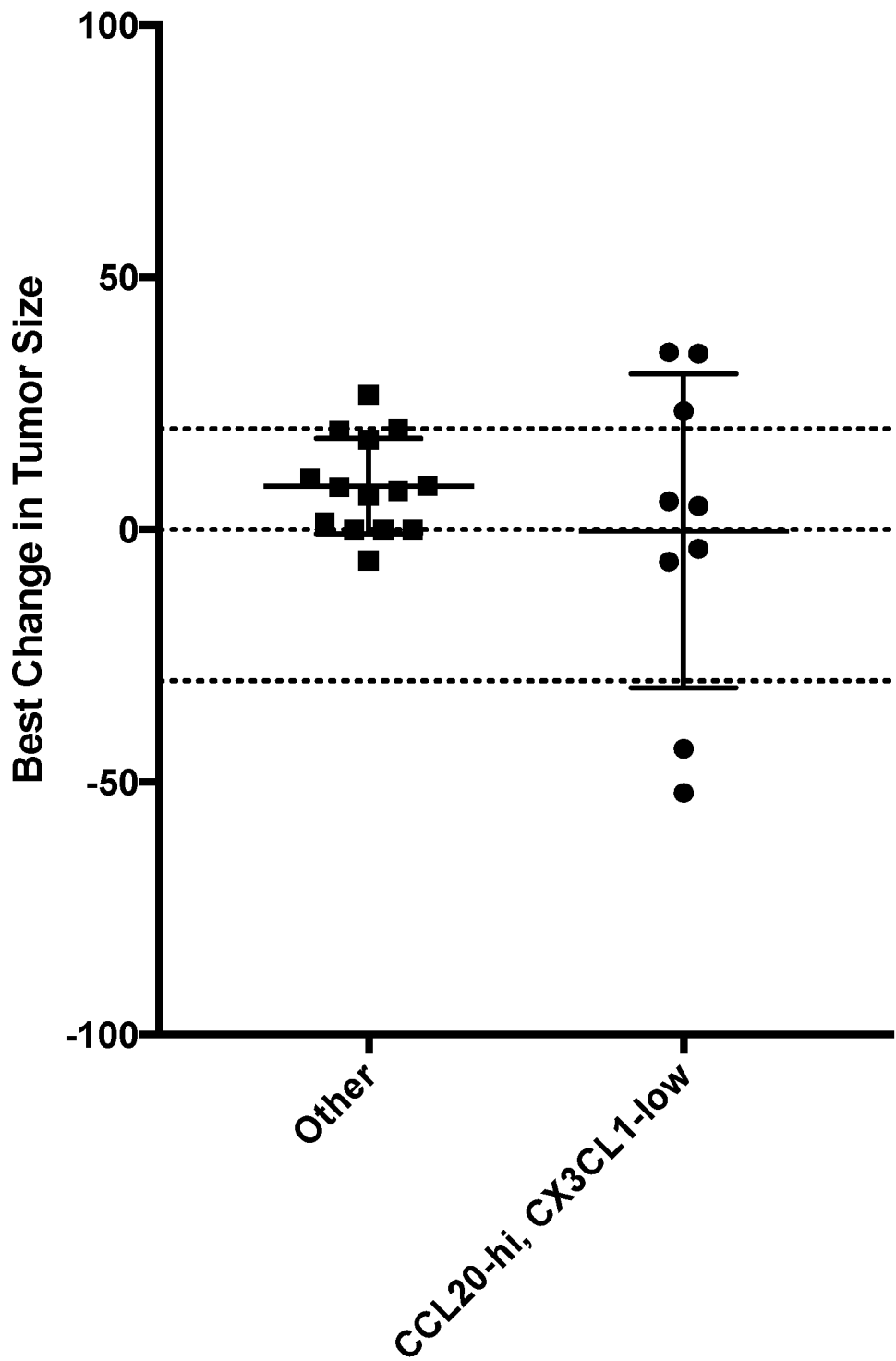
FIG. 8A represents the relationship between $CCL20^{High}$, $CX3CL1^{Low}$ plasma levels and in vivo tumor response to CPI-444 treatment in patients with RCC. Two of two subjects with greater than 30% reduction in tumor size exhibited $CCL20^{High}$, $CX3CL1^{Low}$ plasma levels.
Figure 8B:
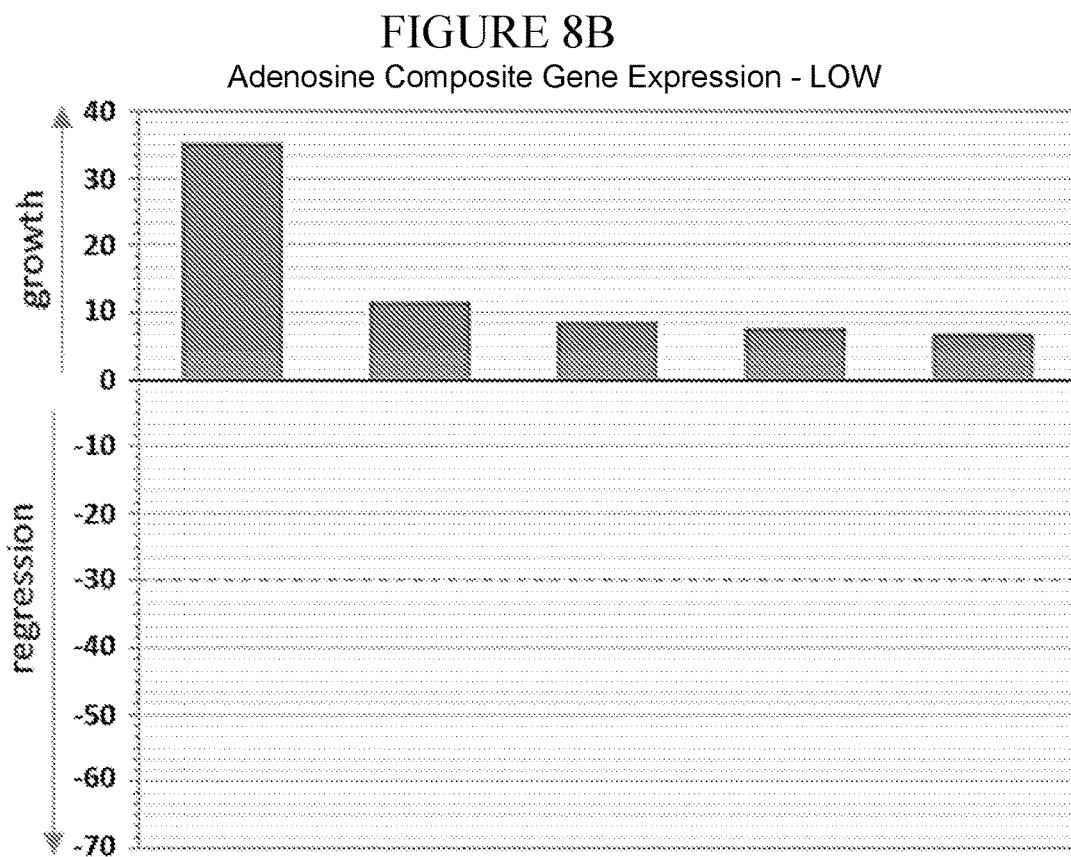
FIG. 8B shows the best overall percent change in tumor size after CPI-444 treatment for tumors having low expression of genes in the adenosine composite gene expression module in patients with RCC.
Figure 8C:
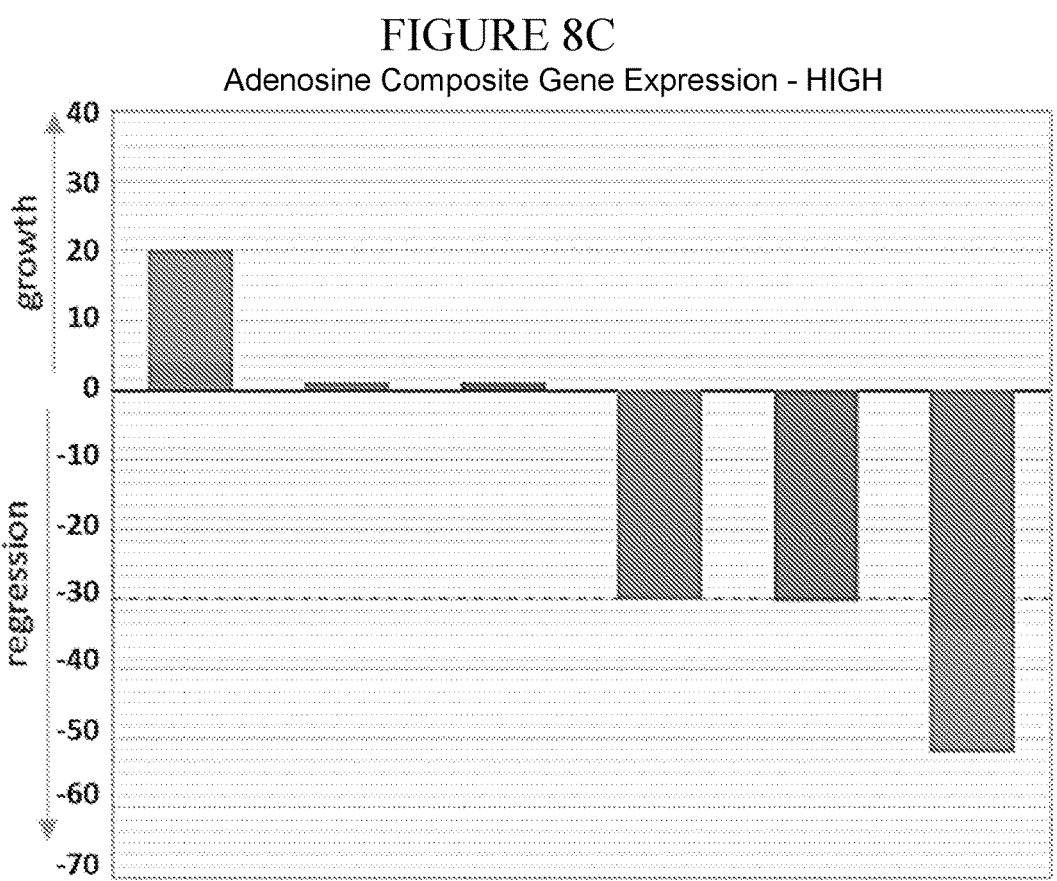
FIG. 8C shows the best overall percent change in tumor size after CPI-444 treatment for tumors having high expression of genes in the adenosine composite gene expression module in patients with RCC.

Example 5: Tumor Regression With CPI-444 Treatment Observed in Renal Tumors With High Baseline Expression of Adenosine-Regulated Genes Renal cancer patients were treated with CPI-444, and change in tumor size was measured. Patients with high CCL20 and low CX3CL1 plasma protein levels were more likely to respond to treatment with CPI-444 (FIG. 8A). Four patients whose tumors exhibited high composite gene expression score showed a reduction in tumor size after treatment, whereas tumor regression was not observed in patients with tumors with low composite gene expression score (FIGS. 8B and 8C).

Figure 9A:
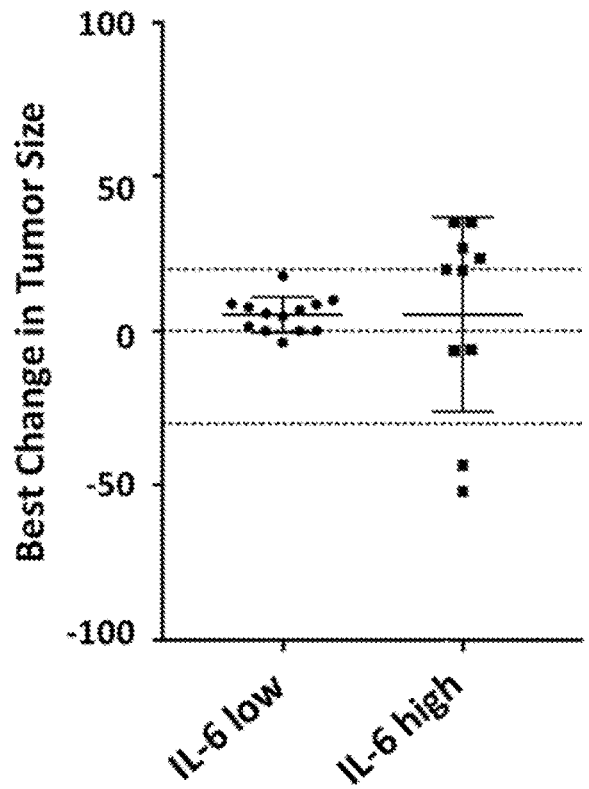
FIG. 9A shows the relationship between IL6 protein levels and best overall change in tumor size after CPI-444 treatment in patients with RCC. Two of two subjects with greater than 30% reduction in tumor size exhibited $IL6^{High}$ plasma levels.
Figure 9B:
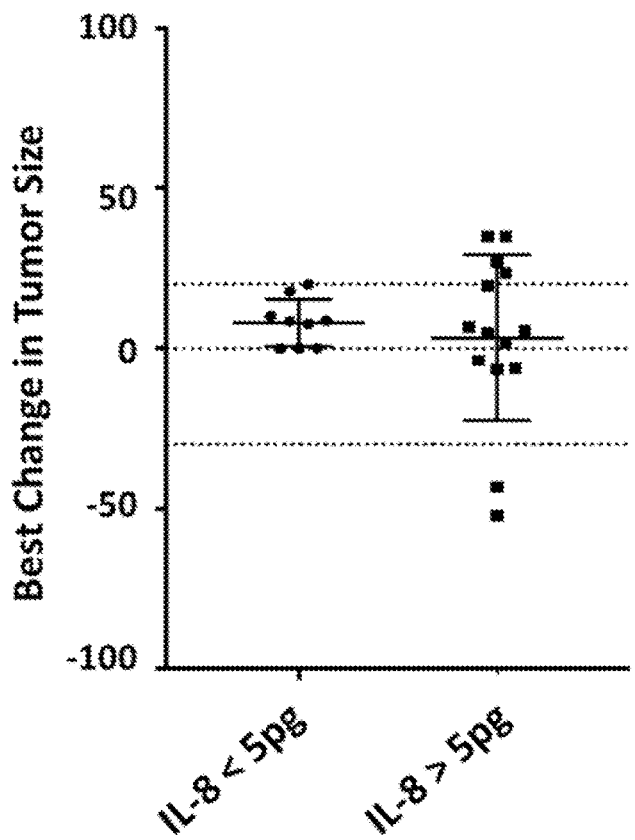
FIG. 9B shows the relationship between IL8 protein levels and best overall change in tumor size after CPI-444 treatment in patients with RCC. Two of two subjects with greater than 30% reduction in tumor size exhibited plasma IL8 levels >5 pg/mL.
Figure 10A:
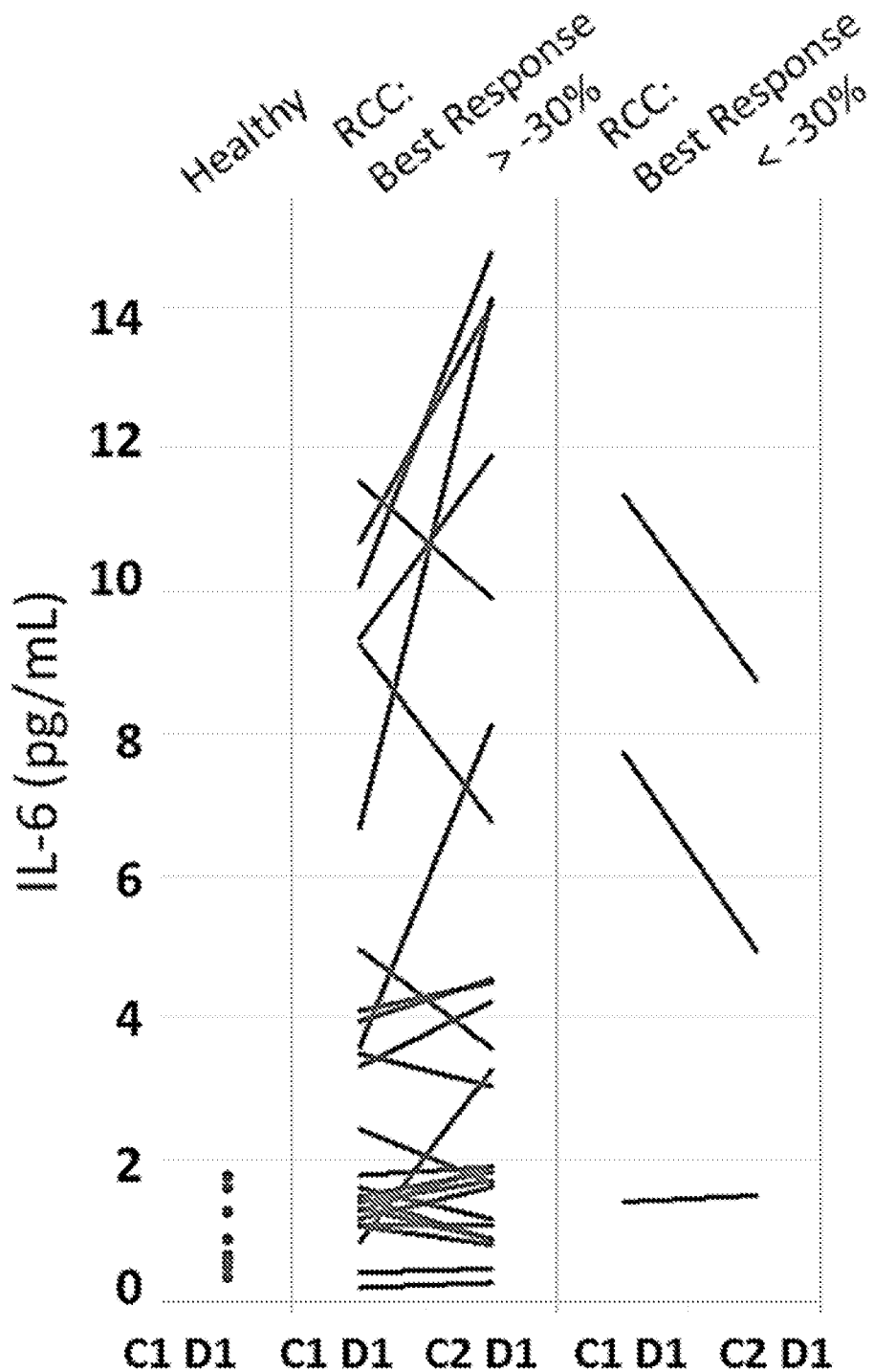
FIGS. 10A and 10B show that IL6 and IL8 levels decreased in blood plasma after treatment in patients who had the best response (reduction in tumor size) to CPI-444 treatment.
Figure 10B:
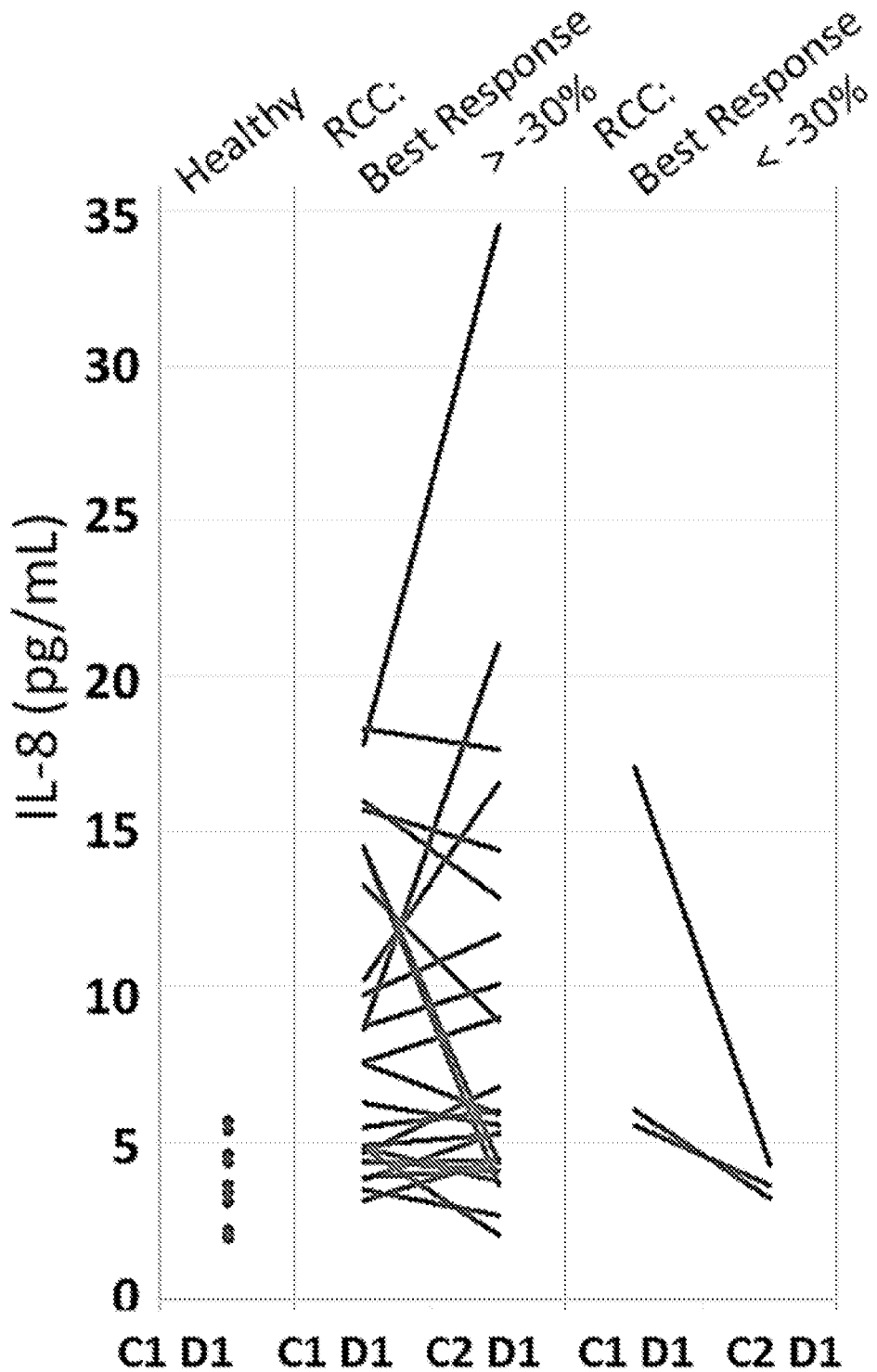
Figure 10C:
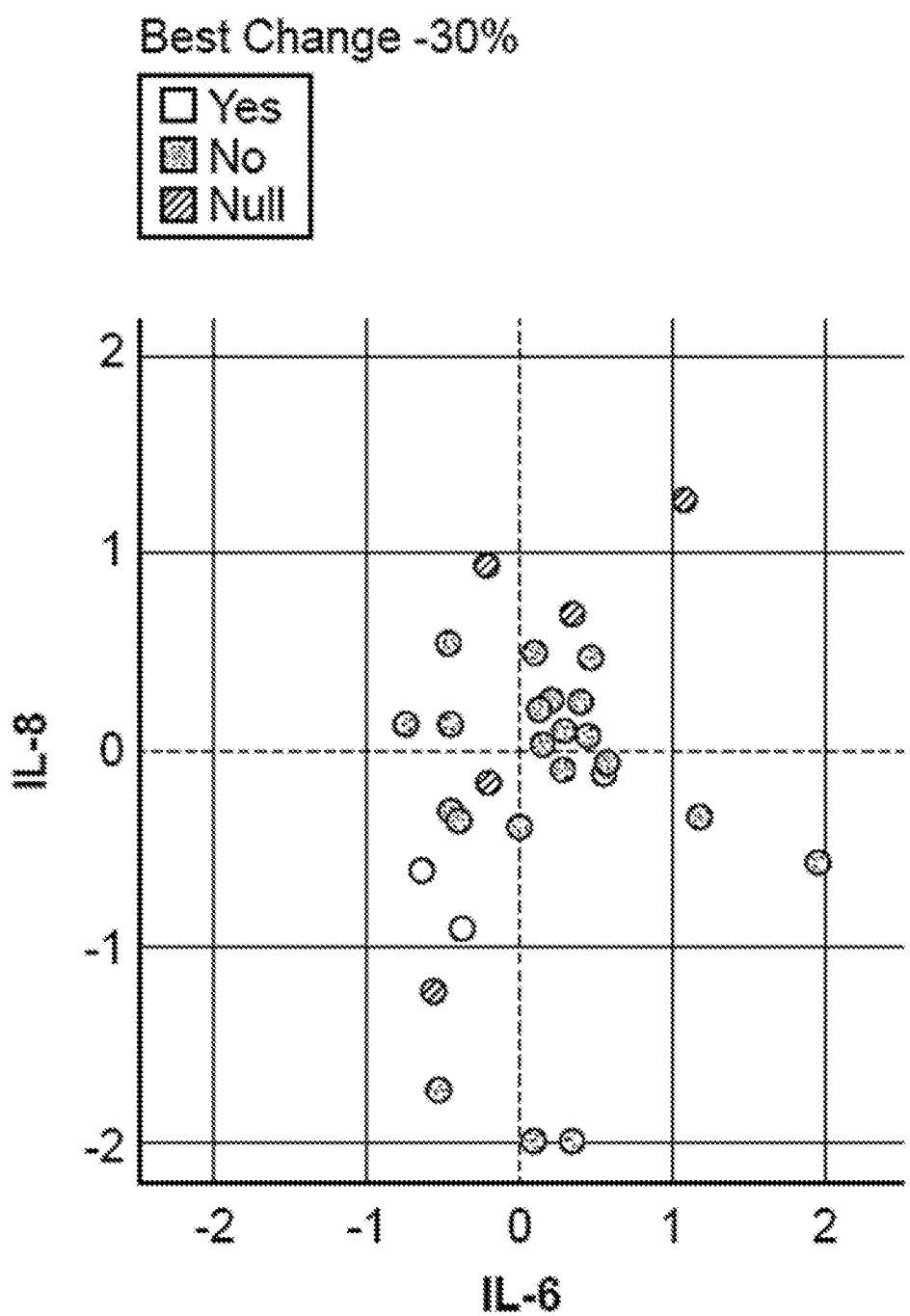
FIG. 10C shows the correlation of the log 2 fold change in IL6 and IL8 levels in blood plasma after treatment in patients who had the best response (reduction in tumor size) to CPI-444 treatment.

Similarly, IL6 (FIG. 9A) and IL8 (FIG. 9B) baseline plasma protein levels were higher in patients with a reduction in tumor size after treatment. Plasma levels of these two cytokines was reduced after treatment (4 weeks) in patients with a reduction in tumor size after treatment (FIGS. 10A, 10B, and 10C).

Figure 11A:
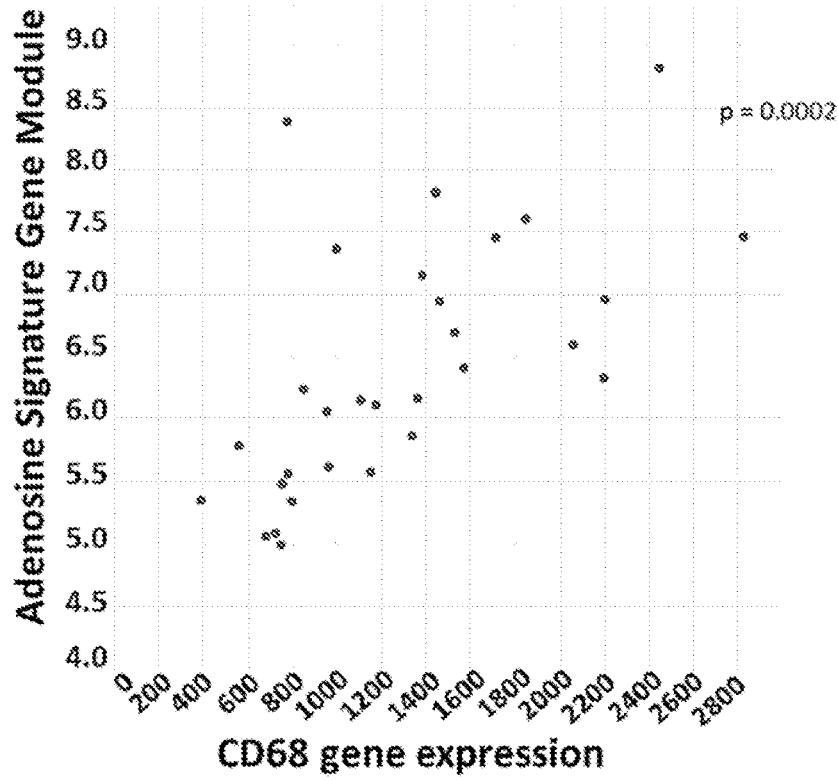
FIGS. 11A and 11B show the correlation of mean log 2 expression of genes in the adenosine composite gene expression module (X axis) with CD68 gene expression (Y axis) in baseline RCC samples (FIG. 11A; p=0.0002) and commercially-available renal cancer tumors (FIG. 11B; p=0.002).
Figure 11B:
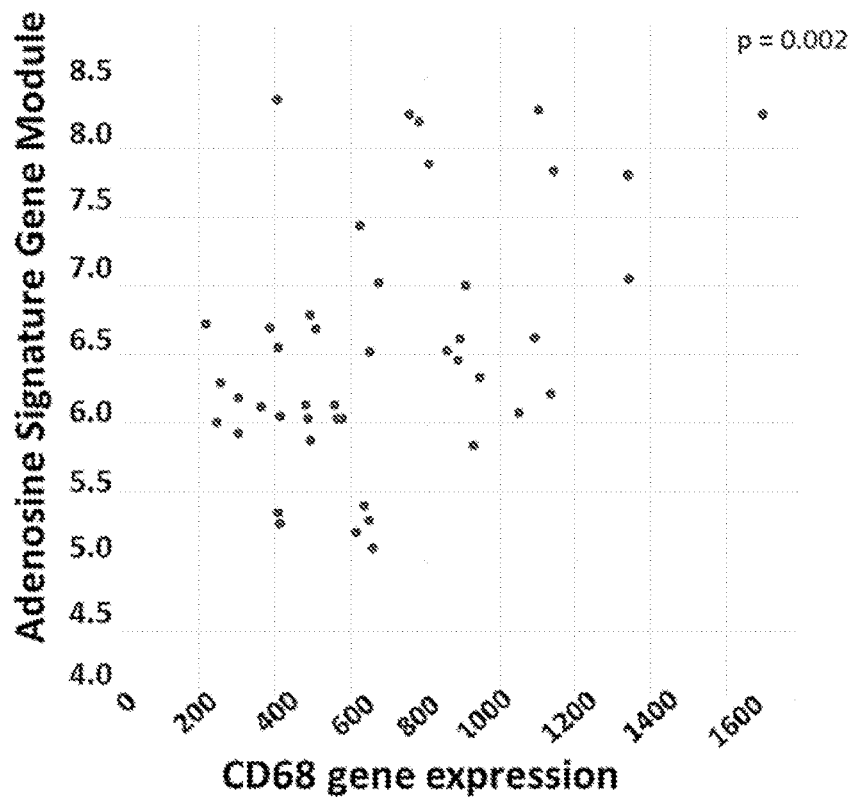

Example 6: Expression of CD68 and CD163 is Correlated with Expression of Adenosine-Regulated Genes in Renal Cancer Gene expression of CD68 and expression of genes in the adenosine signature gene module are highly correlated in solid tumors evaluated in RCC samples prior to treatment (FIG. 11A), as well as in commercially-available renal cancer samples (FIG. 11B).

Figure 12A:
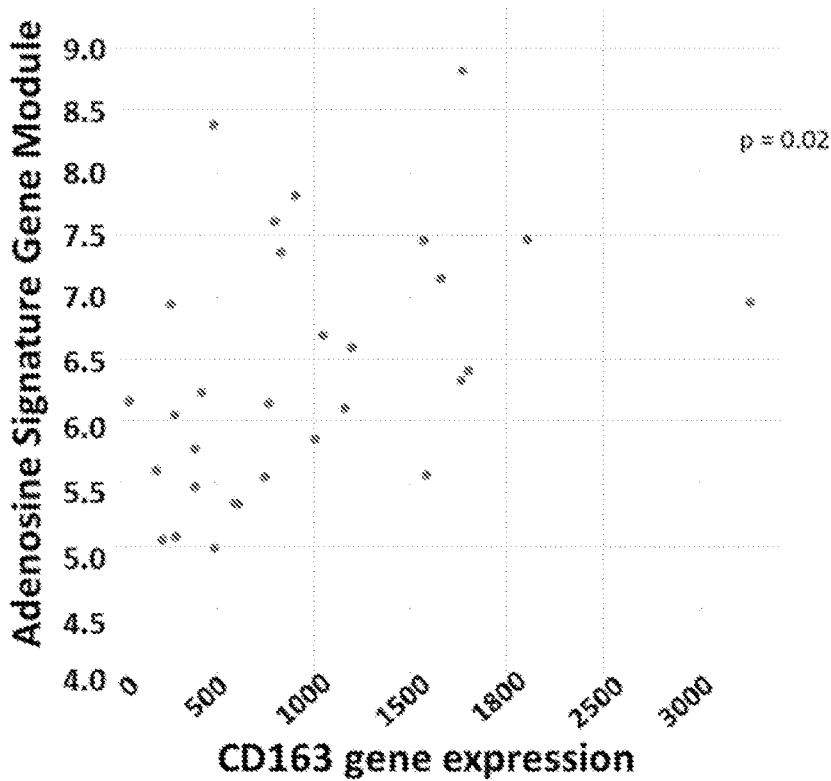
FIGS. 12A and 12B show the correlation of mean log 2 expression of genes in the adenosine composite gene expression module (X axis) with CD163 gene expression (Y axis) in baseline RCC samples (FIG. 11A; p=0.02) and commercially-available renal cancer tumors (FIG. 11B; p=0.001).
Figure 12B:
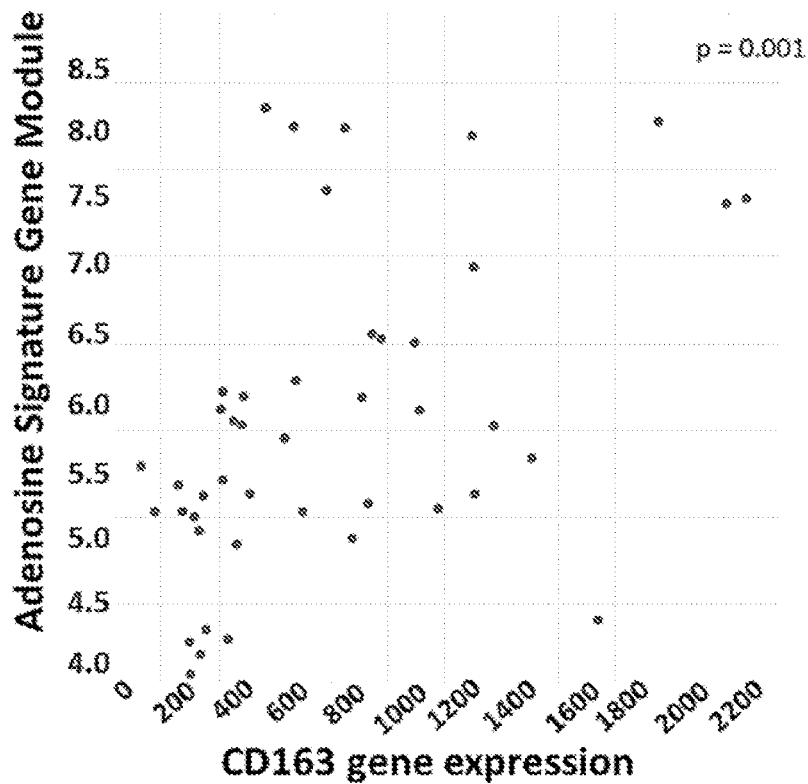

Similarly, gene expression of CD163 and expression of genes in the adenosine signature gene module are highly correlated in solid tumors evaluated in RCC samples prior to treatment (FIG. 12A), as well as in commercially-available renal cancer samples (FIG. 12B).

Figure 11C:
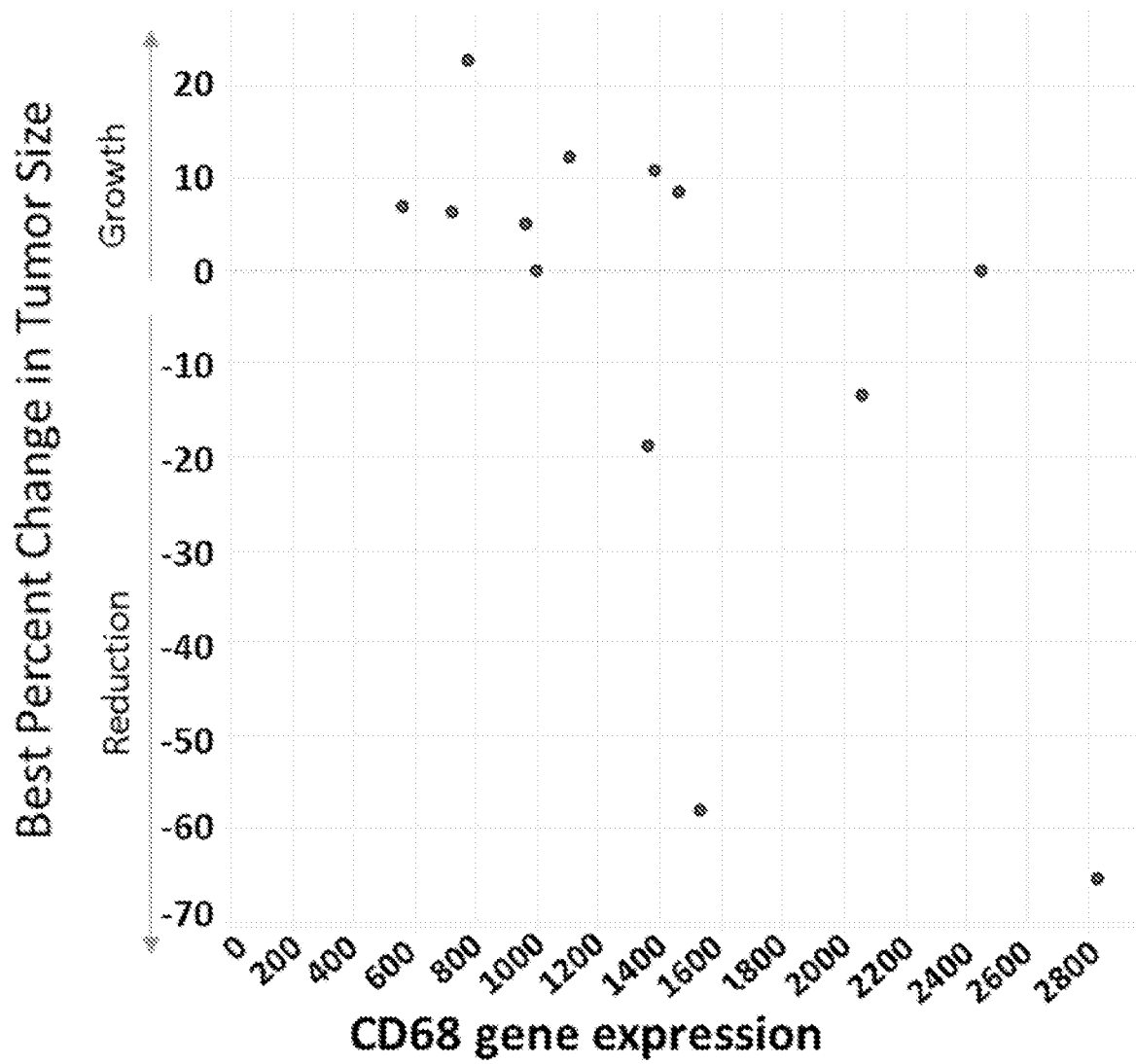
FIG. 11C shows the correlation between the best overall percent change in tumor size after CPI-444 treatment and CD68 gene expression in patients with RCC.
Figure 12C:
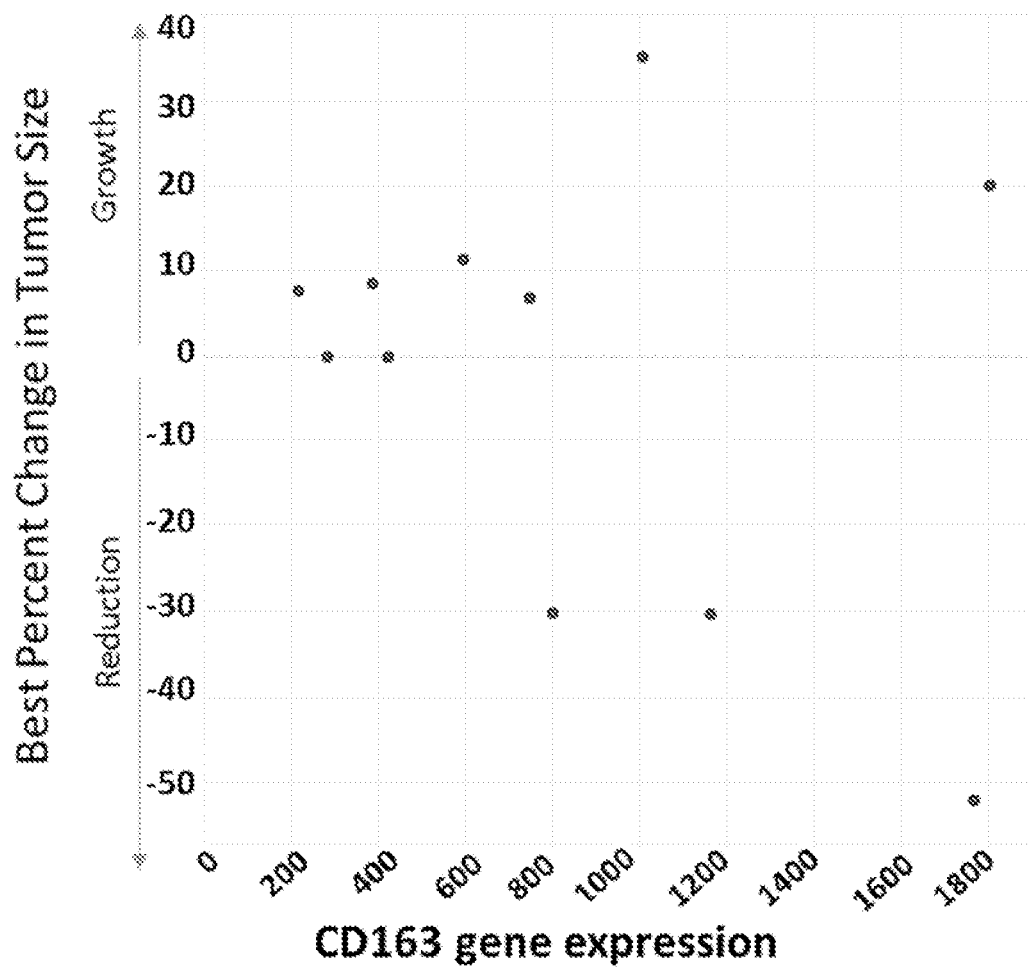
FIG. 12C shows the correlation between the best overall percent change in tumor size after CPI-444 treatment and CD163 gene expression in patients with RCC.

FIGS. 11C and 12C show tumor responses to CPI-444 monotherapy in tumors with baseline expression of CD68 and CD163. Patients with high CD68 or high CD163 gene levels in the tumors were more likely to respond to treatment with CPI-444 than patients with low levels of CD68 or CD163.

CONCLUSION

Expression of a subset of genes that are modulated by adenosine levels correlates with tumor regression in the ongoing Ph 1/1b trial with CPI-444 treatment in RCC. Patients with high expression of the subset of genes were more likely to have tumor regression than those patients with low expression. A2AR agonists induce a specific gene signature dominated by immunosuppressive mediators of MDSC and monocyte/macrophage biology. Inhibition of these genes and proteins by CPI-444 are observed in vitro and in vivo in tumor biopsies from treated patients. These genes and proteins may identify patients with high levels of adenosine and be used as biomarkers for patient selection to select patients most likely to respond to therapy with agents that antagonize adenosine production or signaling.

Example 6: Correlation of Gene Expression with Expression of Adenosine-Regulated Genes in Multiple Cancer Types The expression of eight adenosine-induced immune-related genes (IL1B, PTGS2, and CXCL1, CXCL2, CXCL3, CXCL5, CXCL6, CXCL8) were selected as adenosine-regulated genes because they were expressed at detectable levels in the patient tumor samples from the Ph1/1b clinical trial of CPI-444. A gene expression composite score ("AdenoSig") was calculated as the mean of the Log2 value of the counts for each gene component. The distribution of the AdenoSig for all evaluated RCC patients in the Ph1/1b trial was determined, and an optimal cut-off was selected to differentiate patients with low expression of AdenoSig from high expression.

Figure 13:
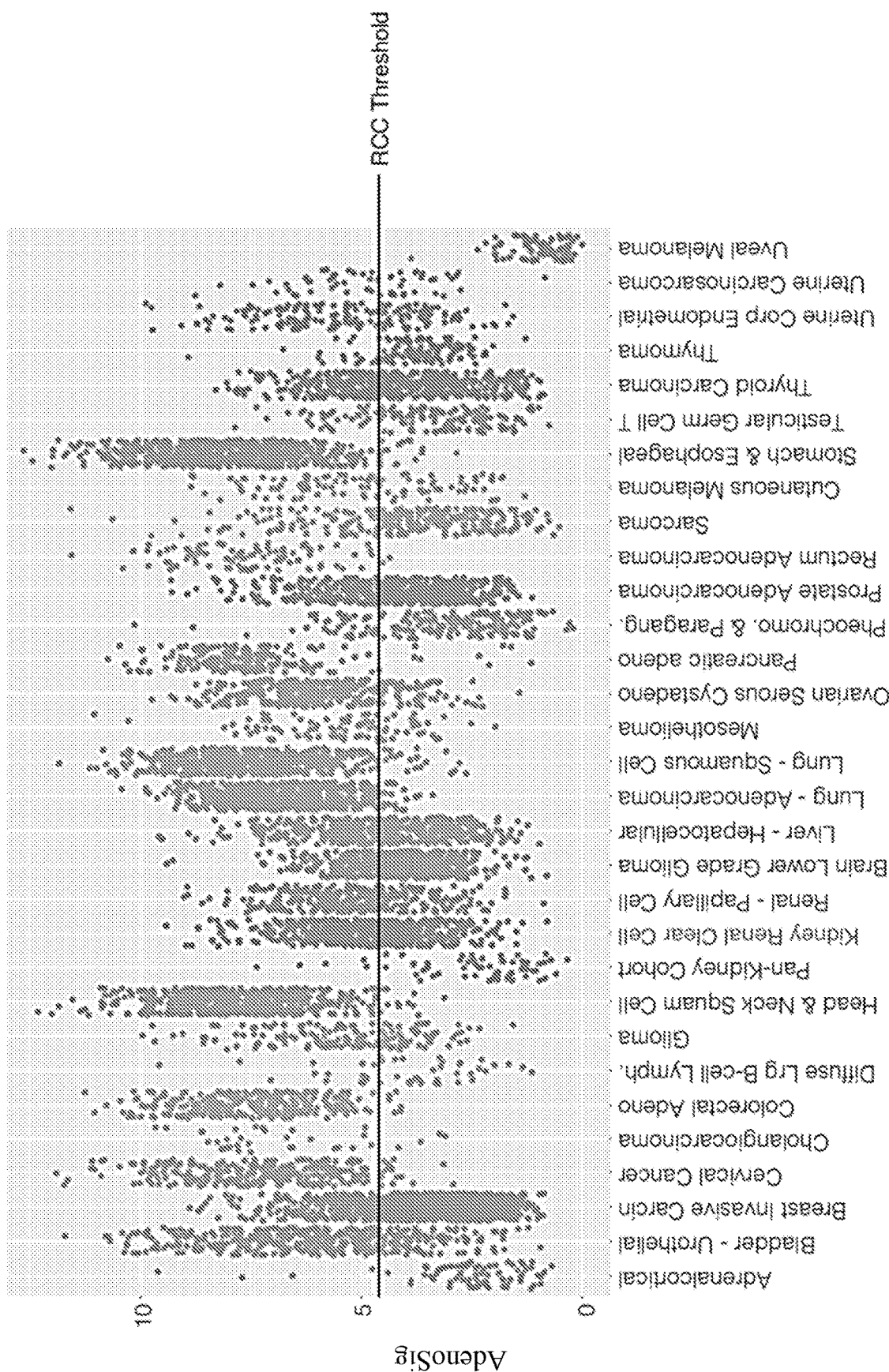
FIG. 13 shows prevalence of AdenoSig within and across tumor types.

AdenoSig expression was next calculated from publicly available tumor gene expression data in The Cancer Genome Atlas (TCGA). The prevalence of AdenoSig within and across tumor types is shown in FIG. 13.

In addition to the eight genes selected to comprise the AdenoSig, additional genes are biologically co-regulated, and could be incorporated in, or serve as a surrogate for, the AdenoSig. In order to identify correlated genes, for 31 tumor types all ~20,000 genes represented in TCGA were correlated with AdenoSig (Spearman's correlation). Within each tumor type, the genes in the top 2% of most highly correlated with AdenoSig were identified. Then, for each gene, the number of tumor types in which the given gene was in the top 2% of all gene correlations was determined. Genes that were in the top 2% of correlations with AdenoSig for at least 15 out of 31 tumor types, meaning that these genes broadly correlate with AdenoSig and are likely part of the same biological process, are shown Table 7. Therefore, expression of these genes identifies similar patients as the AdenoSig and could potentially be used as a set of alternate genes used to calculate an adenosine signature score. Gene names are based on TCGA database. Accessed at www.cancer.gov/about-nci/organization/ccg/research/structural-genomics/tcga.

TABLE 7

Genes in the top 2% of correlations with AdenoSig for at least 15 out of 31 tumor types

| gene | Number of tumor types (out of 31) in which the gene is in the top 2% of gene correlations with AdenoSig | gene | Number of tumor types (out of 31) in which the gene is in the top 2% of gene correlations with AdenoSig |
| --- | --- | --- | --- |
| CXCL1 | 31 | TNFAIP3 | 19 |
| IL8 | 31 | TNFAIP6 | 19 |
| CXCL2 | 30 | CEACAM3 | 18 |
| CXCL3 | 30 | CSF3 | 18 |
| CXCL5 | 30 | FFAR2 | 18 |
| SOCS3 | 30 | GPR183 | 18 |
| IL1B | 28 | SAA1 | 18 |
| BCL2A1 | 27 | SERPINB8 | 18 |
| CCL20 | 27 | SERPINE1 | 18 |
| S100A8 | 27 | SLC11A1 | 18 |
| IL6 | 26 | BCL3 | 17 |
| PLAUR | 26 | C5AR1 | 17 |
| S100A9 | 26 | CCL3 | 17 |
| CXCL6 | 25 | CCL4 | 17 |
| OSM | 25 | CFB | 17 |
| AQP9 | 24 | CLEC7A | 17 |
| IER3 | 24 | GPR109A | 17 |
| NFKBIZ | 24 | IL10 | 17 |
| PTGS2 | 24 | MNDA | 17 |
| FPR1 | 23 | SAMSN1 | 17 |
| PLAU | 23 | SLC2A3 | 17 |
| TREM1 | 23 | SRGN | 17 |
| CCL2 | 22 | ALOX5AP | 16 |
| FCAR | 22 | CLEC5A | 16 |
| FPR2 | 22 | CXCR1 | 16 |
| GPR84 | 22 | GOS2 | 16 |
| ICAM1 | 22 | HBEGF | 16 |
| SERPINB2 | 22 | NAMPT | 16 |
| IL1A | 21 | ZFP36 | 16 |
| MAP3K8 | 21 | C15orf48 | 15 |
| C19orf59 | 20 | CCL7 | 15 |
| FCGR3B | 20 | CD300A | 15 |
| FOSL1 | 20 | CD300E | 15 |
| IL1RN | 20 | CSF3R | 15 |
| LIF | 20 | CXCR2 | 15 |
| LILRA5 | 20 | EMR3 | 15 |
| SOD2 | 20 | FOS | 15 |
| TNF | 20 | GPR109B | 15 |
| VNN3 | 20 | GPR97 | 15 |
| ZC3H12A | 20 | MEFV | 15 |
| BIRC3 | 19 | NCOA7 | 15 |
| EREG | 19 | NLRP3 | 15 |

TABLE 7-continued

Genes in the top 2% of correlations with AdenoSig for at least 15 out of 31 tumor types

| gene | Number of tumor types (out of 31) in which the gene is in the top 2% of gene correlations with AdenoSig | gene | Number of tumor types (out of 31) in which the gene is in the top 2% of gene correlations with AdenoSig |
| --- | --- | --- | --- |
| GNA15 | 19 | PPBP | 15 |
| JUNB | 19 | RND3 | 15 |
| PI3 | 19 | S100A12 | 15 |
|  |  | SAA2 | 15 |

In identifying genes that correlate with AdenoSig, it should be recognized that alternate methods could be utilized. For example, instead identifying the top 2% of most highly correlated genes with AdenoSig that appear in at least 15 of 31 tumor types, the threshold could be adjusted to select the top 3% of genes that correlate with AdenoSig in at least 14/31 tumor types. See Table 8. Alternatively, genes could be selected by having a Spearman's correlation value with AdenoSig of at least 0.5 in at least 15 out of 31 tumor types in TCGA. See Table 9.

TABLE 8

Genes in the top 3% of correlations with AdenoSig for at least 14 out of 31 tumor types.

| gene | Gene Name | Number of indications (out of 31) where gene is in top 3% of all gene correlations |
| --- | --- | --- |
| CXCL1 | C-X-C Motif Chemokine Ligand 1 | 31 |
| IL8 | Interleukin 8 | 31 |
| CXCL2 | C-X-C Motif Chemokine Ligand 2 | 30 |
| CXCL3 | C-X-C Motif Chemokine Ligand 3 | 30 |
| CXCL5 | C-X-C Motif Chemokine Ligand 5 | 30 |
| SOCS3 | Suppressor Of Cytokine Signaling 3 | 30 |
| CCL20 | C-C motif chemokine ligand 20 | 29 |
| IL1B | Interleukin 1 Beta | 29 |
| PLAUR | plasminogen activator, urokinase receptor | 29 |
| BCL2A1 | BCL2 related protein A1 | 28 |
| IL6 | Interleukin 6 | 28 |
| S100A8 | S100 calcium binding protein A8 | 28 |
| NFKBIZ | NFKB inhibitor zeta | 27 |
| OSM | oncostatin M | 27 |
| PLAU | plasminogen activator, urokinase | 27 |
| S100A9 | S100 calcium binding protein A9 | 27 |
| CXCL6 | C-X-C Motif Chemokine Ligand 6 | 26 |
| FPR1 | formyl peptide receptor 1 | 26 |
| IER3 | immediate early response 3 | 26 |
| PTGS2 | Prostaglandin-endoperoxide synthase | 26 |
| TREM1 | triggering receptor expressed on myeloid cells 1 | 26 |
| CCL2 | C-C motif chemokine ligand 2 | 25 |
| FPR2 | formyl peptide receptor 2 | 25 |
| AQP9 | aquaporin 9 | 24 |
| FCAR | Fc fragment of IgA receptor | 24 |
| GPR84 | G Protein-Coupled Receptor84 | 24 |
| IL1A | Interleukin 1 Alpha | 24 |
| MAP3K8 | mitogen-activated protein kinase kinase kinase 8 | 24 |
| ICAM1 | intercellular adhesion molecule 1 | 23 |
| SERPINB2 | serpin family B member 2 | 23 |
| C19orf59 | chromosome 19 open reading frame 59 | 22 |
| CSF3R | colony stimulating factor 3 receptor | 22 |
| JUNB | JunB proto-oncogene, AP-1 transcription factor subunit | 22 |

TABLE 8-continued

Genes in the top 3% of correlations with AdenoSig for at least 14 out of 31 tumor types.

| gene | Gene Name | Number of indications (out of 31) where gene is in top 3% of all gene correlations |
|---|---|---|
| LIF | leukemia inhibitory factor | 22 |
| PI3 | peptidase inhibitor 3 | 22 |
| SLC11A1 | Natural resistance-associated macrophage protein 1 | 22 |
| CFB | complement factor B | 21 |
| EREG | epiregulin | 21 |
| FOSL1 | FOS like 1, AP-1 transcription factor subunit | 21 |
| IL10 | Interleukin 10 | 21 |
| ILIRN | interleukin 1 receptor antagonist | 21 |
| LILRA5 | leukocyte immunoglobulin like receptor A5 | 21 |
| SAA2 | serum amyloid A2 | 21 |
| SLC2A3 | solute carrier family 2 member 3 | 21 |
| SOD2 | Superoxide dismutase 2, mitochondrial | 21 |
| TNF | tumor necrosis factor | 21 |
| TNFAIP6 | TNF Alpha Induced Protein 6 | 21 |
| VNN3 | Vanin 3 | 21 |
| BIRC3 | baculoviral IAP repeat containing 3 | 20 |
| C5AR1 | complement C5a receptor 1 | 20 |
| CCL3 | C-C motif chemokine ligand 3 | 20 |
| CEACAM3 | carcinoembryonic antigen related cell adhesion molecule 3 | 20 |
| CSF2RB | colony stimulating factor 2 receptor beta common subunit | 20 |
| FCGR3B | Fc fragment of IgG receptor IIIb | 20 |
| GNA15 | G protein subunit alpha 15 | 20 |
| GPR183 | G Protein-Coupled Receptor 183 | 20 |
| SERPINE1 | serpin family E member 1 | 20 |
| TNFAIP3 | TNF Alpha Induced Protein 3 | 20 |
| ZC3H12A | Zinc finger CCCH-type containing 12A | 20 |
| BCL3 | B-cell lymphoma 3 | 19 |
| CCL7 | C-C motif chemokine ligand 7 | 19 |
| CLEC7A | C-type lectin domain family 7 member A | 19 |
| CSF3 | Colony Stimulating Factor 3 | 19 |
| CXCR1 | C-X-C motif chemokine receptor 1 | 19 |
| CYR61 | Cysteine-rich angiogenic inducer 61 | 19 |
| FFAR2 | free fatty acid receptor 2 | 19 |
| GPR109A | G Protein-Coupled Receptor 109A | 19 |
| GPR109B | G Protein-Coupled Receptor 109B | 19 |
| LILRB3 | leukocyte immunoglobulin like receptor B3 | 19 |
| NAMPT | nicotinamide phosphoribosyltransferase | 19 |
| NNMT | nicotinamide N-methyltransferase | 19 |
| PLK3 | polo like kinase 3 | 19 |
| RND3 | Rho family GTPase 2 | 19 |
| S100A12 | S100 calcium binding protein A12 | 19 |
| SAA1 | serum amyloid A1 | 19 |
| SAMSN1 | SAM domain, SH3 domain and nuclear localization signals 1 | 19 |
| SERPINB8 | serpin family B member 8 | 19 |
| SLC2A14 | solute carrier family 2 member 14 | 19 |
| VNN2 | Vanin 2 | 19 |
| ALOX5AP | arachidonate 5-lipoxygenase activating protein | 18 |
| C15orf48 | chromosome 15 open reading frame 48 | 18 |
| CCL8 | C-C motif chemokine ligand 8 | 18 |
| CLEC5A | C-type lectin domain family 5 member A | 18 |
| EMR2 | EGF-like module-containing mucin-like hormone receptor-like 2 | 18 |
| EMR3 | EGF-like module-containing mucin-like hormone receptor-like 3 | 18 |
| FCGR2A | Fc fragment of IgG receptor IIa | 18 |
| HBEGF | heparin binding EGF like growth factor | 18 |
| MMP1 | matrix metallopeptidase 1 | 18 |
| NLRP3 | NLR family, pyrin domain containing 3 | 18 |
| PPBP | Pro-Platelet Basic Protein | 18 |
| TLR2 | toll like receptor 2 | 18 |
| VNN1 | vanin 1 | 18 |
| C1R | complement component 1, r subcomponent | 17 |
| CCL4 | C-C motif chemokine ligand 4 | 17 |
| CD300A | CD300 antigen-like family member A | 17 |
| CD300LB | CD300 molecule like family member b | 17 |
| CD53 | Cluster of Differentiation 53 | 17 |
| CD69 | Cluster of Differentiation 69 | 17 |
| CD86 | Cluster of Differentiation 86 | 17 |
| CXCR2 | C-X-C motif chemokine receptor 2 | 17 |
| DUSP1 | dual specificity phosphatase 1 | 17 |
| GLIPR1 | Glioma pathogenesis related 1 | 17 |
| LILRB2 | leukocyte immunoglobulin like receptor B2 | 17 |
| MCL1 | myeloid cell leukemia 1 apoptosis regulator, BCL2 family member | 17 |
| MEFV | MEFV innate immunity regulator, pyrin | 17 |
| MNDA | myeloid cell nuclear differentiation antigen | 17 |
| SRGN | Serglycin | 17 |
| STX11 | syntaxin-11 | 17 |
| AREG | amphiregulin | 16 |
| CCL4L2 | C-C motif chemokine ligand 4 like 2 | 16 |
| CDCP1 | CUB domain containing protein 1 | 16 |
| CLEC4A | C-type lectin domain family 4 member A | 16 |
| EGR3 | early growth response 3 | 16 |
| FGR | FGR proto-oncogene, Src family tyrosine kinase | 16 |
| FOS | Fos proto-oncogene, AP-1 transcription factor subunit | 16 |
| G0S2 | G0/G1 switch 2 | 16 |
| GPR97 | G Protein-Coupled Receptor 97 | 16 |
| IL1R2 | interleukin 1 receptor type 2 | 16 |
| KLF6 | Kruppel like factor 6 | 16 |
| LAMC2 | laminin subunit gamma 2 | 16 |
| LCP2 | lymphocyte cytosolic protein 2 | 16 |
| MMP12 | matrix metallopeptidase 12 | 16 |
| NCF2 | neutrophil cytosolic factor 2 | 16 |
| PHLDA1 | pleckstrin homology like domain family A member 1 | 16 |
| PLEK | pleckstrin | 16 |
| PRDM1 | PR domain containing 1, with ZNF domain | 16 |
| PTPN22 | protein tyrosine phosphatase non-receptor type 22 | 16 |
| SELE | selectin E | 16 |
| SNAI1 | snail family transcriptional repressor 1 | 16 |
| ZFP36 | zinc finger protein 36 homolog | 16 |
| ACTBL2 | Actin, Beta Like 2 | 15 |
| ANXA2P2 | annexin A2 pseudogene 2 | 15 |
| BDKRB2 | bradykinin receptor B2 | 15 |
| C1orf38 | chromosome 1 open reading frame 38 | 15 |
| C3 | complement component 3 | 15 |
| CCL3L1 | C-C motif chemokine ligand 3 like 1 | 15 |
| CCR1 | C-C motif chemokine receptor 1 | 15 |
| CD300E | CD300 antigen-like family member E | 15 |
| CLEC4E | C-type lectin domain family 4 member E | 15 |
| CSF2 | colony stimulating factor 12 | 15 |
| DAPP1 | dual adaptor of phosphotyrosine and 3-phosphoinositides 1 | 15 |
| DUSP5 | dual specificity phosphatase 5 | 15 |
| EMP1 | epithelial membrane protein 1 | 15 |
| HAS1 | hyaluronan synthase 1 | 15 |
| HCK | hemopoietic cell kinase proto-oncogene, Src family tyrosine kinase | 15 |
| ILIRL1 | interleukin 1 receptor like 1 | 15 |
| LRG1 | leucine rich alpha-2-glycoprotein 1 | 15 |
| MMP3 | matrix metallopeptidase 3 | 15 |
| MMP7 | matrix metallopeptidase 7 | 15 |
| NCOA7 | nuclear receptor coactivator 7 | 15 |
| NFE2 | nuclear factor, erythroid 2 | 15 |
| OBFC2A | nucleic acid binding protein 1 | 15 |
| OSMR | oncostatin M receptor | 15 |
| RGS2 | regulator of G protein signaling 2 | 15 |
| RND1 | Rho family GTPase 1 | 15 |
| SERPINB4 | serpin family B member 4 | 15 |
| THBS1 | Thrombospondin 1 | 15 |

TABLE 8-continued

Genes in the top 3% of correlations with AdenoSig for at least 14 out of 31 tumor types.

| gene | Gene Name | Number of indications (out of 31) where gene is in top 3% of all gene correlations |
|---|---|---|
| TNFAIP2 | TNF Alpha Induced Protein 2 | 15 |
| TNIP3 | TNFAIP3 Interacting Protein 3 | 15 |
| ADAM8 | a disintegrin and metallopeptidase domain 8 | 14 |
| ARHGAP9 | Rho GTPase activating protein 9 | 14 |
| C10orf55 | chromosome 10 open reading frame 55 | 14 |
| C1S | complement component 1, s subcomponent | 14 |
| C8orf4 | chromosome 8 open reading frame 4 | 14 |
| CASP4 | caspase 4 | 14 |
| CCL18 | C-C motif chemokine ligand 18 | 14 |
| CD14 | cluster of differentiation 14 | 14 |
| CLEC4D | C-type lectin domain family 4 member D | 14 |
| CXorf21 | chromosome X open reading frame 21 | 14 |
| CYTH4 | cytohesin 4 | 14 |
| CYTIP | cytohesin 1 interacting protein | 14 |
| F3 | coagulation factor III, tissue factor | 14 |
| FCER1G | Fc fragment of IgE receptor Ig | 14 |
| FCGR2B | Fc fragment of IgG receptor Iib | 14 |
| GPRC5A | G protein-coupled receptor class C group 5 member A | 14 |
| HK3 | hexokinase 3 | 14 |
| IL4R | interleukin 4 receptor | 14 |
| IL7R | Interleukin 7 Receptor | 14 |
| LILRA6 | leukocyte immunoglobulin like receptor A6 | 14 |
| LYN | LYN proto-oncogene, Src family tyrosine kinase | 14 |
| MAFF | MAF bZIP transcription factor F | 14 |
| MYO1G | myosin IG | 14 |
| NCF4 | neutrophil cytosolic factor 4 | 14 |
| P2RY6 | pyrimidinergic receptor P2Y6 | 14 |
| PF4V1 | platelet factor 4 variant 1 | 14 |
| PPP1R15A | protein phosphatase 1, regulatory subunit 15A | 14 |
| RARRES1 | retinoic acid receptor responder 1 | 14 |
| RASGRP4 | RAS guanyl releasing protein 4 | 14 |
| RGS1 | regulator of G protein signaling 1 | 14 |
| SAA4 | serum amyloid A4 | 14 |
| SAT1 | spermidine/spermine N1-acetyltransferase 1 | 14 |
| SERPINA1 | serpin family A member 1 | 14 |
| SERPINB7 | serpin family B member 7 | 14 |
| SPI1 | Spleen Focus Forming Virus (SFFV) Proviral Integration Oncogene | 14 |
| TDO2 | Tryptophan 2,3-Dioxygenase | 14 |
| TGM2 | Transglutaminase 2 | 14 |

TABLE 9

Genes having a Spearman's correlation value with AdenoSig of at least 0.5 in at least 15 out of 31 tumor types

| gene name | Number of indications (out of 31) where Spearman's correlation >0.5 |
|---|---|
| CXCL1 | 31 |
| IL8 | 31 |
| CXCL3 | 30 |
| CXCL2 | 29 |
| CXCL5 | 29 |
| IL1B | 26 |
| SOCS3 | 25 |
| IL6 | 23 |
| CCL20 | 22 |
| CXCL6 | 22 |
| BCL2A1 | 20 |
| PTGS2 | 19 |
| S100A8 | 19 |
| OSM | 18 |
| PLAUR | 18 |
| FCGR3B | 16 |
| IER3 | 16 |
| NFKBIZ | 16 |
| CCL2 | 15 |
| CSF3 | 15 |
| FPR2 | 15 |
| S100A9 | 15 |
| TREM1 | 15 |

REFERENCES

1. Katoh et al., "CXCR2-Expressing Myeloid-Derived Suppressor Cells are Essential to Protein Colitis-Associated Tumorigenesis," Cancer Cell
2. Steele et al., "CXCR2 Inhibition Profoundly Suppresses Metastases and Augments Immunotherapy in Pancreatic Ductal Adenocarcinoma," Cancer Cell
3. Willingham S, et al. Identification of Adenosine Pathway Genes Associated with Response to Therapy with the Adenosine Receptor Antagonist CPI-444. European Society for Medical Oncology poster presentation. Munich, Germany, 2018.

Embodiments

Embodiment 1. A method for detecting a level of expression of one or more genes in a subject having or suspected of having cancer, the method including:
 a) obtaining a biological sample from the subject; and
 b) detecting the level of expression of the one or more genes in the biological sample, wherein the genes are selected from CD68, CD163, BIRC5, BST1, CARD11, CCL2, CCL3, CCL7, CCL24, CCNE1, CD14, CD300E, CD86, CD93, CDK1, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, IL1A, IL-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, C1R, C1S, C4BPA, CCL11, CCL20, CXCL16, CXCL2, HAMP, HSD11B1, ITGAM, LIF, SAA1, TFRC, TLR5, TNFRSF11A, TNFSF14, TREM1, TREM2, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, LBP, MAP2K2, PRAME, PSMD7, TNFSF18, APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CD36, CDH1, CDH5, CREB1, DOCK9, ENG, HMGB1, ITGA1, JAM3, MAF, MAPK3, MAPK8, MCAM, MFGE8, MIF, NOTCH1, NRP1, PRKCE, RORA, TLR3, SMAD2, TAL1, THY1, TNFSF12, TRAF6, TXNIP, VEGFA, S100A8, and/or WDR83OS.

Embodiment 2. The method of embodiment 1, wherein the genes are selected from CCL2, CCL3, CCL7, CD300E, CD93, CSF3, CXCL1, CXCL2, CXCL3, CXCL5, CXCL8, ECEL1, HAS1, IL-1β, IL8, IL23, INHBA, PADI2, PID1, PTGS2, SCL747, SERPINB2, ST6GALNAC2, and/or THBS1.

Embodiment 3. The method of embodiment 2, wherein the genes are selected from CXCL1, CXCL2, CXCL3, CXCL5, SERPINB2, IL8, and/or IL-1β.

Embodiment 3-1. The method of embodiment 1, wherein the genes are selected from IL1β, PTGS2, CXCL1, CXCL2, CXCL3, CXCL5, CXCL6, and/or CXCL8.

Embodiment 4. The method of embodiment 1, wherein the genes are selected from CCL24, CCNE1, EHF, FUT7, GALM, GBP6, IL5, LAP3, MRPL11, OST4, WDR83OS, and/or TBX21.

Embodiment 5. The method of embodiment 4, wherein the genes are selected from EHF, FUT7, and/or OST4.

Embodiment 6. The method of embodiment 1, wherein the one or more genes include CCL20 and CX3CL1.

Embodiment 7. The method of embodiment 6, wherein CCL20 expression in the biological sample is higher than a control, and CX3CL1 expression in the biological sample is lower than the control.

Embodiment 8. The method of any one of embodiments 1-7, wherein the one or more genes include IL6.

Embodiment 9. The method of embodiment 8, wherein IL6 expression in the biological sample is higher than a control.

Embodiment 10. The method of any one of embodiments 1-9, wherein the one or more genes include IL8.

Embodiment 11. The method of embodiment 10, wherein IL8 expression in the biological sample is higher than a control.

Embodiment 12. The method of any one of embodiments 1-9, wherein the one or more genes include CD68.

Embodiment 13. The method of any one of embodiments 1-9, wherein the one or more genes include CD163.

Embodiment 14. The method of embodiment 1, wherein the genes are selected from CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1B, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18.

Embodiment 15. The method of embodiment 14, wherein the genes are selected from BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18.

Embodiment 16. The method of embodiment 1, wherein the genes are selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA.

Embodiment 17. The method of embodiment 16, wherein the genes are selected from AKT3, BMI1, CD164, CD34, CD36, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, VEGFA, APP, ATG10, BCL2, CCL15, CD24, CD46, CD59, CDH1, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, MIF, PPARG, RORA, RORC, SPA17, STAT5B, TLR3, and/or TOLLIP.

Embodiment 18. The method of any one of embodiments 1 to 17, wherein expression of other genes is not detected.

Embodiment 19. The method of any one of embodiments 1 to 18, wherein the biological sample is selected from a blood sample, a tumor biopsy, or immune cells.

Embodiment 20. The method of embodiment 19, wherein the biological sample is a tumor biopsy.

Embodiment 21. The method of any one of embodiments 1 to 20, wherein gene expression is measured by RNA sequencing, nanopore sequencing, microarray, or hybridization-based sequencing (e.g., NanoString).

Embodiment 22. The method of any one of embodiments 1 to 21, further including: (c) comparing the level of expression of the one or more genes in the sample to a level of expression of the one or more genes in a suitable control.

Embodiment 23. The method of embodiment 22, wherein the suitable control is a sample from a healthy subject, a sample from a non-cancerous tissue, or an average level of expression in a population.

Embodiment 24. The method of any one of embodiments 1-23, further including determining a CD68 protein level and/or a CD163 protein level in the cancer.

Embodiment 25. The method of embodiment 24, wherein the CD68 protein level and/or the CD163 protein level is determined by immunohistochemistry.

Embodiment 26. A method of treating a subject having cancer, the method including:
  (a) obtaining a biological sample from the subject;
  (b) detecting a level of expression of one or more genes in the biological sample, wherein the genes are selected from CD68, CD163, BIRC5, BST1, CARD11, CCL2, CCL3, CCL7, CCL24, CCNE1, CD14, CD300E, CD86, CD93, CDK1, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, IL1A, IL-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, C1R, C1S, C4BPA, CCL11, CCL20, CXCL16, CXCL2, HAMP, HSD11B1, ITGAM, LIF, SAA1, TFRC, TLR5, TNFRSF11A, TNFSF14, TREM1, TREM2, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, LBP, MAP2K2, PRAME, PSMD7, TNFSF18, APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CD36, CDH1, CDH5, CREB1, DOCK9, ENG, HMGB1, ITGA1, JAM3, MAF, MAPK3, MAPK8, MCAM, MFGE8, MIF, NOTCH1, NRP1, PRKCE, RORA, TLR3, SMAD2, TAL1, THY1, TNFSF12, TRAF6, TXNIP, VEGFA, S100A8, and/or WDR83OS; and (c) administering to the subject an effective amount of an adenosine pathway inhibitor, thereby treating the cancer.

Embodiment 27. The method of embodiment 26, wherein the adenosine pathway inhibitor is an A2A receptor (ADORA2A) antagonist.

Embodiment 28. The method of embodiment 27, wherein the ADORA2A antagonist is CPI-444.

Embodiment 29. The method of embodiment 26, wherein the adenosine pathway inhibitor is is a CD73 antagonist, a CD38 antagonist, a CD39 antagonist, or adenosine deaminase.

Embodiment 30. The method of embodiment 29, wherein the CD73 antagonist is an anti-CD73 antibody.

Embodiment 31. The method of any one of embodiments 26 to 30, further including administering a CXCR2 inhibitor to the subject.

Embodiment 32. The method of embodiment 31, wherein the CXCR2 inhibitor is selected from AZD5069, anti-CXCR2 antibody, and Navarixin.

Embodiment 33. The method of any one of embodiments 26 to 32, wherein the one or more genes include CCL20 and CX3CL1.

Embodiment 34. The method of embodiment 33, wherein CCL20 expression in the biological sample is higher than a control, and CX3CL1 expression in the biological sample is lower than the control.

Embodiment 35. The method of any one of embodiments 26 to 34, wherein the one or more genes include IL6.

Embodiment 36. The method of embodiment 35, wherein IL6 expression in the biological sample is higher than a control.

Embodiment 37. The method of any one of embodiments 26 to 36, wherein the one or more genes include IL8.

Embodiment 38. The method of embodiment 37, wherein IL8 expression in the biological sample is higher than a control.

Embodiment 39. The method of any one of embodiments 26 to 32, wherein the genes are selected from CCL2, CCL3, CCL7, CD300E, CD93, CSF3, CXCL1, CXCL2, CXCL3, CXCL5, CXCL8, ECEL1, HAS1, IL-1β, IL8, IL23, INHBA, PADI2, PID1, PTGS2, SCL747, SERPINB2, ST6GALNAC2, and/or THBS1.

Embodiment 40. The method of embodiment 26, wherein the genes are selected from CXCL1, CXCL2, CXCL3, CXCL5, SERPINB2, IL8, and/or IL-1β.

Embodiment 40-1. The method of embodiment 26, wherein the genes are selected from IL1B, PTGS2, CXCL1, CXCL2, CXCL3, CXCL5, CXCL6, and/or CXCL8.

Embodiment 41. The method of any one of embodiments 26 to 40, wherein the one or more genes include CD68.

Embodiment 42. The method of any one of embodiments 26 to 40, wherein the one or more genes include CD163.

Embodiment 43. The method of any one of embodiments 1-32, wherein the genes are selected from CCL24, CCNE1, EHF, FUT7, GALM, GBP6, IL5, LAP3, MRPL11, OST4, WDR83OS, and/or TBX21.

Embodiment 44. The method of embodiment 43, wherein the genes are selected from EHF, FUT7, and/or OST4.

Embodiment 45. The method of any one of embodiments 1-32, wherein the genes are selected from BIRC5, BST1, C4BPA, CARD11, CCL11, CDK1, CLEC5A, CXCL1, CXCL2, CXCL6, LIF, PTGS2, SAA1, SLC11A1, TNFRSF11A, TREM1, TTK, ADA, BCL6, C1R, C1S, C2, CCL20, CCL8, CD14, CEBPB, CFD, CSF1, CSF2RB, CXCR4, FCGR2A, IFI16, IL8, IRAK4, LY96, LYN, PLAUR, RIPK2, STAT2, STAT3, TLR5, TNFSF14, TNFSF4, ALCAM, C9, CCR6, CEACAM6, CT45A1, CXCL3, CXCL5, CXCR1, CXCR2, DMBT1, FOXJ1, ITCH, LBP, MAP2K2, PRAME, PSMD7, and/or TNFSF18.

Embodiment 46. The method of any one of embodiments 1-32, wherein the genes are selected from AKT3, BMI1, CD164, CD34, CD36, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, VEGFA, APP, ATG10, BCL2, CCL15, CD24, CD46, CD59, CDH1, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, MIF, PPARG, RORA, RORC, SPA17, STAT5B, TLR3, and/or TOLLIP.

Embodiment 47. The method of any one of embodiments 1-46, wherein expression of other genes is not detected.

Embodiment 48. The method of any one of embodiments 1-47, wherein the biological sample is selected from a blood sample, a tumor biopsy, or immune cells.

Embodiment 49. The method of embodiment 48, wherein the biological sample is a tumor biopsy.

Embodiment 50. The method of any one of embodiments 1 to 49, wherein gene expression is measured by RNA sequencing, nanopore sequencing, microarray, or hybridization-based sequencing (e.g., NanoString).

Embodiment 51. The method of any one of embodiments 26 to 50, further including determining a CD68 protein level and/or a CD163 protein level in the cancer.

Embodiment 52. The method of embodiment 51, wherein the CD68 protein level and/or the CD163 protein level is determined by immunohistochemistry.

Embodiment 53. A method for detecting a level of expression of one or more genes in a subject having or suspected of having cancer, the method including:
(a) obtaining a biological sample from the subject; and
(b) detecting the level of expression of the one or more genes in the biological sample, wherein the genes are selected from CD68, CD163, LBP, CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1B, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, TREM2, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, and/or TNFSF18;
wherein a level of expression of the one or more genes that is higher than a control indicates that the subject is a candidate for treatment with an adenosine pathway inhibitor.

Embodiment 54. The method embodiment 53, wherein the one or more genes include IL6.

Embodiment 55. The method of embodiment 53 or 54, wherein the one or more genes include IL8.

Embodiment 56. The method of embodiment 53, wherein the genes are selected from CCL2, CCL3, CCL7, CD300E, CD93, CSF3, CXCL1, CXCL2, CXCL3, CXCL5, CXCL8, ECEL1, HAS1, IL-1β, IL8, IL23, INHBA, PADI2, PID1, PTGS2, SCL747, SERPINB2, ST6GALNAC2, and/or THBS1.

Embodiment 57. The method of any one of embodiments 53 to 56, wherein the genes are selected from BIRC5, BST1, C4BPA, CARD11, CCL11, CDK1, CLEC5A, CXCL1, CXCL2, CXCL6, LIF, PTGS2, SAA1, SLC11A1, TNFRSF11A, TREM1, TTK, ADA, BCL6, C1R, C1S, C2, CCL20, CCL8, CD14, CEBPB, CFD, CSF1, CSF2RB, CXCR4, FCGR2A, IFI16, IL8, IRAK4, LY96, LYN, PLAUR, RIPK2, STAT2, STAT3, TLR5, TNFSF14, TNFSF4, ALCAM, C9, CCR6, CEACAM6, CT45A1, CXCL3, CXCL5, CXCR1, CXCR2, DMBT1, FOXJ1, ITCH, LBP, MAP2K2, PRAME, PSMD7, and/or TNFSF18.

Embodiment 58. The method of any one of embodiments 53 to 57, wherein the one or more genes include CD68.

Embodiment 59. The method of any one of embodiments 53 to 57, wherein the one or more genes include CD163.

Embodiment 60. The method of any one of embodiments 53 to 59, wherein the adenosine pathway inhibitor is an A2A receptor (ADORA2A) antagonist.

Embodiment 61. The method of embodiment 58, wherein the ADORA2A antagonist is CPI-444.

Embodiment 62. The method of any one of embodiments 53 to 61, wherein the adenosine pathway inhibitor is a CD73 antagonist, a CD38 antagonist, a CD39 antagonist, or adenosine deaminase.

Embodiment 63. The method of embodiment 62, wherein the CD73 antagonist is an anti-CD73 antibody.

Embodiment 64. The method of any one of embodiments 53 to 63, wherein the control is a sample from a healthy subject, a sample from a non-cancerous tissue, or an average level of expression in a population.

Embodiment 65. The method of any one of embodiments 53 to 64, wherein expression of other genes is not detected.

Embodiment 66. The method of any one of embodiments 53 to 65, wherein the biological sample is selected from a blood sample, a tumor biopsy, or immune cells.

Embodiment 67. The method of embodiment 66, wherein the biological sample is a tumor biopsy.

Embodiment 68. The method of any one of embodiments 53 to 67, wherein gene expression is measured by RNA sequencing, nanopore sequencing, microarray, or hybridization-based sequencing (e.g., NanoString).

Embodiment 69. The method of any one of embodiments 53 to 68, further including determining a CD68 protein level and/or a CD163 protein level in the cancer.

Embodiment 70. The method of embodiment 69, wherein the CD68 protein level and/or the CD163 protein level is determined by immunohistochemistry.

Embodiment 71. A method for detecting a level of expression of one or more genes in a subject having or suspected of having cancer, the method including:

(a) obtaining a biological sample from the subject; and
(b) detecting the level of expression of the one or more genes in the biological sample, wherein the genes are selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA;

wherein a level of expression of the one or more genes that is lower than a control indicates that the subject is a candidate for treatment with an adenosine pathway inhibitor.

Embodiment 72. The method of embodiment 71, wherein the genes are selected from EHF, FUT7, and/or OST4.

Embodiment 73. The method of embodiment 71, wherein the genes are selected from AKT3, BMI1, CD164, CD34, CD36, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, VEGFA, APP, ATG10, BCL2, CCL15, CD24, CD46, CD59, CDH1, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, MIF, PPARG, RORA, RORC, SPA17, STAT5B, TLR3, and/or TOLLIP.

Embodiment 74. The method of any one of embodiments 71 to 73, wherein the adenosine pathway inhibitor is an A2A receptor (ADORA2A) antagonist.

Embodiment 75. The method of embodiment 74, wherein the ADORA2A antagonist is CPI-444.

Embodiment 76. The method of any one of embodiments 71 to 75, wherein the adenosine pathway inhibitor is a CD73 antagonist, a CD38 antagonist, a CD39 antagonist, or adenosine deaminase.

Embodiment 77. The method of embodiment 76, wherein the CD73 antagonist is an anti-CD73 antibody.

Embodiment 78. The method of any one of embodiments 71 to 77, wherein the control is a sample from a healthy subject, a sample from a non-cancerous tissue, or an average level of expression in a population.

Embodiment 79. The method of any one of embodiments 71 to 78, wherein expression of other genes is not detected.

Embodiment 80. The method of any one of embodiments 71 to 79, wherein the biological sample is selected from a blood sample, a tumor biopsy, or immune cells.

Embodiment 81. The method of embodiment 80, wherein the biological sample is a tumor biopsy.

Embodiment 82. The method of any one of embodiments 71 to 81, wherein gene expression is measured by RNA sequencing, nanopore sequencing, microarray, or hybridization-based sequencing (e.g., NanoString).

Embodiment 83. A method of identifying a subject for treatment with an adenosine pathway inhibitor, the subject having or suspected of having cancer, the method including:

(a) obtaining a biological sample from the subject; and
(b) detecting a level of expression of one or more genes in the biological sample, wherein the genes are selected from CD68, CD163, LBP, CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, TNFSF18 and/or TREM2;
wherein a level of expression of the one or more genes that is higher than a control indicates that the subject is a candidate for treatment with the adenosine pathway inhibitor.

Embodiment 84. The method embodiment 83, wherein the one or more genes include IL6.

Embodiment 85. The method of embodiment 83, wherein the one or more genes include IL8.

Embodiment 86. The method of embodiment 83, wherein the genes are selected from BIRC5, BST1, C4BPA, CARD11, CCL11, CDK1, CLEC5A, CXCL1, CXCL2, CXCL6, LIF, PTGS2, SAA1, SLC11A1, TNFRSF11A, TREM1, TTK, ADA, BCL6, C1R, C1S, C2, CCL20, CCL8, CD14, CEBPB, CFD, CSF1, CSF2RB, CXCR4, FCGR2A, IFI16, IL8, IRAK4, LY96, LYN, PLAUR, RIPK2, STAT2, STAT3, TLR5, TNFSF14, TNFSF4, ALCAM, C9, CCR6, CEACAM6, CT45A1, CXCL3, CXCL5, CXCR1, CXCR2, DMBT1, FOXJ1, ITCH, LBP, MAP2K2, PRAME, PSMD7, and TNFSF18.

Embodiment 87. The method of embodiment 83, wherein the genes are selected from CCL2, CCL3, CCL7, CD300E, CD93, CSF3, CXCL1, CXCL2, CXCL3, CXCL5, CXCL8, ECEL1, HAS1, IL-1β, IL8, IL23, INHBA, PADI2, PID1, PTGS2, SCL747, SERPINB2, ST6GALNAC2, and/or THBS1.

Embodiment 88. The method of embodiment 83, wherein the one or more genes include CD68.

Embodiment 89. The method of embodiment 83, wherein the one or more genes include CD163.

Embodiment 90. The method of any one of embodiments 83 to 89, further including determining a CD68 protein level and/or a CD163 protein level in the cancer.

Embodiment 91. The method of embodiment 90, wherein the CD68 protein level and/or the CD163 protein level is determined by immunohistochemistry.

Embodiment 92. A method of identifying a subject for treatment with an adenosine pathway inhibitor, the subject having or suspected of having cancer, the method including:
(a) obtaining a biological sample from the subject; and
(b) detecting a level of expression of one or more genes in the biological sample, wherein the genes are selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA;
wherein a level of expression of the one or more genes that is lower than a control indicates that the subject is a candidate for treatment with the adenosine pathway inhibitor.

Embodiment 93. The method of embodiment 92, wherein the genes are selected from EHF, FUT7, and/or OST4.

Embodiment 94. The method of embodiment 92, wherein the genes are selected from AKT3, BMI1, CD164, CD34, CD36, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, VEGFA, APP, ATG10, BCL2, CCL15, CD24, CD46, CD59, CDH1, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, MIF, PPARG, RORA, RORC, SPA17, STAT5B, TLR3, and/or TOLLIP.

Embodiment 95. The method of any one of embodiments 83 to 94, wherein the adenosine pathway inhibitor is an A2A receptor (ADORA2A) antagonist.

Embodiment 96. The method of embodiment 95, wherein the ADORA2A antagonist is CPI-444.

Embodiment 97. The method of any one of embodiments 83 to 96, wherein the adenosine pathway inhibitor is a CD73 antagonist, a CD38 antagonist, a CD39 antagonist, or adenosine deaminase.

Embodiment 98. The method of embodiment 97, wherein the CD73 antagonist is an anti-CD73 antibody.

Embodiment 99. The method of any one of embodiments 83 to 98, wherein the control is a sample from a healthy subject, a sample from a non-cancerous tissue, or an average level of expression in a population.

Embodiment 100. A method of treating a subject having cancer, the method including:
(a) obtaining a biological sample from the subject;
(b) detecting a level of expression of one or more genes in the biological sample, wherein the genes are selected from CD68, CD163, LBP, CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, TNFSF18, and/or TREM21;
wherein a level of expression of the one or more genes that is higher than a control indicates that the subject is a candidate for treatment with an adenosine pathway inhibitor; and
(c) administering to the subject an effective amount of the adenosine pathway inhibitor, thereby treating the cancer.

Embodiment 101. The method of embodiment 100, wherein the adenosine pathway inhibitor is an A2A receptor (ADORA2A) antagonist.

Embodiment 102. The method of embodiment 101, wherein the ADORA2A antagonist is CPI-444.

Embodiment 103. The method of embodiment 100, wherein the adenosine pathway inhibitor is a CD73 antagonist, a CD38 antagonist, a CD39 antagonist, or adenosine deaminase.

Embodiment 104. The method of embodiment 103, wherein the CD73 antagonist is an anti-CD73 antibody.

Embodiment 105. The method of any one of embodiments 98 to 104, wherein the one or more genes include IL6.

Embodiment 106. The method of any one of embodiments 98 to 105, wherein the one or more genes include IL8.

Embodiment 107. The method of any one of embodiments 100 to 104, wherein the genes are selected from CCL2, CCL3, CCL7, CD300E, CD93, CSF3, CXCL1, CXCL2, CXCL3, CXCL5, CXCL8, ECEL1, HAS1, IL-1β, IL8, IL23, INHBA, PADI2, PID1, PTGS2, SCL747, SERPINB2, ST6GALNAC2, and/or THBS1.

Embodiment 108. The method of any one of embodiments 100 to 104, wherein the genes are selected from BIRC5, BST1, C4BPA, CARD11, CCL11, CDK1, CLEC5A, CXCL1, CXCL2, CXCL6, LIF, PTGS2, SAA1, SLC11A1, TNFRSF11A, TREM1, TTK, ADA, BCL6, C1R, C1S, C2, CCL20, CCL8, CD14, CEBPB, CFD, CSF1, CSF2RB, CXCR4, FCGR2A, IFI16, IL8, IRAK4, LY96, LYN, PLAUR, RIPK2, STAT2, STAT3, TLR5, TNFSF14, TNFSF4, ALCAM, C9, CCR6, CEACAM6, CT45A1, CXCL3, CXCL5, CXCR1, CXCR2, DMBT1, FOXJ1, ITCH, LBP, MAP2K2, PRAME, PSMD7, and TNFSF18.

Embodiment 109. The method of any one of embodiments 100 to 104, wherein the one or more genes include CD68.

Embodiment 110. The method of any one of embodiments 100 to 104, wherein the one or more genes include CD163.

Embodiment 111. The method of any one of embodiments 100 to 110, wherein expression of other genes is not detected.

Embodiment 112. The method of any one of embodiments 100 to 109, wherein the biological sample is selected from a blood sample, a tumor biopsy, or immune cells.

Embodiment 113. The method of embodiment 112, wherein the biological sample is a tumor biopsy.

Embodiment 114. The method of any one of embodiments 100 to 113, wherein gene expression is measured by RNA sequencing, nanopore sequencing, microarray, or hybridization-based sequencing (e.g., NanoString).

Embodiment 115. The method of any one of embodiments 100 to 114, wherein the control is a sample from a healthy subject, a sample from a non-cancerous tissue, or an average level of expression in a population.

Embodiment 116. The method of any one of embodiments 100 to 115, further including determining a CD68 protein level and/or a CD163 protein level in the cancer.

Embodiment 117. The method of embodiment 116, wherein the CD68 protein level and/or the CD163 protein level is determined by immunohistochemistry.

Embodiment 118. A method of treating a subject having cancer, the method including:
(a) obtaining a biological sample from the subject;
(b) detecting a level of expression of one or more genes in the biological sample, wherein the genes are selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA, wherein a level of expression of the one or more genes that is lower than a control indicates that the subject is a candidate for treatment with an adenosine pathway inhibitor; and
(c) administering to the subject an effective amount of the adenosine pathway inhibitor, thereby treating the cancer.

Embodiment 119. The method of embodiment 118, wherein the adenosine pathway inhibitor is an A2A receptor (ADORA2A) antagonist.

Embodiment 120. The method of embodiment 119, wherein the ADORA2A antagonist is CPI-444.

Embodiment 121. The method of embodiment 100, wherein the adenosine pathway inhibitor is a CD73 antagonist, a CD38 antagonist, a CD39 antagonist, or adenosine deaminase.

Embodiment 122. The method of embodiment 100, wherein the CD73 antagonist is an anti-CD73 antibody.

Embodiment 123. The method of any one of embodiments 118 to 122, wherein the genes are selected from EHF, FUT7, and/or OST4.

Embodiment 124. The method of any one of embodiments 118 to 122, wherein the genes are selected from AKT3, BMI1, CD164, CD34, CD36, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, VEGFA, APP, ATG10, BCL2, CCL15, CD24, CD46, CD59, CDH1, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, MIF, PPARG, RORA, RORC, SPA17, STAT5B, TLR3, and/or TOLLIP.

Embodiment 125. The method of any one of embodiments 118 to 124, wherein expression of other genes is not detected.

Embodiment 126. The method of any one of embodiments 118 to 125, wherein the biological sample is selected from a blood sample, a tumor biopsy, or immune cells.

Embodiment 127. The method of embodiment 126, wherein the biological sample is a tumor biopsy.

Embodiment 128. The method of any one of embodiments 118 to 127, wherein gene expression is measured by RNA sequencing, nanopore sequencing, microarray, or hybridization-based sequencing (e.g., NanoString).

Embodiment 129. The method of any one of embodiments 118 to 128, wherein the control is a sample from a healthy subject, a sample from a non-cancerous tissue, or an average level of expression in a population.

Embodiment 130. A method of treating a subject having cancer, the method including:
(a) obtaining a biological sample from the subject;
(b) receiving an identification of a patient as having a decreased level of expression of one or more genes selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA in a biological sample, and/or an increased level of expression of one or more genes selected from CD68, CD163, LBP, CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, TNFSF18, and/or TREM21; and (c) administering to the subject an effective amount of an adenosine pathway inhibitor, thereby treating the cancer.

Embodiment 131. The method of embodiment 130, wherein the one or more genes include IL6.

Embodiment 132. The method of embodiment 130, wherein the one or more genes include IL8.

Embodiment 133. The method of embodiment 130, wherein the one or more genes include CCL20 and CX3CL1.

Embodiment 134. The method of embodiment 133, wherein the level of expression of CCL20 in the biological sample is higher than the control, and the level of expression of CX3CL1 in the biological sample is lower than the control.

Embodiment 135. The method of any one of embodiments 130 to 134, wherein the level of expression of the one or more genes was determined by RNA sequencing, nanopore sequencing, microarray, hybridization-based sequencing (e.g., NanoString).

Embodiment 136. A method of treating a subject having cancer, the method including:
(a) obtaining a biological sample from the subject;
(b) detecting a level of expression of one or more proteins in the biological sample, wherein the proteins are selected from CD68, CD163, LBP, BIRC5, BST1, CARD11, CCL2, CCL3, CCL7, CCL24, CCNE1, CD14, CD300E, CD86, CD93, CDK1, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, IL1A, IL-1B, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, C1R, C1S, C4BPA, CCL11, CCL20, CXCL16, CXCL2, HAMP, HSD11B1, ITGAM, LIF, SAA1, TFRC, TLR5, TNFRSF11A, TNFSF14, TREM1, TREM2, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, TNFSF18, APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CD36, CDH1, CDH5, CREB1, DOCK9, ENG, HMGB1, ITGA1, JAM3, MAF, MAPK3, MAPK8, MCAM, MFGE8, MIF, NOTCH1, NRP1, PRKCE, RORA, TLR3, SMAD2, TAL1, THY1, TNFSF12, TRAF6, TXNIP, VEGFA, S100A8, and/or WDR83OS; and (c) administering to the subject an effective amount of an adenosine pathway inhibitor, thereby treating the cancer.

Embodiment 137. The method of embodiment 136, wherein the adenosine pathway inhibitor is an A2A receptor (ADORA2A) antagonist.

Embodiment 138. The method of embodiment 137, wherein the ADORA2A antagonist is CPI-444.

Embodiment 139. The method of embodiment 136, wherein the adenosine pathway inhibitor is a CD73 antagonist, a CD38 antagonist, a CD39 antagonist, or adenosine deaminase.

Embodiment 140. The method of embodiment 136, wherein the adenosine pathway inhibitor is an anti-CD73 antibody.

Embodiment 141. The method of any one of embodiments 136 to 140, wherein the one or more proteins include IL6.

Embodiment 142. The method of any one of embodiments 136 to 141, wherein the one or more proteins include IL8.

Embodiment 143. The method of any one of embodiments 136 to 140, wherein the one or more proteins include CCL20 and CX3CL1.

Embodiment 144. The method of embodiment 143, wherein the level of expression of CCL20 in the biological sample is higher than the control, and the level of expression of CX3CL1 in the biological sample is lower than the control.

Embodiment 145. The method of any one of embodiments 136 to 140, wherein the proteins are selected from CCL2, CCL3, CCL7, CD300E, CD93, CSF3, CXCL1, CXCL2, CXCL3, CXCL5, CXCL8, ECEL1, HAS1, IL-1β, IL8, IL23, INHBA, PADI2, PID1, PTGS2, SCL747, SERPINB2, ST6GALNAC2, and/or THBS1.

Embodiment 146. The method of embodiment 141, wherein the proteins are selected from CXCL1, CXCL2, CXCL3, CXCL5, SERPINB2, IL8, and/or IL-1β.

Embodiment 147. The method of any one of embodiments 136 to 140, wherein the proteins are selected from CCL24, CCNE1, EHF, FUT7, GALM, GBP6, IL5, LAP3, MRPL11, OST4, WDR83OS, and/or TBX21.

Embodiment 148. The method of embodiment 147, wherein the proteins are selected from EHF, FUT7, and/or OST4.

Embodiment 149. The method of any one of embodiments 136 to 140, wherein the proteins are selected from BIRC5, BST1, C4BPA, CARD11, CCL11, CDK1, CLEC5A, CXCL1, CXCL2, CXCL6, LIF, PTGS2, SAA1, SLC11A1, TNFRSF11A, TREM1, TTK, ADA, BCL6, C1R, C1S, C2, CCL20, CCL8, CD14, CEBPB, CFD, CSF1, CSF2RB, CXCR4, FCGR2A, IFI16, IL8, IRAK4, LY96, LYN, PLAUR, RIPK2, STAT2, STAT3, TLR5, TNFSF14, TNFSF4, ALCAM, C9, CCR6, CEACAM6, CT45A1, CXCL3, CXCL5, CXCR1, CXCR2, DMBT1, FOXJ1, ITCH, LBP, MAP2K2, PRAME, PSMD7, and/or TNFSF18.

Embodiment 150. The method of any one of embodiments 136 to 140, wherein the proteins are selected from AKT3, BMI1, CD164, CD34, CD36, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, VEGFA, APP, ATG10, BCL2, CCL15, CD24, CD46, CD59, CDH1, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, MIF, PPARG, RORA, RORC, SPA17, STAT5B, TLR3, and/or TOLLIP.

Embodiment 151. The method of any one of embodiments 136 to 140, wherein the one or more proteins include CD68.

Embodiment 152. The method of any one of embodiments 136 to 140, wherein the one or more proteins include CD163.

Embodiment 153. The method of any one of embodiments 136 to 152, wherein expression of other proteins is not detected.

Embodiment 154. The method of any one of embodiments 136 to 153, wherein the biological sample is selected from a blood sample, a tumor biopsy, immune cells.

Embodiment 155. The method of embodiment 154, wherein the biological sample is a tumor biopsy.

Embodiment 156. The method of embodiment 154, wherein the biological sample is a blood sample.

Embodiment 157. The method of any one of embodiments 136 to 156, wherein protein expression is measured by ELISA.

Embodiment 158. The method of any one of embodiments 136 to 156, wherein protein expression is measured by immunohistochemistry.

Embodiment 159. A method for detecting a level of expression of one or more proteins in a subject having or suspected of having cancer, the method including:
(a) obtaining a biological sample from the subject; and
(b) detecting the level of expression of the one or more proteins in the biological sample, wherein the proteins are selected from CD68, CD163, LBP, CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1B, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, TNFSF18, and/or TREM2;
wherein a level of expression of the one or more proteins that is higher than a control indicates that the subject is a candidate for treatment with an adenosine pathway inhibitor.

Embodiment 160. The method of embodiment 159, wherein the one or more proteins include IL6.

Embodiment 161. The method of embodiment 159, wherein the one or more proteins include IL8.

Embodiment 162. The method of embodiment 159, wherein the proteins are selected from CCL2, CCL3, CCL7, CD300E, CD93, CSF3, CXCL1, CXCL2, CXCL3, CXCL5, CXCL8, ECEL1, HAS1, IL-1β, IL8, IL23, INHBA, PADI2, PID1, PTGS2, SCL747, SERPINB2, ST6GALNAC2, and/or THBS1.

Embodiment 163. The method of embodiment 159, wherein the proteins are selected from BIRC5, BST1, C4BPA, CARD11, CCL11, CDK1, CLEC5A, CXCL1, CXCL2, CXCL6, LIF, PTGS2, SAA1, SLC11A1, TNFRSF11A, TREM1, TTK, ADA, BCL6, C1R, C1S, C2, CCL20, CCL8, CD14, CEBPB, CFD, CSF1, CSF2RB, CXCR4, FCGR2A, IFI16, IL8, IRAK4, LY96, LYN, PLAUR, RIPK2, STAT2, STAT3, TLR5, TNFSF14, TNFSF4, ALCAM, C9, CCR6, CEACAM6, CT45A1, CXCL3, CXCL5, CXCR1, CXCR2, DMBT1, FOXJ1, ITCH, LBP, MAP2K2, PRAME, PSMD7, and/or TNFSF18.

Embodiment 164. The method of embodiment 159, wherein the one or more proteins include CD68.

Embodiment 165. The method of embodiment 159, wherein the one or more proteins include CD163.

Embodiment 166. A method for detecting a level of expression of one or more proteins in a subject having or suspected of having cancer, the method including:
(a) obtaining a biological sample from the subject; and
(b) detecting the level of expression of the one or more proteins in the biological sample, wherein the proteins are selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA;
wherein a level of expression of the one or more proteins that is lower than a control indicates that the subject is a candidate for treatment with an adenosine pathway inhibitor.

Embodiment 167. The method of embodiment 166, wherein the proteins are selected from EHF, FUT7, and/or OST4.

Embodiment 168. The method of embodiment 166, wherein the proteins are selected from AKT3, BMI1, CD164, CD34, CD36, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, VEGFA, APP, ATG10, BCL2, CCL15, CD24, CD46, CD59, CDH1, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, MIF, PPARG, RORA, RORC, SPA17, STAT5B, TLR3, and/or TOLLIP.

Embodiment 169. A method of identifying a subject for treatment with an adenosine pathway inhibitor, the subject having or suspected of having cancer, the method including:
(a) obtaining a biological sample from the subject; and
(b) detecting a level of expression of one or more proteins in the biological sample, wherein the proteins are selected from CD68, CD163, LBP, CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1B, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, TNFSF18, and/or TREM2;

wherein a level of expression of the one or more proteins that is higher than a control indicates that the subject is a candidate for treatment with the adenosine pathway inhibitor.

Embodiment 170. The method of embodiment 169, wherein the one or more proteins include IL6.

Embodiment 171. The method of embodiment 169, wherein the one or more proteins include IL8.

Embodiment 172. The method of embodiment 169, wherein the proteins are selected from BIRC5, BST1, C4BPA, CARD11, CCL11, CDK1, CLEC5A, CXCL1, CXCL2, CXCL6, LIF, PTGS2, SAA1, SLC11A1, TNFRSF11A, TREM1, TTK, ADA, BCL6, C1R, C1S, C2, CCL20, CCL8, CD14, CEBPB, CFD, CSF1, CSF2RB, CXCR4, FCGR2A, IFI16, IL8, IRAK4, LY96, LYN, PLAUR, RIPK2, STAT2, STAT3, TLR5, TNFSF14, TNFSF4, ALCAM, C9, CCR6, CEACAM6, CT45A1, CXCL3, CXCL5, CXCR1, CXCR2, DMBT1, FOXJ1, ITCH, LBP, MAP2K2, PRAME, PSMD7, and/or TNFSF18.

Embodiment 173. The method of embodiment 169, wherein the one or more proteins include CD68.

Embodiment 174. The method of embodiment 169, wherein the one or more proteins include CD163.

Embodiment 175. A method of identifying a subject for treatment with an adenosine pathway inhibitor, the subject having or suspected of having cancer, the method including:
(a) obtaining a biological sample from the subject; and
(b) detecting a level of expression of one or more proteins in the biological sample, wherein the proteins are selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA;
wherein a level of expression of the one or more proteins that is lower than a control indicates that the subject is a candidate for treatment with the adenosine pathway inhibitor.

Embodiment 176. The method of embodiment 175, wherein the proteins are selected from AKT3, BMI1, CD164, CD34, CD36, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, VEGFA, APP, ATG10, BCL2, CCL15, CD24, CD46, CD59, CDH1, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, MIF, PPARG, RORA, RORC, SPA17, STAT5B, TLR3, and/or TOLLIP.

Embodiment 177. A method of treating a subject having cancer, the method including:
(a) obtaining a biological sample from the subject;
(b) detecting a level of expression of one or more proteins in the biological sample, wherein the proteins are selected from CD68, CD163, LBP, CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1B, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, TNFSF18, and/or TREM2, wherein a level of expression of the one or more proteins that is higher than a control indicates that the subject is a candidate for treatment with an adenosine pathway inhibitor; and
(c) administering to the subject an effective amount of the adenosine pathway inhibitor, thereby treating the cancer.

Embodiment 178. The method of embodiment 177, wherein the one or more proteins include IL6.

Embodiment 179. The method of embodiment 177, wherein the one or more proteins include IL8.

Embodiment 180. The method of embodiment 177, wherein the proteins are selected from CCL2, CCL3, CCL7, CD300E, CD93, CSF3, CXCL1, CXCL2, CXCL3, CXCL5, CXCL8, ECEL1, HAS1, IL-1β, IL8, IL23, INHBA, PADI2, PID1, PTGS2, SCL747, SERPINB2, ST6GALNAC2, and/or THBS1.

Embodiment 181. The method of embodiment 177, wherein the proteins are selected from BIRC5, BST1, C4BPA, CARD11, CCL11, CDK1, CLEC5A, CXCL1, CXCL2, CXCL6, LIF, PTGS2, SAA1, SLC11A1, TNFRSF11A, TREM1, TTK, ADA, BCL6, C1R, C1S, C2, CCL20, CCL8, CD14, CEBPB, CFD, CSF1, CSF2RB, CXCR4, FCGR2A, IFI16, IL8, IRAK4, LY96, LYN, PLAUR, RIPK2, STAT2, STAT3, TLR5, TNFSF14, TNFSF4, ALCAM, C9, CCR6, CEACAM6, CT45A1, CXCL3, CXCL5, CXCR1, CXCR2, DMBT1, FOXJ1, ITCH, LBP, MAP2K2, PRAME, PSMD7, and/or TNFSF18.

Embodiment 182. The method of embodiment 177, wherein the one or more proteins include CD68.

Embodiment 183. The method of embodiment 177, wherein the one or more proteins include CD163.

Embodiment 184. A method of treating a subject having cancer, the method including:
(a) obtaining a biological sample from the subject;
(b) detecting a level of expression of one or more proteins in the biological sample, wherein the proteins are selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, CD36, CDH1, MIF, RORA, TLR3, and/or VEGFA, wherein a level of expression of the one or more proteins that is lower than a control indicates that the subject is a candidate for treatment with an adenosine pathway inhibitor; and
(c) administering to the subject an effective amount of the adenosine pathway inhibitor, thereby treating the cancer.

Embodiment 185. The method of embodiment 184, wherein the proteins are selected from EHF, FUT7, and/or OST4.

Embodiment 186. The method of embodiment 184, wherein the proteins are selected from AKT3, BMI1, CD164, CD34, CD36, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, VEGFA, APP, ATG10, BCL2, CCL15, CD24, CD46, CD59, CDH1, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, MIF, PPARG, RORA, RORC, SPA17, STAT5B, TLR3, and/or TOLLIP.

Embodiment 187. A method of treating a subject having cancer, the method including:
(a) obtaining a biological sample from the subject;
(b) receiving an identification of a patient as having a decreased level of expression of one or more proteins selected from CCL24, CCNE1, EHF, FUT7, GALM, GBP6, IL5, LAP3, MRPL11, OST4, WDR83OS, TBX21; APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12,
TRAF6, TXNIP, CD36, CDH1, MIF, RORA, TLR3, and/or VEGFA, and/or an increased level of expression of one or more proteins selected from CD68, CD163, LBP, CCL2, CCL3, CCL7, CD14, CD300E, CD86, CD93, CLEC5A, CSF3, CXCL1, CXCL2, CXCL3, CXCL5, CXCL6, CXCL8, DFNA5, ECEL1, EPB41L3, GPR157, HAS1, IL1A, IL-1β, IL23, IL24, IL6, IL8, INHBA, LAYN, LOC100505585, NID1, PADI2, PID1, PLAUR, PPBP, PTGS2, RHCG, SERPINB2, SLC11A1, SLC7A7, SPON1, ST6GALNAC2, THBS1, C1R, C1S, C4BPA, CCL11, CCL20, CXCL16, HAMP, HSD11B1, ITGAM, LIF, S100A8, SAA1, TFRC, TLR5, TNFSF14, BIRC5, BST1, CARD11, CDK1, TNFRSF11A, TREM1, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, MAP2K2, PRAME, PSMD7, TNFSF18, and/or TREM21, in a biological sample; and
(c) administering to the subject an effective amount of an adenosine pathway inhibitor, thereby treating the cancer.

Embodiment 188. The method of embodiment 187, wherein the one or more proteins include IL6.

Embodiment 189. The method of embodiment 187, wherein the one or more proteins include IL8.

Embodiment 190. The method of embodiment 187, wherein the level of expression of CCL20 is higher than the control, and the level of expression of CX3CL1 is lower than the control.

Embodiment 191. The method of embodiment 187, wherein the one or more proteins include CD68.

Embodiment 192. The method of embodiment 187, wherein the one or more proteins include CD163.

Embodiment 193. The method of any one of embodiments 159 to 192, wherein expression of other proteins is not detected.

Embodiment 194. The method of any one of embodiments 159 to 193, wherein the biological sample is selected from a blood sample, a tumor biopsy, immune cells.

Embodiment 195. The method of embodiment 194, wherein the biological sample is a tumor biopsy.

Embodiment 196. The method of embodiment 194, wherein the biological sample is a blood sample.

Embodiment 197. The method of any one of embodiments 159 to 196, wherein protein expression is measured by ELISA.

Embodiment 198. The method of any one of embodiments 159 to 196, wherein protein expression is measured by immunohistochemistry.

Embodiment 199. The method of any one of embodiments 159 to 198, wherein the control is a sample from a healthy subject, a sample from a non-cancerous tissue, an average level of expression in a population.

Embodiment 200. The method of 159 to 199, wherein the adenosine pathway inhibitor is an A2A receptor (ADORA2A) antagonist.

Embodiment 201. The method of embodiment 200, wherein the ADORA2A antagonist is CPI-444.

Embodiment 202. The method of any one of embodiments 159 to 201, wherein the adenosine pathway inhibitor is a CD73 antagonist, a CD38 antagonist, a CD39 antagonist, or adenosine deaminase.

Embodiment 203. The method of embodiment 202, wherein the CD73 antagonist is an anti-CD73 antibody.

Embodiment 204. A kit for determining a level of gene expression in a biological sample, the kit including:
(i) a primer for one or more genes selected from CD68, CD163, LBP, CCL2, CCL3, CCL7, CCL24, CCNE1, CD14, CD300E, CD86, CD93, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, IL1A, IL-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, C1R, C1S, C4BPA, CCL11, CCL20, CXCL16, CXCL2, HAMP, HSD11B1, ITGAM, LIF, SAA1, TFRC, TLR5, TNFSF14, TREM2, APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CDH5, CREB1, DOCK9, ENG, HMGB1, ITGA1, JAM3, MAF, MAPK3, MAPK8, MCAM, MFGE8, NOTCH1, NRP1, PRKCE, SMAD2, TAL1, THY1, TNFSF12, TRAF6, TXNIP, VEGFA, and/or WDR83OS; and
(ii) a reagent for processing of the biological sample.

Embodiment 205. The kit of embodiment 204, wherein the reagent for processing of the biological sample is a reagent for preparing cDNA from the biological sample.

Embodiment 206. The kit of embodiment 204 or 205, further including one or more reagents for RNA sequencing.

Embodiment 207. The kit of any one of embodiments 204 to 206, further including a microarray configured for sequencing of the one or more genes.

Embodiment 208. The kit of any one of embodiments 204 to 207, further a including reagent for quantitative PCR of the one or more genes.

Embodiment 209. The kit of any one of embodiments 204 to 208, further including a reagent for RNA-seq.

Embodiment 210. The kit of any one of embodiments 204 to 209, further including instructions for determining the level of gene expression in the biological sample.

Embodiment 211. The kit of any one of embodiments 204 to 210, wherein the biological sample is selected from a blood sample, a tumor biopsy, and immune cells.

Embodiment 212. The kit of any one of embodiments 204 to 211, further including an anti-CD68 and/or anti-CD163 antibody.

Embodiment 213. A method for detecting a level of expression of CD68 and/or CD163 in a subject having or suspected of having cancer, the method including:
  a) obtaining a biological sample from the subject; and
  b) detecting the level of expression of CD68 and/or CD163 in the biological sample.

Embodiment 214. The method of embodiment 213, wherein a level of CD68 protein is detected.

Embodiment 215. The method of embodiment 213, wherein a level of CD68 gene expression is detected.

Embodiment 216. The method of embodiment 213, wherein a level of CD163 protein is detected.

Embodiment 217. The method of embodiment 213, wherein a level of CD163 gene expression is detected.

Embodiment 218. The method of embodiment 214 or 216, wherein the protein level is detected using immunohistochemistry.

Embodiment 219. The method of any one of embodiments 213 to 218, further including detecting a level of expression of one or more additional genes in the sample.

Embodiment 220. The method of embodiment 219, wherein the one or more additional genes are selected from CD68, CD163, BIRC5, BST1, CARD11, CCL2, CCL3, CCL7, CCL24, CCNE1, CD14, CD300E, CD86, CD93, CDK1, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, IL1A, IL-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, C1R, C1S, C4BPA, CCL11, CCL20, CXCL16, CXCL2, HAMP, HSD11B1, ITGAM, LIF, SAA1, TFRC, TLR5, TNFRSF11A, TNFSF14, TREM1, TREM2, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, LBP, MAP2K2, PRAME, PSMD7, TNFSF18, APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CD36, CDH1, CDH5, CREB1, DOCK9, ENG, HMGB1, ITGA1, JAM3, MAF, MAPK3, MAPK8, MCAM, MFGE8, MIF, NOTCH1, NRP1, PRKCE, RORA, TLR3, SMAD2, TAL1, THY1, TNFSF12, TRAF6, TXNIP, VEGFA, S100A8, and/or WDR83OS.

Embodiment 221. The method of any one of embodiments 213 to 217, further including detecting a level of expression of one or more additional proteins in the sample.

Embodiment 222. The method of embodiment 221, wherein the one or more additional proteins are selected from CD68, CD163, BIRC5, BST1, CARD11, CCL2, CCL3, CCL7, CCL24, CCNE1, CD14, CD300E, CD86, CD93, CDK1, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, IL1A, IL-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, C1R, C1S, C4BPA, CCL11, CCL20, CXCL16, CXCL2, HAMP, HSD11B1, ITGAM, LIF, SAA1, TFRC, TLR5, TNFRSF11A, TNFSF14, TREM1, TREM2, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, LBP, MAP2K2, PRAME, PSMD7, TNFSF18, APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CD36, CDH1, CDH5, CREB1, DOCK9, ENG, HMGB1, ITGA1, JAM3, MAF, MAPK3, MAPK8, MCAM, MFGE8, MIF, NOTCH1, NRP1, PRKCE, RORA, TLR3, SMAD2, TAL1, THY1, TNFSF12, TRAF6, TXNIP, VEGFA, S100A8, and/or WDR83OS.

Embodiment 223. The method of any one of embodiments 213 to 222, wherein CD68 expression in the biological sample is higher than a control.

Embodiment 224. The method of any one of embodiments 213 to 222, wherein CD163 expression in the biological sample is higher than a control.

Embodiment 225. The method of any one of embodiments 213 to 224, wherein expression of other genes or proteins is not detected.

Embodiment 226. The method of any one of embodiments 213 to 225, wherein the biological sample is selected from a blood sample, a tumor biopsy, or immune cells.

Embodiment 227. The method of embodiment 226, wherein the biological sample is a tumor biopsy.

Embodiment 228. The method of any one of embodiments 213 to 227, wherein gene expression is measured by RNA sequencing, nanopore sequencing, microarray, or hybridization-based sequencing (e.g., NanoString).

Embodiment 229. The method of any one of embodiments 213 to 228, further including:
  (c) comparing the level of expression of CD68 and/or CD163 in the sample to a level of expression of CD68 and/or CD163 in a suitable control.

Embodiment 230. The method of embodiment 229, wherein the suitable control is a sample from a healthy subject, a sample from a non-cancerous tissue, or an average level of expression in a population.

Embodiment 231. A method treating a subject having cancer, the method including:
  (a) obtaining a biological sample from the subject;
  (b) detecting a level of expression of CD68 and/or CD163 in the biological sample; and
  (c) administering to the subject an effective amount of an adenosine pathway inhibitor, thereby treating the cancer.

Embodiment 232. The method of embodiment 231, wherein the adenosine pathway inhibitor is an A2A receptor (ADORA2A) antagonist.

Embodiment 233. The method of embodiment 232, wherein the ADORA2A antagonist is CPI-444.

Embodiment 234. The method of embodiment 231, wherein the adenosine pathway inhibitor is is a CD73 antagonist, a CD38 antagonist, a CD39 antagonist, or adenosine deaminase.

Embodiment 235. The method of embodiment 234, wherein the CD73 antagonist is an anti-CD73 antibody.

Embodiment 236. The method of any one of embodiments 231 to 235, further including administering a CXCR2 inhibitor to the subject.

Embodiment 237. The method of embodiment 236, wherein the CXCR2 inhibitor is selected from AZD5069, anti-CXCR2 antibody, and Navarixin.

Embodiment 238. The method of any one of embodiments 231 to 237, wherein a level of CD68 protein is detected.

Embodiment 239. The method of any one of embodiments 231 to 237, wherein a level of CD68 gene expression is detected.

Embodiment 240. The method of any one of embodiments 231 to 237, wherein a level of CD163 protein is detected.

Embodiment 241. The method of any one of embodiments 231 to 237, wherein a level of CD163 gene expression is detected.

Embodiment 242. The method of embodiment 238 or 240, wherein the protein level is detected using immunohistochemistry.

Embodiment 243. The method of any one of embodiments 231 to 242, further including detecting a level of expression of one or more additional genes in the sample.

Embodiment 244. The method of embodiment 243, wherein the one or more additional genes are selected from CD68, CD163, BIRC5, BST1, CARD11, CCL2, CCL3, CCL7, CCL24, CCNE1, CD14, CD300E, CD86, CD93, CDK1, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, IL1A, IL-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, C1R, C1S, C4BPA, CCL11, CCL20, CXCL16, CXCL2, HAMP, HSD11B1, ITGAM, LIF, SAA1, TFRC, TLR5, TNFRSF11A, TNFSF14, TREM1, TREM2, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, LBP, MAP2K2, PRAME, PSMD7, TNFSF18, APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CD36, CDH1, CDH5, CREB1, DOCK9, ENG, HMGB1, ITGA1, JAM3, MAF, MAPK3, MAPK8, MCAM, MFGE8, MIF, NOTCH1, NRP1, PRKCE, RORA, TLR3, SMAD2, TAL1, THY1, TNFSF12, TRAF6, TXNIP, VEGFA, S100A8, and/or WDR83OS.

Embodiment 245. The method of any one of embodiments 231 to 244, further including detecting a level of expression of one or more additional proteins in the sample.

Embodiment 246. The method of embodiment 245, wherein the one or more additional proteins are selected from CD68, CD163, BIRC5, BST1, CARD11, CCL2, CCL3, CCL7, CCL24, CCNE1, CD14, CD300E, CD86, CD93, CDK1, CLEC5A, CSF3, CXCL1, CXCL2, CXCL3, CXCL5, CXCL6, CXCL8, DFNA5, ECEL1, EPB41L3, EHF, FUT7, GALM, GBP6, GPR157, HAS1, IL1A, IL-1β, IL23, IL24, IL5, IL6, IL8, INHBA, LAP3, LAYN, LOC100505585, MRPL11, NID1, OST4, PADI2, PID1, PLAUR, PPBP, PTGS2, RHCG, SERPINB2, SLC11A1, SLC7A7, SPON1, ST6GALNAC2, TBX21, THBS1, C1R, C1S, C4BPA, CCL11, CCL20, CXCL16, CXCL2, HAMP, HSD11B1, ITGAM, LIF, SAA1, TFRC, TLR5, TNFRSF11A, TNFSF14, TREM1, TREM2, TTK, ADA, BCL6, C2, CCL8, CEBPB, CFD, CSF1, CSF2RB, CXCR4, FCGR2A, IFI16, IRAK4, LY96, LYN, RIPK2, STAT2, STAT3, TNFSF4, ALCAM, C9, CCR6, CEACAM6, CT45A1, CXCR1, CXCR2, DMBT1, FOXJ1, ITCH, LBP, MAP2K2, PRAME, PSMD7, TNFSF18, APP, ATG10, BCL2, CCL15, CD24, CD46, CD59, CREB5, CX3CL1, CXCL14, CYFIP2, DEFB1, DPP4, ECSIT, EPCAM, IFIT1, IGF1R, ITGA6, ITGB3, MAP2K4, MAPK1, MASP1, PPARG, RORC, SPA17, STAT5B, TOLLIP, AKT3, BMI1, CD164, CD34, CD36, CDH1, CDH5, CREB1, DOCK9, ENG, HMGB1, ITGA1, JAM3, MAF, MAPK3, MAPK8, MCAM, MFGE8, MIF, NOTCH1, NRP1, PRKCE, RORA, TLR3, SMAD2, TAL1, THY1, TNFSF12, TRAF6, TXNIP, VEGFA, S100A8, and/or WDR83OS.

Embodiment 247. The method of any one of embodiments 231 to 246, wherein expression of other genes or proteins is not detected.

Embodiment 248. The method of any one of embodiments 231 to 247, wherein the biological sample is selected from a blood sample, a tumor biopsy, or immune cells.

Embodiment 249. The method of embodiment 248, wherein the biological sample is a tumor biopsy.

Embodiment 250. The method of any one of embodiments 231 to 249, wherein gene expression is measured by RNA sequencing, nanopore sequencing, microarray, or hybridization-based sequencing (e.g., NanoString).

Embodiment 251. The method of any one of embodiments 231 to 250, further including:
(c) comparing the level of expression of CD68 and/or CD163 in the sample to a level of expression of CD68 and/or CD163 in a suitable control.

Embodiment 252. The method of embodiment 251, wherein the suitable control is a sample from a healthy subject, a sample from a non-cancerous tissue, or an average level of expression in a population.

Embodiment 253. A method of identifying a subject for treatment with an adenosine pathway inhibitor, the subject having or suspected of having cancer, the method including:
(a) obtaining a biological sample from the subject; and
(b) detecting a level of expression of CD68 and/or CD163;
wherein a level of expression of CD68 and/or CD163 that is higher than a suitable control indicates that the subject is a candidate for treatment with the adenosine pathway inhibitor.

Embodiment 254. The method of embodiment 253, wherein the suitable control is a sample from a healthy subject, a sample from a non-cancerous tissue, or an average level of expression in a population.

Embodiment 255. The method of embodiment 253 or 254 wherein a level of CD68 protein is detected.

Embodiment 256. The method of embodiment 253 or 254, wherein a level of CD68 gene expression is detected.

Embodiment 257. The method of embodiment 253 or 254, wherein a level of CD163 protein is detected.

Embodiment 258. The method of embodiment 253 or 254, wherein a level of CD163 gene expression is detected.

Embodiment 259. A method for detecting a level of expression of one or more genes in a subject having or suspected of having cancer, the method including:
(a) obtaining a biological sample from the subject; and
(b) detecting the level of expression of one or more genes selected from ACTBL2, ADAM8, ALOX5AP, ANXA2P2, AQP9, AREG, ARHGAP9, BCL2A1, BCL3, BDKRB2, BIRC3, C10orf55, C15orf48, C19orf59, C1orf38, C1R, C1S, C3, C5AR1, C8orf4, CASP4, CCL18, CCL2, CCL20, CCL3, CCL3L1, CCL4, CCL4L2, CCL7, CCL8, CCR1, CD14, CD300A, CD300E, CD300LB, CD53, CD69, CD86, CDCP1, CEACAM3, CFB, CLEC4A, CLEC4D, CLEC4E, CLEC5A, CLEC7A, CSF2, CSF2RB, CSF3, CSF3R, CXCL1, CXCL2, CXCL3, CXCL5, CXCL6, CXCR1, CXCR2, CXorf21, CYR61, CYTH4, CYTIP, DAPP1, DUSP1, DUSP5, EGR3, EMP1, EMR2, EMR3, EREG, F3, FCAR, FCER1G, FCGR2A, FCGR2B, FCGR3B, FFAR2, FGR, FOS, FOSL1, FPR1, FPR2, GOS2, GLIPR1, GNA15, GPR109A, GPR109B, GPR183, GPR84, GPR97, GPRC5A, HAS1, HBEGF, HCK, HK3, ICAM1, IER3, IL10, IL1A, IL1B, IL1R2, IL1RL1, IL1RN, IL4R, IL6, IL7R, IL8, JUNB, KLF6, LAMC2, LCP2, LIF, LILRA5, LILRA6, LILRB2, LILRB3, LRG1, LYN, MAFF, MAP3K8, MCL1, MEFV, MMP1, MMP12, MMP3, MMP7, MNDA, MYO1G, NAMPT, NCF2, NCF4, NCOA7, NFE2, NFKBIZ, NLRP3, NNMT, OBFC2A, OSM, OSMR, P2RY6, PF4V1, PHLDA1, PI3, PLAU, PLAUR, PLEK, PLK3, PPBP, PPP1R15A, PRDM1, PTGS2, PTPN22, RARRES1, RASGRP4, RGS1, RGS2, RND1, RND3, S100A12, S100A8, S100A9, SAA1, SAA2, SAA4, SAMSN1, SAT1, SELE, SERPINA1, SERPINB2, SERPINB4, SERPINB7, SERPINB8, SERPINE1, SLC11A1, SLC2A14, SLC2A3, SNAI1, SOCS3, SOD2, SPI1, SRGN, STX11, TDO2, TGM2, THBS1, TLR2, TNF, TNFAIP2, TNFAIP3, TNFAIP6, TNIP3, TREM1, VNN1, VNN2, VNN3, ZC3H12A, ZFP36 in the biological sample.

Embodiment 260. The method of Embodiment 259, further including:
(c) comparing the level of expression of the one or more genes in the sample to a level of expression of the one or more genes in a suitable control Embodiment 261. The method of Embodiment 260, wherein the suitable control is a sample from a healthy subject, a sample from a non-cancerous tissue, or an average level of expression in a population.

Embodiment 262. A method treating a subject having cancer, the method including:
(a) obtaining a biological sample from the subject;
(b) detecting a level of expression of one or more genes selected from ACTBL2, ADAM8, ALOX5AP, ANXA2P2, AQP9, AREG, ARHGAP9, BCL2A1, BCL3, BDKRB2, BIRC3, C10orf55, C15orf48, C19orf59, C1orf38, C1R, C1S, C3, C5AR1, C8orf4, CASP4, CCL18, CCL2, CCL20, CCL3, CCL3L1, CCL4, CCL4L2, CCL7, CCL8, CCR1, CD14, CD300A, CD300E, CD300LB, CD53, CD69, CD86, CDCP1, CEACAM3, CFB, CLEC4A, CLEC4D, CLEC4E, CLEC5A, CLEC7A, CSF2, CSF2RB, CSF3, CSF3R, CXCL1, CXCL2, CXCL3, CXCL5, CXCL6, CXCR1, CXCR2, CXorf21, CYR61, CYTH4, CYTIP, DAPP1, DUSP1, DUSP5, EGR3, EMP1, EMR2, EMR3, EREG, F3, FCAR, FCER1G, FCGR2A, FCGR2B, FCGR3B, FFAR2, FGR, FOS, FOSL1, FPR1, FPR2, GOS2, GLIPR1, GNA15, GPR109A, GPR109B, GPR183, GPR84, GPR97, GPRC5A, HAS1, HBEGF, HCK, HK3, ICAM1, IER3, IL10, IL1A, IL1B, IL1R2, IL1RL1, IL1RN, IL4R, IL6, IL7R, IL8, JUNB, KLF6, LAMC2, LCP2, LIF, LILRA5, LILRA6, LILRB2, LILRB3, LRG1, LYN, MAFF, MAP3K8, MCL1, MEFV, MMP1, MMP12, MMP3, MMP7, MNDA, MYO1G, NAMPT, NCF2, NCF4, NCOA7, NFE2, NFKBIZ, NLRP3, NNMT, OBFC2A, OSM, OSMR, P2RY6, PF4V1, PHLDA1, PI3, PLAU, PLAUR, PLEK, PLK3, PPBP, PPP1R15A, PRDM1, PTGS2, PTPN22, RARRES1, RASGRP4, RGS1, RGS2, RND1, RND3, S100A12, S100A8, S100A9, SAA1, SAA2, SAA4, SAMSN1, SAT1, SELE, SERPINA1, SERPINB2, SERPINB4, SERPINB7, SERPINB8, SERPINE1, SLC11A1, SLC2A14, SLC2A3, SNAI1, SOCS3, SOD2, SPI1, SRGN, STX11, TDO2, TGM2, THBS1, TLR2, TNF, TNFAIP2, TNFAIP3, TNFAIP6, TNIP3, TREM1, VNN1, VNN2, VNN3, ZC3H12A, and/or ZFP36 in the biological sample; and
(c) administering to the subject an effective amount of an adenosine pathway inhibitor, thereby treating the cancer.

Embodiment 263. The method of embodiment 286, wherein the adenosine pathway inhibitor is an A2A receptor (ADORA2A) antagonist.

Embodiment 264. The method of embodiment 287, wherein the ADORA2A antagonist is CPI-444.

Embodiment 265. The method of embodiment 287, wherein the adenosine pathway inhibitor is is a CD73 antagonist, a CD38 antagonist, a CD39 antagonist, or adenosine deaminase.

Embodiment 266. The method of embodiment 289, wherein the CD73 antagonist is an anti-CD73 antibody.

Embodiment 267. The method of any one of embodiments 286 to 290, further including administering a CXCR2 inhibitor to the subject.

Embodiment 268. The method of embodiment 291, wherein the CXCR2 inhibitor is selected from AZD5069, anti-CXCR2 antibody, and Navarixin.

Embodiment 269. The method of any one of embodiments 286 to 292, further including:
(d) comparing the level of expression of the one or more genes in the sample to a level of expression of the one or more genes in a suitable control.

Embodiment 270. The method of embodiment 293, wherein the suitable control is a sample from a healthy subject, a sample from a non-cancerous tissue, or an average level of expression in a population.

Embodiment 271. A method of identifying a subject for treatment with an adenosine pathway inhibitor, the subject having or suspected of having cancer, the method including:
(a) obtaining a biological sample from the subject; and
(b) detecting a level of expression of one or more genes selected from ACTBL2, ADAM8, ALOX5AP, ANXA2P2, AQP9, AREG, ARHGAP9, BCL2A1, BCL3, BDKRB2, BIRC3, C10orf55, C15orf48, C19orf59, C1orf38, C1R, C1S, C3, C5AR1, C8orf4, CASP4, CCL18, CCL2, CCL20, CCL3, CCL3L1, CCL4, CCL4L2, CCL7, CCL8, CCR1, CD14, CD300A, CD300E, CD300LB, CD53, CD69, CD86, CDCP1, CEACAM3, CFB, CLEC4A, CLEC4D, CLEC4E, CLEC5A, CLEC7A, CSF2, CSF2RB, CSF3, CSF3R, CXCL1, CXCL2, CXCL3, CXCL5, CXCL6, CXCR1, CXCR2, CXorf21, CYR61, CYTH4, CYTIP, DAPP1, DUSP1, DUSP5, EGR3, EMP1, EMR2, EMR3, EREG, F3, FCAR, FCER1G, FCGR2A, FCGR2B, FCGR3B, FFAR2, FGR, FOS, FOSL1, FPR1, FPR2, GOS2, GLIPR1, GNA15, GPR109A, GPR109B, GPR183, GPR84, GPR97, GPRC5A, HAS1, HBEGF, HCK, HK3, ICAM1, IER3, IL10, IL1A, IL1B, IL1R2, IL1RL1, IL1RN, IL4R, IL6, IL7R, IL8, JUNB, KLF6, LAMC2, LCP2, LIF, LILRA5, LILRA6, LILRB2, LILRB3, LRG1, LYN, MAFF, MAP3K8, MCL1, MEFV, MMP1, MMP12, MMP3, MMP7, MNDA, MYO1G, NAMPT, NCF2, NCF4, NCOA7, NFE2, NFKBIZ, NLRP3, NNMT, OBFC2A, OSM, OSMR, P2RY6, PF4V1, PHLDA1, PI3, PLAU, PLAUR, PLEK, PLK3, PPBP, PPP1R15A, PRDM1, PTGS2, PTPN22, RARRES1, RASGRP4, RGS1, RGS2, RND1, RND3, S100A12, S100A8, S100A9, SAA1, SAA2, SAA4, SAMSN1, SAT1, SELE, SERPINA1, SERPINB2, SERPINB4, SERPINB7, SERPINB8, SERPINE1, SLC11A1, SLC2A14, SLC2A3, SNAI1, SOCS3, SOD2, SPI1, SRGN, STX11, TDO2, TGM2, THBS1, TLR2, TNF, TNFAIP2, TNFAIP3, TNFAIP6, TNIP3, TREM1, VNN1, VNN2, VNN3, ZC3H12A, and/or ZFP36 in the biological sample;

wherein a level of expression that is higher than a suitable control indicates that the subject is a candidate for treatment with the adenosine pathway inhibitor.

Embodiment 272. The method of embodiment 295, wherein the suitable control is a sample from a healthy subject, a sample from a non-cancerous tissue, or an average level of expression in a population.

Embodiment 273. The method of any one of embodiments 283 to 296, wherein the one or more genes is selected from ALOX5AP, AQP9, BCL2A1, BCL3, BIRC3, C15orf48, C19orf59, C5AR1, CCL2, CCL20, CCL3, CCL4, CCL7, CD300A, CD300E, CEACAM3, CFB, CLEC5A, CLEC7A, CSF3, CSF3R, CXCL1, CXCL2, CXCL3, CXCL5, CXCL6, CXCR1, CXCR2, EMR3, EREG, FCAR, FCGR3B, FFAR2, FOS, FOSL1, FPR1, FPR2, GOS2, GNA15, GPR109A, GPR109B, GPR183, GPR84, GPR97, HBEGF, ICAM1, IER3, IL10, IL1A, IL1B, IL1RN, IL6, IL8, JUNB, LIF, LILRA5, MAP3K8, MEFV, MNDA, NAMPT, NCOA7, NFKBIZ, NLRP3, OSM, PI3, PLAU, PLAUR, PPBP, PTGS2, RND3, S100A12, S100A8, S100A9, SAA1, SAA2, SAMSN1, SERPINB2, SERPINB8, SERPINE1, SLC11A1, SLC2A3, SOCS3, SOD2, SRGN, TNF, TNFAIP3, TNFAIP6, TREM1, VNN3, ZC3H12A, and/or ZFP36.

Embodiment 274. The method of any one of embodiments 283 to 296, wherein the one or more genes is selected from BCL2A1, CCL2, CCL20, CSF3, CXCL1, CXCL2, CXCL3, CXCL5, CXCL6, FCGR3B, FPR2, IER3, IL1B, IL6, IL8, NFKBIZ, OSM, PLAUR, PTGS2, S100A8, S100A9, SOCS3, and/or TREM1.

Embodiment 275. The method of any one of embodiments 283 to 298, wherein a level of protein is detected.

Embodiment 276. The method of embodiment 299, wherein the protein level is detected using immunohistochemistry.

Embodiment 277. The method of any one of embodiments 283 to 298, wherein a level of gene expression is detected.

Embodiment 278. The method of any one of embodiments 283 to 301, further including detecting a level of expression of one or more additional genes and/or one or more additional proteins in the sample.

Embodiment 279. The method of embodiment 302, wherein the one or more additional genes and/or one or more additional proteins is selected from the genes/proteins in Tables 1-9.

Embodiment 280. The method of any one of embodiments 283 to 303, wherein the level of expression in the biological sample is higher than a control.

Embodiment 281. The method of any one of embodiments 283 to 304, wherein expression of other genes or proteins is not detected.

Embodiment 282. The method of any one of embodiments 283 to 305, wherein the biological sample is selected from a blood sample, a tumor biopsy, or immune cells.

Embodiment 283. The method of embodiment 306, wherein the biological sample is a tumor biopsy.

Embodiment 284. The method of any one of embodiments 283 to 307, wherein gene expression is measured by RNA sequencing, nanopore sequencing, microarray, or hybridization-based sequencing (e.g., NanoString).

What is claimed is:

1. A method of treating a subject having cancer, the method comprising:
   (a) obtaining a biological sample from the subject;
   (b) detecting an increased level of expression of genes or proteins in the biological sample, relative to a control, wherein the genes or the proteins comprise CXCL1, CXCL2, CXCL3, CXCL5, CXCL6, CXCL8, IL-1β, and PTGS2; and
   (c) administering to the subject an effective amount of an adenosine pathway inhibitor, thereby treating the cancer.

2. The method of claim 1, wherein the genes or the proteins consist of CXCL1, CXCL2, CXCL3, CXCL5, CXCL6, CXCL8, IL-1β, and PTGS2.

3. The method of claim 1, wherein the adenosine pathway inhibitor is an adenosine 2A receptor antagonist.

4. The method of claim 3, wherein the adenosine 2A receptor antagonist is (S)-7-(5-methylfuran-2-yl)-3-((6-(((tetrahydrofuran-3-yl)oxy)methyl)pyridin-2-yl)methyl)-3H-[1,2,3]triazolo[4,5-d]pyrimidin-5-amine.

5. The method of claim 1, wherein the cancer is renal cancer.

6. The method of claim 1, wherein the biological sample is a blood sample, a tumor biopsy, or immune cells.

7. The method of claim 1, wherein detecting an increased level of expression of the gene or the protein is detecting an increased level of expression of the gene.

8. The method of claim 1, wherein the level of expression of the gene is detected by RNA sequencing, nanopore sequencing, microarray, or hybridization-based sequencing.

9. The method of claim 1, wherein detecting an increased level of expression of the gene or the protein is detecting an increased level of expression of the protein.

10. The method of claim 1, wherein the level of expression of the protein is detected by enzyme-linked immunosorbent assay or immunohistochemistry.

11. A method of treating renal cancer in a subject in need thereof, the method comprising:
   (a) obtaining a biological sample from the subject, wherein the biological sample is a blood sample, a tumor biopsy, or immune cells;
   (b) detecting an increased level of expression of genes or proteins in the biological sample, relative to a control, wherein the genes or the proteins comprise CXCL1, CXCL2, CXCL3, CXCL5, CXCL6, CXCL8, IL-1β, and PTGS2; and
   (c) administering to the subject an effective amount of (S)-7-(5-methylfuran-2-yl)-3-((6-(((tetrahydrofuran-3-yl)oxy)methyl)pyridin-2-yl)methyl)-3H-[1,2,3]triazolo[4,5-d]pyrimidin-5-amine, thereby treating the renal cancer.

* * * * *